United States Patent
Kayyem

(10) Patent No.: US 9,557,295 B2
(45) Date of Patent: *Jan. 31, 2017

(54) USE OF MICROFLUIDIC SYSTEMS IN THE ELECTROCHEMICAL DETECTION OF TARGET ANALYTES

(71) Applicant: Osmetech Technology, Carlsbad, CA (US)

(72) Inventor: Jon Faiz Kayyem, Pasadena, CA (US)

(73) Assignee: OSMETECH TECHNOLOGY, INC., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/837,254

(22) Filed: Aug. 27, 2015

(65) Prior Publication Data
US 2016/0054261 A1 Feb. 25, 2016

Related U.S. Application Data

(63) Continuation of application No. 13/921,117, filed on Jun. 18, 2013, now Pat. No. 9,151,746, which is a
(Continued)

(51) Int. Cl.
*G01N 27/453* (2006.01)
*G01N 27/447* (2006.01)
(Continued)

(52) U.S. Cl.
CPC ....... *G01N 27/44791* (2013.01); *B01L 3/5027* (2013.01); *B01L 3/50273* (2013.01); *B01L 3/502715* (2013.01); *B01L 3/502738* (2013.01); *B01L 3/502761* (2013.01); *C12Q 1/6813* (2013.01); *C12Q 1/6825* (2013.01); *G01N 27/3275* (2013.01); *G01N 27/3276* (2013.01); *G01N 27/447* (2013.01); *G01N 27/4473* (2013.01); *G01N 33/5302* (2013.01); *G01N 33/5438* (2013.01); *G01N 33/54386* (2013.01); *B01L 7/52* (2013.01); *B01L 7/525* (2013.01);
(Continued)

(58) Field of Classification Search
CPC ............... G01N 27/4473; G01N 27/44752; G01N 27/44791
See application file for complete search history.

(56) References Cited

U.S. PATENT DOCUMENTS 4,707,440 A   11/1987   Stavrianopoulos
4,711,955 A   12/1987   Ward et al.
(Continued)

FOREIGN PATENT DOCUMENTS

CA   2090904   9/1993
EP   0 063 870 A2   11/1982
(Continued)

OTHER PUBLICATIONS

Aizawa, M., et al., "Integrated molecular systems for biosensors," *Sens. Actuators B Chem.* 24(1&3):1-5 (1995).
(Continued)

*Primary Examiner* — Alexander Noguerola
(74) *Attorney, Agent, or Firm* — Morgan, Lewis & Bockius LLP; Robin M. Silva

(57) ABSTRACT

The invention relates generally to methods and apparatus for conducting analyses, particularly microfluidic devices for the detection of target analytes.

20 Claims, 2 Drawing Sheets

Related U.S. Application Data continuation of application No. 11/981,541, filed on Oct. 30, 2007, now Pat. No. 8,486,247, which is a continuation of application No. 11/043,515, filed on Jan. 25, 2005, now Pat. No. 7,534,331, which is a continuation of application No. 09/295,691, filed on Apr. 21, 1999, now Pat. No. 6,942,771.

(51) Int. Cl.
| | | |
|---|---|---|
| *G01N 27/327* | (2006.01) | |
| *B01L 3/00* | (2006.01) | |
| *C12Q 1/68* | (2006.01) | |
| *G01N 33/543* | (2006.01) | |
| *G01N 33/53* | (2006.01) | |
| *B01L 7/00* | (2006.01) | |
| *B01L 9/00* | (2006.01) | |
| *B82Y 30/00* | (2011.01) | |
| *B82Y 40/00* | (2011.01) | |
| *G01N 35/00* | (2006.01) | |
| *B82Y 35/00* | (2011.01) | |

(52) U.S. Cl.
CPC ............ *B01L 9/527* (2013.01); *B01L 2200/10* (2013.01); *B01L 2300/021* (2013.01); *B01L 2300/0636* (2013.01); *B01L 2300/0645* (2013.01); *B01L 2300/0816* (2013.01); *B01L 2300/0877* (2013.01); *B01L 2300/0887* (2013.01); *B01L 2400/0415* (2013.01); *B01L 2400/0418* (2013.01); *B01L 2400/0439* (2013.01); *B01L 2400/0442* (2013.01); *B01L 2400/0481* (2013.01); *B01L 2400/0487* (2013.01); *B01L 2400/0611* (2013.01); *B01L 2400/0633* (2013.01); *B01L 2400/0638* (2013.01); *B01L 2400/0677* (2013.01); *B82Y 30/00* (2013.01); *B82Y 35/00* (2013.01); *B82Y 40/00* (2013.01); *G01N 27/44752* (2013.01); *G01N 2035/00158* (2013.01); *G01N 2610/00* (2013.01)

(56) References Cited

U.S. PATENT DOCUMENTS

| | | | |
|---|---|---|---|
| 4,755,458 A | 7/1988 | Rabbani et al. | |
| 4,822,746 A | 4/1989 | Walt | |
| 4,840,893 A | 6/1989 | Hill et al. | |
| 4,849,513 A | 7/1989 | Smith et al. | |
| 4,868,103 A | 9/1989 | Stavrianopoulos et al. | |
| 4,894,325 A | 1/1990 | Englehardt et al. | |
| 4,943,523 A | 7/1990 | Stavrianopoulos | |
| 4,952,685 A | 8/1990 | Stavrianopoulos | |
| 4,965,188 A | 10/1990 | Mullis et al. | |
| 4,994,373 A | 2/1991 | Stavrianopoulos et al. | |
| 5,013,831 A | 5/1991 | Stavrianopoulos | |
| 5,061,336 A | 10/1991 | Soane | |
| 5,064,618 A | 11/1991 | Baker et al. | |
| 5,071,531 A | 12/1991 | Soane | |
| 5,082,830 A | 1/1992 | Brakel et al. | |
| 5,110,745 A | 5/1992 | Kricka et al. | |
| 5,114,864 A | 5/1992 | Walt | |
| 5,126,022 A | 6/1992 | Soane et al. | |
| 5,135,627 A | 8/1992 | Soane | |
| 5,143,853 A | 9/1992 | Walt | |
| 5,175,269 A | 12/1992 | Stavrianopoulos | |
| 5,192,507 A | 3/1993 | Taylor et al. | |
| 5,194,133 A | 3/1993 | Clark et al. | |
| 5,241,060 A | 8/1993 | Engelhardt et al. | |
| 5,244,636 A | 9/1993 | Walt et al. | |
| 5,278,043 A | 1/1994 | Bannwarth et al. | |
| 5,296,375 A | 3/1994 | Kricka et al. | |
| 5,312,527 A | 5/1994 | Mikkelsen et al. | |
| 5,328,824 A | 7/1994 | Ward et al. | |
| 5,401,378 A | 3/1995 | King et al. | |
| 5,403,451 A | 4/1995 | Riviello et al. | |
| 5,449,767 A | 9/1995 | Ward et al. | |
| 5,472,881 A | 12/1995 | Beebe et al. | |
| 5,476,928 A | 12/1995 | 'Ward et al. | |
| 5,486,335 A | 1/1996 | Wilding et al. | |
| 5,498,392 A | 3/1996 | Wilding et al. | |
| 5,505,321 A | 4/1996 | Caron et al. | |
| 5,519,635 A | 5/1996 | Miyake et al. | |
| 5,565,322 A | 10/1996 | Heller | |
| 5,569,364 A | 10/1996 | Hooper et al. | |
| 5,573,906 A | 11/1996 | Bannwarth et al. | |
| 5,585,069 A * | 12/1996 | Zanzucchi ............ | B01J 19/0093 204/450 |
| 5,587,128 A | 12/1996 | Wilding et al. | |
| 5,591,578 A | 1/1997 | Meade et al. | |
| 5,593,838 A | 1/1997 | Zanzucchi et al. | |
| 5,601,982 A | 2/1997 | Sargent et al. | |
| 5,605,662 A | 2/1997 | Heller et al. | |
| 5,631,337 A | 5/1997 | Sassi et al. | |
| 5,632,876 A * | 5/1997 | Zanzucchi ............ | B01F 13/0077 204/600 |
| 5,635,358 A | 6/1997 | Wilding et al. | |
| 5,637,469 A | 6/1997 | Wilding et al. | |
| 5,643,738 A | 7/1997 | Zanzucchi et al. | |
| 5,681,484 A | 10/1997 | Zanzucchi et al. | |
| 5,694,932 A | 12/1997 | Michel | |
| 5,705,348 A | 1/1998 | Meade et al. | |
| 5,726,026 A | 3/1998 | Wilding et al. | |
| 5,727,548 A | 3/1998 | Hill et al. | |
| 5,728,532 A | 3/1998 | Ackley | |
| 5,741,462 A | 4/1998 | Nova et al. | |
| 5,741,700 A | 4/1998 | Ershov et al. | |
| 5,747,169 A | 5/1998 | Fan et al. | |
| 5,750,015 A | 5/1998 | Soane et al. | |
| 5,755,942 A | 5/1998 | Zanzucchi et al. | |
| 5,756,050 A | 5/1998 | Ershow et al. | |
| 5,770,029 A | 6/1998 | Nelson et al. | |
| 5,770,369 A | 6/1998 | Meade et al. | |
| 5,770,721 A | 6/1998 | Ershov et al. | |
| 5,776,672 A | 7/1998 | Hashimoto et al. | |
| 5,780,234 A | 7/1998 | Meade et al. | |
| 5,824,473 A | 10/1998 | Meade et al. | |
| 5,851,772 A | 12/1998 | Mirzabekov et al. | |
| 5,856,174 A | 1/1999 | Lipshutz et al. | |
| 5,863,502 A | 1/1999 | Southgate et al. | |
| 5,952,172 A | 9/1999 | Meade et al. | |
| 6,013,170 A | 1/2000 | Meade | |
| 6,013,459 A | 1/2000 | Meade | |
| 6,048,692 A | 4/2000 | Maracas et al. | |
| 6,071,699 A | 6/2000 | Meade et al. | |
| 6,087,100 A | 7/2000 | Meade et al. | |
| 6,090,933 A | 7/2000 | Kayyem et al. | |
| 6,096,273 A | 8/2000 | Kayyem et al. | |
| 6,100,045 A | 8/2000 | Van Es | |
| 6,114,122 A | 9/2000 | Besemer et al. | |
| 6,177,250 B1 | 1/2001 | Meade et al. | |
| 6,180,352 B1 | 1/2001 | Meade et al. | |
| 6,200,761 B1 | 3/2001 | Meade et al. | |
| 6,225,059 B1 | 5/2001 | Ackley et al. | |
| 6,232,062 B1 | 5/2001 | Kayyem et al. | |
| 6,238,870 B1 | 5/2001 | Meade et al. | |
| 6,258,545 B1 | 7/2001 | Meade et al. | |
| 6,258,593 B1 | 7/2001 | Schembri et al. | |
| 6,264,825 B1 | 7/2001 | Blackburn et al. | |
| 6,268,149 B1 | 7/2001 | Meade et al. | |
| 6,268,150 B1 | 7/2001 | Meade et al. | |
| 6,277,576 B1 | 8/2001 | Meade et al. | |
| 6,290,839 B1 | 9/2001 | Kayyem et al. | |
| 6,300,141 B1 | 10/2001 | Segal et al. | |
| 6,306,584 B1 | 10/2001 | Bamdad | |
| 6,326,211 B1 | 12/2001 | Anderson et al. | |
| 6,528,266 B2 | 3/2003 | Meade et al. | |
| 6,541,617 B1 | 4/2003 | Bamdad et al. | |
| 6,600,026 B1 | 7/2003 | Yu | |
| 6,761,816 B1 | 7/2004 | Blackburn et al. | |
| 6,942,771 B1 | 9/2005 | Kayyem | |
| 7,018,523 B2 | 3/2006 | Meade | |

(56) References Cited

U.S. PATENT DOCUMENTS

| | | | |
|---|---|---|---|
| 7,087,148 | B1 | 8/2006 | Blackburn et al. |
| 7,534,331 | B2 | 5/2009 | Kayyem |
| 9,151,746 | B2 * | 10/2015 | Kayyem ............... B01L 3/5027 |
| 2003/0170677 | A1 | 9/2003 | Meade et al. |
| 2004/0101890 | A1 | 5/2004 | Meade et al. |
| 2005/0003399 | A1 | 1/2005 | Blackburn et al. |

FOREIGN PATENT DOCUMENTS

| | | | |
|---|---|---|---|
| EP | 0 234 938 A2 | | 2/1987 |
| EP | 0 229 943 A2 | | 7/1987 |
| EP | 0 599 337 A2 | | 6/1994 |
| EP | 0 515 615 A1 | | 9/1996 |
| EP | 0 637 996 B2 | | 7/1997 |
| EP | 0 637 998 B2 | | 7/1997 |
| JP | 63-238166 A | | 10/1988 |
| JP | 6-41183 A | | 2/1994 |
| JP | 9061312 | | 3/1997 |
| WO | WO 90/05732 A1 | | 5/1990 |
| WO | WO 92/10757 A1 | | 6/1992 |
| WO | WO 93/10267 A1 | | 5/1993 |
| WO | WO 93/22678 A1 | | 11/1993 |
| WO | WO 93/23425 A1 | | 11/1993 |
| WO | WO 95/10040 A1 * | 4/1995 | ........... G01N 27/447 |
| WO | WO 95/15971 A1 | | 6/1995 |
| WO | WO 96/06946 A1 | | 3/1996 |
| WO | WO 96/15576 A1 | | 5/1996 |
| WO | WO 96/28538 A1 | | 9/1996 |
| WO | WO 96/39252 A1 | | 12/1996 |
| WO | WO 96/40712 A1 | | 12/1996 |
| WO | WO 97/01646 A1 | | 1/1997 |
| WO | WO 97/27324 A1 | | 7/1997 |
| WO | WO 97/27329 A1 | | 7/1997 |
| WO | WO 97/37755 A1 | | 10/1997 |
| WO | WO 97/43629 A1 | | 11/1997 |
| WO | WO 97/44651 A1 | | 11/1997 |
| WO | WO 98/05424 | | 2/1998 |
| WO | WO 98/12539 A2 | | 3/1998 |
| WO | WO 98/12539 A3 | | 3/1998 |
| WO | WO 98/20162 A2 | | 5/1998 |
| WO | WO 98/20162 A3 | | 5/1998 |
| WO | WO 98/27229 A1 | | 6/1998 |
| WO | WO 98/28444 A2 | | 7/1998 |
| WO | WO 98/28444 A3 | | 7/1998 |
| WO | WO 98/31839 A2 | | 7/1998 |
| WO | WO 98/31839 A3 | | 7/1998 |
| WO | WO 98/35232 A2 | | 8/1998 |
| WO | WO 98/35232 A3 | | 8/1998 |
| WO | WO 98/38510 A2 | | 9/1998 |
| WO | WO 98/38510 A3 | | 9/1998 |
| WO | WO 98/57159 A1 | | 12/1998 |
| WO | WO 99/14596 A1 | | 3/1999 |
| WO | WO 99/33559 | | 7/1999 |
| WO | WO 99/67425 | | 12/1999 |
| WO | WO 99/67628 | | 12/1999 |
| WO | WO 00/62931 A1 | | 10/2000 |
| WO | WO 01/35100 | | 5/2001 |
| WO | WO 01/54813 | | 8/2001 |
| WO | WO 02/43864 | | 6/2002 |

OTHER PUBLICATIONS

Albers, W., et al., "Design of novel molecular wires for realizing long-distance electron transfer," *Biochem. Bioenerg.* 42(1):25-33 (1997).

Alleman, K.S., et al., Electrochemical rectification at a monolayer-modified electrode, *J. Phys. Chem.* 100:17050-17058 (1996).

Barisci, J. N., et al., "Conducting Polymer Sensors," *Trends Biotechnol.* 4(9):307-311 (1996).

Bechtold, R., et al., "Ruthenium-modified horse heart cytochrome c: effect of pH and ligation on the rate of intramolecular electron transfer between ruthenium(II) and heme(III)," *J. Phys. Chem.* 90(16):3800-3804 (1986).

Bidan, G., "Electroconducting conjugated polymers: new sensitive matrices to build up chemical or electrochemical sensors. A Review.," *Sens. Actuators B* 6:45-56 (1992).

Blonder, R., et al., "Application of redox enzymes for probing the antigen-antibody association at the monolayer interfaces: development of amperometric immunosensor electrodes," *Anal. Chem.* 58(18):3151-3157 (1996).

Blonder, R., et al., "Three-dimensional redox-active layered composites of Au—Au, Ag—Ag, and Au—Ag colloids," *Chem. Commun.* 13:1393-1394 (1998).

Boguslavsky, L. et al., "Applications of redox polymers in biosensors," *Solid State Ionics* 60:189-197 (1993).

Bowler, B.E., et al., "Long-Range electron transfer in donor (spacer) acceptor molecules and proteins," *Prog. Inorg. Chem. Bioinorg. Chem.* 38:259-322 (1990).

Brodolin, K., et al., "Conformational changes in *E. coli* RNA polymerase during promoter recognition," *Nucleic Acids Res.* 24(24):5748-5753 (Dec. 1993).

Brun, A., et al., "Photochemistry of intercalated quaternary diazaaromatic salts," *J. Am. Chem. Soc.* 113(21):8153-8159 (Oct. 1991).

Bumm, L.A., et al., "Are Single Molecular Wires Conducting?," *Science* 271(5226):1705-1707 (Mar. 1996).

Cantor, C.R., et al., "Report on the sequencing by hybridization workshop," *Genomics* 13(4):1378-1383 (Aug. 1992).

Carr, J., et al., "Novel electrochemical sensors for neutral molecules," *Chem. Commun.* 1649-1650 (1997).

Carter, M., et al., "Voltammetric studies of the interaction of metal chelates with DNA. 2. Tris-chelated complexes of cobalt(III) and iron(II) with 10-phenanthroline and 2,2'-bipyridine," *J. Am. Chem. Soc.* 111(24):8901-8911 (Nov. 1989).

Chang, I-Jy, et al., "High-driving-force electron transfer in metalloproteins: Intramolecular oxidation of ferrocytochrome *c* by Ru(2,2'-bpy)$_2$(im)(His-33)$^{3+}$," *J. Am. Chem. Soc.* 113(18):7056-7057 (Aug. 1991).

Chidsey, C., et al., "Coadsorption of ferrocene-terminated and unsubstituted alkanethiols on gold electroactive self-assembled monolayers," *J. Am. Chem. Soc.* 112(11):4301-4306 (May 1990).

Chidsey, C., et al., "Free energy and temperature dependence of electron transfer at the metal electrolyte interface," *Science* 251:919-923 (1991).

Chrisey, C., et al., "Covalent attachment of synthetic DNA to self-assembled monolayer films," *Nucleic Acids Res.*, 24(15):3031-3039 (1996).

Clery, D., "DNA Goes Electric," *Science* 267(5202)1 270 (Mar. 1995).

Davis, L.M., et al., "Electron donor properties of the antitumour drug amsacrine as studied by fluorescence quenching of DNA-bound ethidium," *Chem.-Biol. Interact.* 62:45-58 (1987).

Davis, L.M., et al., "Elements of biosensor construction," *Enzyme Microb. Technol.* 17:1030-1035 (1995).

Degani, Y., et al., "Direct electrical communication between chemically modified enzymes and metal electrodes. 1. Electron transfer from glucose oxidase to metal electrodes via electron relays, bound covalently to the enzyme," *J. Phys. Chem.* 91(6):1285-1288 (1987).

Degani, Y., et al., "Electrical communication between redox centers of glucose oxidase and electrodes via electrostatically and covalently bound redox polymers," *J. Am. Chem. Soc.* 111(6):2357-2358 (Mar. 1989).

Deinhammer, R.S., et al., "Electronchemical Oxidation of Amine-containing compounds: A Route to the Surface Modification of glassy carbon electrodes," *Langmuir* 10(4):1306-1313 (Apr. 1994).

Dontha, et al., "Generation of Biotin/Avidin/Enzyme Nanostructures with Maskless Photolithography," *Anal. Chem.* 69:2619-2625 (1997).

Drobyshev, A., et al., "Sequence analysis by hybridization with oligonucleotide microchip: Identification of β-thalassemia mutations," *Gene* 188(1):45-52 (Mar. 1997).

Dubiley, S., et al., "Fractionation, phosphorylation and ligation on oligonucleotide microchips to enhance sequencing by hybridization," *Nucleic Acids Res.* 25(12):2259-2265 (Jun. 1997).

(56) References Cited

OTHER PUBLICATIONS

Durham, B., et al., "Electron-transfer kinetics of singly labeled ruthenium(ii) polypyridine cytochrome c derivatives," *Adv. Chem. Ser.* 226:181-193 (1990).

Durham, B., et al., "Photoinduced electron-transfer kinetics of singly labeled ruthenium bis(bipyridin) dicarboxybipyridine cytochrome *c* derivatives," *Biochemistry* 28(21):8659-8665 (Oct. 1989).

Elghanian, R., et al., "Selective colorimetric detection of polynucleotides based on the distance-dependent optical properties of gold nanoparticles," *Science* 277(5329):1078-1081 (Aug. 1997).

Elias, H., et al., "Electron-transfer kinetics of Zn-substituted cytochrome *c* and its $Ru(NH_3)_5$(histidine-33) derivative," *J. Am. Chem. Soc.* 110:429-434 (1988).

Esipova, N., et al., "Investigation of sites of strong DNA-protein interactions in DNA-binding proteins by theoretical and DNA-protein cross-linking methods," *J. Biomol. Struct. Dynam.* 12(6):A049 (Jun. 1995).

Farver, O., et al., "Long-range intramolecular electron transfer in azurins," *Proc. Natl. Acad. Sci. USA* 86(18):6968-6972 (Sep. 1989).

Fotin, A., et al., "Parallel thermodynamic analysis of duplexes on oligodeoxynucleotide microchips," *Nucleic Acids Res.* 216(6):1515-1521 (Mar. 1998).

Fox, L.S., et al., "Gaussian free-energy dependence of electron-transfer rates in iridium complexes," *Science* 247(4960):1069-1071 (Mar. 1990).

Fox, M.A., et al., "Light-Harvesting Polymer Systems," *Chem. Eng. News*, pp. 38-48 (Mar. 15, 1993).

François, J-C., et al., "Periodic cleavage of poly(dA) by oligothymidylates covalently linked to the 1,10-phenanthroline-copper complex," *Biochemistry* 27:2272-2276 (1988).

Fromherz, P., et al., "Photoinduced electron transfer in dna matrix from intercalated ethidium to condensed methylviologen," *J. Am. Chem. Soc.* 108(17):5361-5362 (Aug. 1986).

Gardner, J., et al., "Application of conducting polymer technology in microsystems," *Sens. Actuators A* 51(1):57-66 (Oct. 1995).

Gregg, B.A., et al., "Cross-linked redox gels containing glucose oxidase for amperometric biosensor applications," *Anal. Chem.*, 62(3):258-263 (Feb. 1990).

Gregg, B.A., et al., "Redox polymer films containing enzymes. 1. A redox-conducting epoxy cement: synthesis, characterization, and electrocatalytic oxidation of hydroquinone," *J. Phys. Chem.* 95(15):5970-5975 (Jul. 1991).

Guschin, D., et al., "Manual manufacturing of oligonucleotide, DNA, and protein microchips," *Anal. Biochem.* 250(2):203-211 (Aug. 1997).

Guschin, D., et al., "Oligonculeotide microchips as genosensors for determinative and environmental studies in microbiology," *Appl. Env. Microbiol.* 63(6):2397-2402 (Jun. 1997).

Hashimoto, K., et al., "Sequence-specific gene detection with a gold electrode modified with dna probes and an electrochemically active dye," *Anal. Chem.* 66(21):3830-3833 Nov. 1994.

Hegner, M., et al., "Immobilizing DNA on gold via thiol modification for atomic force microscopy imaging in buffer solutions," *FEBS Lett.* 336(3):452-456 (Dec. 1993).

Heller, A., "Fluorescent energy transfer oligonucleotide probes," *Fed. Proc.* 46(6):1968 (1987).

Heller, A., et al., "Amperometric biosensors based on three-dimensional hydrogel-forming epoxy networks," *Sens. Actuators* 13-14:180-183 (1993).

Hobbs, J., et al., "Polynucleotides containing 2'-amino-2'deoxyribose and 2!-azido-2'-deoxyriose," *Biochemistry* 12(25):5138-5145 (Dec. 1973).

Hsung, R., et al., "Synthesis and characterization of unsymmetric ferrocene-terminated phenylethynyl oligomers," *Organometallics*, 14(10):4808-4815 (Oct. 1995).

Hsung, R., et al., "Thiophenol protecting groups for the palladium-catalyzed heck reaction: efficient syntheses of conjugated arylthiols," *Tetrahedron Lett.* 36(26):4525-4528 (Jun. 1995).

Jenkins, Y., et al., A Sequence-specific molecular light switch: tebhering of an oligonucleotide to a dipyridophenazine complex of ruthenium (II), *J. Am. Chem. Soc.* 114(22):8736-8738 (Oct. 1992).

Johnston, D., et al., "Trans-dioxorhenium(v)-mediated electrocatalytic oxidation of DNA at indium tin-oxide electrodes: voltammetric detection of DNA cleavage in solution," *Inorg. Chem.* 33:6388-6390 (1994).

Kamat, P., et al., "Photochemistry on surfaces: 2. Intramolecular electron transfer on colloidal alumina-coated silica particles," *J. Phys. Chem* 93(4):1405-1409 (Feb. 1989).

Katritzky, A., et al., "Pyridylethylation—a new protection method for active hydrogen compounds," *Tetrahedron Lett.* 25(12):1223-1226 (1984).

Kelly, S.O., et al., "Electrochemistry of methylene blue bound to a DNA-modified electrode," *Bioconjugate Chem.* 8:31-37 (1997).

Kojima, H., et al., "A DNA probe of ruthenium bipyridine complex using photocatalytic activity," *Chem. Lett.* 18:1889-1982 (1989).

Korri-Youssoufi, H., et al., "Toward bioelectronics: specific DNA recognition based on an oligonucleotide-functionalized polypyrrole," *J. Am. Chem. Soc.* 119(31):7388-7389 9 (Aug. 1997).

Laviron, E., "A.C. polarography and Faradaic impedance of strongly adsorbed electroactive species. part I: theoretical and experimental study of a quasi-reversible reaction in the case of a Langmuir isotherm," *J. Electroanal. Chem.* 97(2):135-149 (Mar. 1979).

Laviron, E., "A.C. polarography and Faradaic impedance of strongly adsorbed electoactive species. part III: theoretical complex plane analysis for a surface redox reaction," *J. Electroanal. Chem.* 105(1):35-42 (Dec. 1979).

Lee, G., et al., "Direct measurement of the forces between complementary strands of DNA," *Science* 266(5186):771-773 (Nov. 1994).

Lenhard, J.R., et al., "Part VII Covalent Bonding of a Reversible-Electrode Reactanbt to Pt Electrodes Using an organosilane Reagent" *J. Electronal. Chem.* 78(1):195-201 (May 1977).

Liu, et al., "Passive Mixing in a Three-Dimensional Serpentine Microchannel," *Journal of Microelectromechanical Systems* 9(2):190-196 (2000).

Livshits, M., et al., "Theoretical analysis of the kinetics of DNA hybridization with gel-immobilized oligonucleotides," *Biophys. J.* 71:2795-2801 (Nov. 1996).

Maskos, U., et al., "Oligonucleotide hybridisations on glass supports: a novel linker for oligonucleotide synthesis and hybridisation properties of oligonucleotides synthesised in situ," *Nucleic Acids Res.* 20(7):1679-1684 (Apr. 1992).

Mazzocchi, P., et al., "Photolysis of N-(2-methyl-2-propenyl)phthalimide in methanol. evidence supporting radical-radical coupling of a photochemically generated radical ion pair," *J. Am. Chem. Soc.* 108(18):5361-5362 (Aug. 1986).

McGee, D., et al., "2'-amino-2'-deoxyuridine via an intramolecular cyclization of a trichloroacetimidate," *J. Org. Chem.* 61(2):781-785 (Jan. 1996).

Meade, T., "Driving-force effects on the rate of long-range electron transfer in ruthenium-modified cytochrome c," *J. Am. Chem. Soc.* 111(12):4353-4356 (Jun. 1989).

Meade, T., et al., "Electron transfer through DNA: site-specific modification of duplex DNA with ruthenium donors and acceptors," *Angew Chem. Int. Ed. Engl.* 34(3):352 (Feb. 1995).

Mestel, R., "'Electron Highway' Points to Identity of DNA," *New Scientist* 145(1967):21 (Mar. 1995).

Millan, K., et al., "Covalent immobilization of DNA onto glassy carbon electrodes," *Electroanalysis* 4(10):929-932 (1992).

Millan, K., et al., "Sequence-selective biosensor for dna based on electroactive hybridization indicators," *Anal. Chem* Millan, K., et al., "Voltammetric DNA biosensor for cystic fibrosis based on a modified carbon paste electrode," *Anal. Chem.* 66(18):2943-2948 (Sep. 1994).. 65(17):2317-2323 (Aug. 1993).

Millan, K., et al., "Voltammetric DNA biosensor for cystic fibrosis based on a modified carbon paste electrode," *Anal. Chem.* 66(18):2943-2948 (Sep. 1994).

Miller, C., "Absorbed ω-hydroxy thiol monolayers on gold electrodes: evidence for electron tunneling to redox species in solution," *J. Phys. Chem.* 95:877-886 (1991).

(56) References Cited

OTHER PUBLICATIONS

Mirkin, C., et al., "A DNA-based method for rationally assembling nanoparticles into macroscopic materials," *Nature* 382(6592):607-609 (Aug. 1996).

Mirzabekov, A., et al., "DNA sequencing by hybridization—a megasequencing emthod and a diagnostic tool," *Trends Biotechnol.* 12(1):27-32 (Jan. 1994).

Mitchell, G., et al., "Programmed assembly of DNA functionalized quantum dots," *J. Am. Chem. Soc.* 121(35):8122-8123 (Sep. 1998).

Mucic, R., et al., "DNA-directed synthesis of binary nanoparticle network materials," *J. Am. Chem. Soc.* 120(48):12674-12675 (Dec. 1998).

Mucic, R., et al., "Synthesis and characterization of DNA with ferrocenyl groups attached to their 5'-termini: electrochemical characterization of a redox-active nucleotide monolayer," *Chem. Commun.* 4:555-557 (1996).

Murphy, C. J., et al., "Long-range photoinduced electron transfer through a DNA helix," *Science* 262:1025-1029 (1993).

Orellana, G., et al., "Photoinduced electron transfer quenching of excited Ru(II) polypyridyls bound to DNA: The role of the nucleic acid double helix," *Photochem. Photobiol.* 54(4):499-509 (Oct. 1991).

Paleček, E., "From polarography of DNA to microanalysis with nucleic acid-modified electrodes," *Electroanalysis* 8(1):7-14 (Jan. 1996).

Parinov, S., "DNA Sequencing by hybridization to microchip octa- and decanucleotides extended by stacked pentanucleotides," *Nucleic Acids Res.* 24(15):2998-3004 (Aug. 1996).

Parinov, S., et al., "DNA sequencing by hybridization to microchip octa- and decanucleotides extended by stacked pentanucleotides," *Nucleic Acids Res.* 24(15):2998-3004 (Aug. 1996).

Paterson, D., "Electric genes: current flow in DNA could lead to faster genetic testing," *Sci. Am.* pp. 33-34 (May 1995).

Proudnikov, D., "Immobilization of DNA in polyacrylamide gel for the manufacture of DNA and DNA-oligonucleotide microchips," *Anal. Biochem.* 259(1):34-41 (May 1998).

Proudnikov, D., et al., "Chemical methods of DNA and RNA fluorescent labeling," *Nucleic Acids Res.* 24(22):4535-4542 (Nov. 1996).

Purugganan, M.D., et al., Accelerated electron transfer between metal complexes mediated by DNA, *Science* 241(4873):1645-1649 (Sep. 1988).

Reimers, J.R., et al., "Toward efficient molecular wires and switches: the brooker ions," *Biosystems* 35:107-111 (1995).

Rhodes, D. et al., "Helical periodicity of DNA determined by enzyme digestion," *Nature* 286(5773):573-578 (Aug. 1980).

Risser, S. M., et al., "Electron transfer in DNA: Predictions of exponential growth and decay of coupling with donor-acceptor distance," *J. Am. Chem. Soc.* 115(6):2508-2510 (Oct. 1993).

Sato, Y., et al., "Unidirectional electron transfer at self-assembled monolayers of 11-ferrocenyl-1-undecanethiol on gold," *Bull. Chem. Soc. Jpn.* 66(4):1032-1037 (1993).

Satyanarayana, S., et al., "Neither Δ- nor Λ-Tris(phenanthroline)ruthenium(II) binds to DNA by classical intercalation," *Biochemistry* 31(39):9319-9324 (Oct. 1992).

Schreiber, et al., "Bis(purine) complexes of trans-$a_2pt^{ii}$: preparation and x-ray structures of bis(9-methyladenine) and mixed 9-methyladenine, 9-methylguanine complexes and chemistry relevant to metal-modified nucelobase triples and quartets," *J. Am. Chem. Soc.* 118(:4124-4132 (1996).

Schuhmann, W., et al., "Electron transfer between glucose oxidase and electrodes via redox mediators bound with flexible chains to the enzyme surface," *J. Am. Chem. Soc.* 113(4):1394-1397 (Feb. 1991).

Schumm, J., et al., "Iterative divergent/convergent approach to linear conjugated oligomers by successive doubling of the molecular length: a rapid route to a 128 $\hbar$-long potential molecular wire," *Angew. Chem. Int. Ed. Engl.* 33(13):1360-1363 (Jul. 1994).

Sigal, G., et al., "A Self-assembled monolayer for the binding and study of histidine-tagged proteins by surface plasmon resonance," *Anal. Chem.* 68(3):490-497 (Feb. 1996).

Storhoff, J., et al., "One-pot colorimetric differentiation of polynucleotides with single base imperfections using gold nanoparticles probes," *J. Am. Chem. Soc.* 120(9):1959-1964 (Mar. 1998).

Strobel, S., et al., "Site-specific cleavage of a yeast chromosome by oligonucleotide-directed triple-helix format Su, et al., "Interfacial nucleic acid hybridization studied by random primer $^{32}P$ labelling and liquid-phase acoustic network analysis," *Anal. Chem.* 66(6):769-777 (Mar. 1994).ion," *Science* 249(4964):73-75 (Jul. 1990).

Su, et al., "Interfacial nucleic acid hybridization studied by random primer $^{32}P$ labelling and liquid-phase acoustic network analysis," *Anal. Chem.* 66(6):769-777 (Mar. 1994).

Telser, J., et al., "DNA duplexes covalently labeled at two sites: synthesis and characterization by steady-state and time-resolved optical spectroscopies," *J. Am. Chem. Soc.* 111(18):7226-7232 (Aug. 1989).

Telser, J., et al., "DNA oligomers and duplexes containing a covalently attached derivative of tris(2,2'-bipyridine)ruthenium(II): synthesis and characterization by thermodynamic and optical spectroscopic measurements," *J. Am. Chem. Soc.* 111(18):7221-7226 (Aug. 1989).

Timofeev, E., et al., "Methidium intercalator inserted into synthetic oligonucleotides," *Tetrahedron Lett.* 37(47):8467-8470 (Nov. 1996).

Timofeev, E., et al., "Regioselective immobilization of short oligonucleotides to acrylic copolymer gel," *Nucleic Acids Res.* 24(16):3142-3148 (Aug. 1996).

Tour, J., "Conjugated macromolecules of precise length and constitution. organic synthesis for the construction of nanoarchitectures," *Chem. Rev.* 96(1):537-553 (Feb. 1996).

Turro, N., et al. "Photoelectron transfer between molecules adsorbed in restricted spaces," *Photochem. Convers. Storage Sol. Energy, Proc. Int. Conf., $8^{th}$ Conf.* 8:121-139 (1990).

Turro, N.J., et al., "Molecular recognition and chemistry in restricted reaction spaces. Photophysics and photoinduced electron transfer on the surfaces of micelles, dendrimers, and DNA," *Acc. Chem. Res.* 24(11):332-340 (Nov. 1991).

Uosaki, K. et al., "A self-assembled monolayer of ferrocenylalkane thiols on gold as an electron mediator for the reduction of Fe(III)-EDTA in solution," *Electrochim. Acta.* 36(11/12):1799-1801 (1991).

Van Ness, J., et al., "A versatile solid support system for oligodeoxynucleotide probe-based hybridization assays," *Nucleic Acids Res.* 19(12):3345-3349 (Jun. 1991).

Watson, K., et al., "Hybrid nanoparticles with block copolymer shell structures," *J. Am. Chem. Soc.* 121(2):462-463 (Jan. 1999).

Weber, K., et al., "Voltammetry of redox-active groups irreversibly adsorbed onto electrodes. treatment using the marcus relation between rate and overpotential," *Anal. Chem.* 66:3164-3172 (Oct. 1994).

Winkler, J., et al., "Electron transfer in ruthenium-modified proteins," *Chem. Rev.* 92(3):369-379 (May 1992).

Xu, X., et al., "Immobilization and hybridization of DNA on an aluminum(III) alkanebisphosphonate thin film with electrogenerated chemiluminescent detection," *J. Am. Chem. Soc.* 117(9):2627-2631 (Mar. 1995).

Xu, X., et al., "Immobilization of DNA on an aluminum(III) alkaneobisphosphonate thin film with electrogenerated chemiluminescent detection," *J. Am. Chem. Soc.* 116(16):8386-8387 (Sep. 1994).

Yang, H., et al., "Growth and characterization of metal(II) alkaneobisphosphonate multilayer thin films on gold surfaces," *J. Am. Chem. Soc.* 115(25):11855-11862 (Dec. 1993).

Yershov, G., et al., "DNA analysis and diagnostics on oligonucleotide microchips," *Proc. Natl. Acad. Sci. USA* 93(10):4913-4918 (May 1996).

Zhou, Q., et al., "Fluorescent chemosensors based on energy migration in conjugated polymers: The molecular wire approach to increased sensitivity," *J. Am. Chem. Soc.* 117(50):12593-12602 (Dec. 1995).

\* cited by examiner

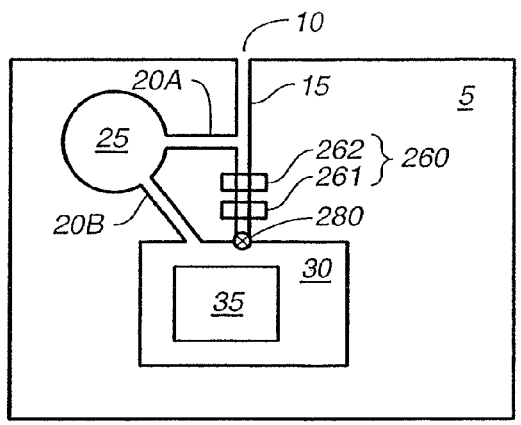
FIG._1A
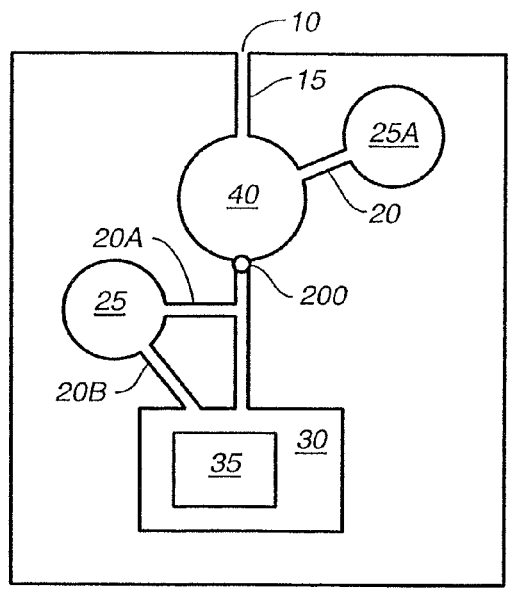
FIG._1B
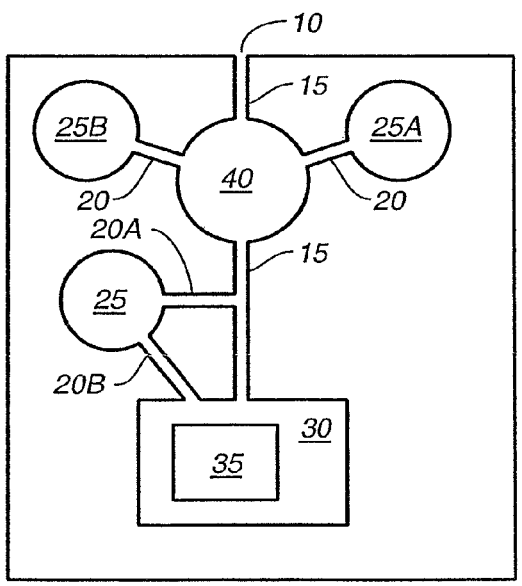
FIG._1C
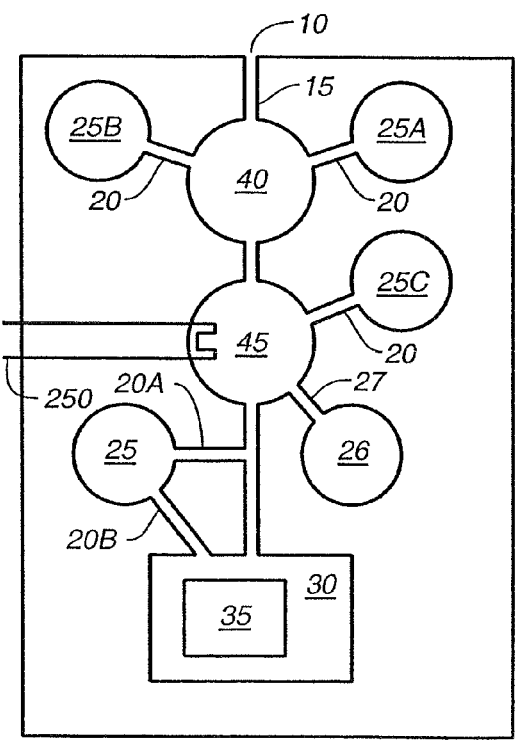
FIG._1D

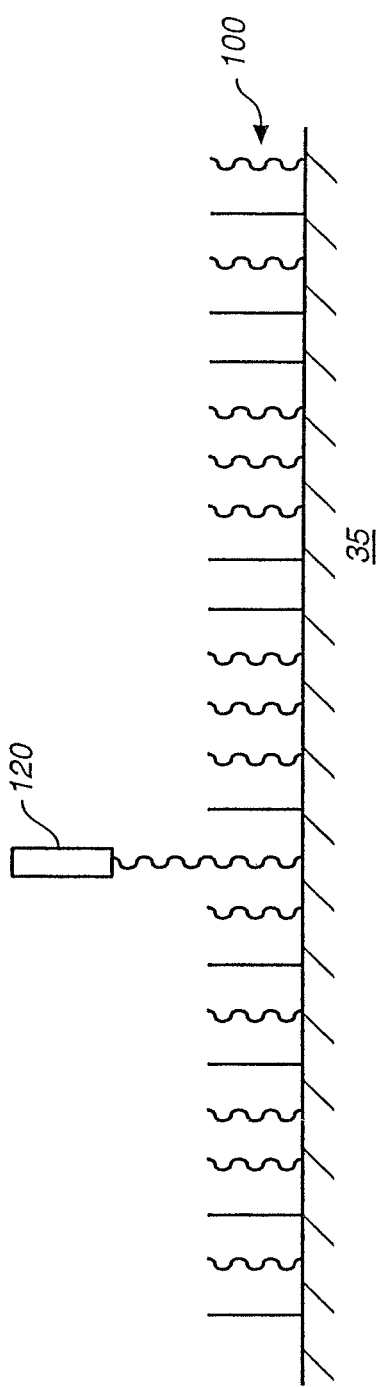

USE OF MICROFLUIDIC SYSTEMS IN THE ELECTROCHEMICAL DETECTION OF TARGET ANALYTES

CROSS-REFERENCES TO RELATED APPLICATIONS

This application is a continuation application of U.S. application Ser. No. 13/921,117, filed Jun. 18, 2013; which is a continuation of U.S. application Ser. No. 11/981,541, filed Oct. 30, 2007, now U.S. Pat. No. 8,486,247; which is a continuation application of U.S. application Ser. No. 11/043,515, filed Jan. 25, 2005, now U.S. Pat. No. 7,534,331; which is a continuation of U.S. application Ser. No. 09/295,691, filed Apr. 21, 1999, now U.S. Pat. No. 6,942,771, the disclosures of which are incorporated herein by reference in their entirety.

FIELD OF THE INVENTION

The invention relates generally to methods and apparatus for conducting analyses, particularly microfluidic devices for the detection of target analytes.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

There is a significant trend to reduce the size of these sensors, both for sensitivity and to reduce reagent costs. Thus, a number of microfluidic devices have been developed, generally comprising a solid support with microchannels, utilizing a number of different wells, pumps, reaction chambers, and the like. See for example EP 0637996 131; EP 0637998 BI; W096/39260; W097/16835; W098/13683; W097/16561; W097/43629; W09⁶/₃9252; W096/15576; W096/15450; W097i37755; and W097/27324; and U.S. Pat. Nos. 5,304,487; 5,071,531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351. However, there is a need for a microfluidic biosensor that can utilize electronic detection of the analytes.

However, there is a need for a microfluidic biosensor that can utilize electronic detection of the analytes.

BRIEF DESCRIPTION OF THE DRAWINGS

FIG. 1A, FIG. 1B, FIG. 1C and FIG. 1D depict some preferred embodiments of the invention. FIG. 1A depicts a solid support 5 that has a sample inlet port 10, a first microchannel 15, a storage module 25 (for example, for assay reagents) with a second microchannel 20. The second microchannel (20B) may be in fluid contact directly with the detection module 30 comprising a detection electrode 35, or (20A) in contact with the first microchannel 15. FIG. 1B depicts a sample handling well 40 and a second storage well 25A with a microchannel 20 to the sample handling well 40. For example, the sample handling well 40 could be a cell lysis chamber and the storage well 25A could contain lysis reagents. FIG. 1C depicts a sample handling well 40 that is a cell capture or enrichment chamber, with an additional reagent storage well 25B for elution buffer. FIG. 1D depicts the addition of a reaction module 45, with a storage module 25C for example for storage of amplification reagents. Optional waste module 26 is connected to the reaction module 45 via a microchannel 27. All of these embodiments may additionally comprise valves, waste wells, and pumps, including additional electrodes.

FIG. 2 depicts a cross-sectional view of a detection electrode according to one embodiment of the invention.

DETAILED DESCRIPTION OF THE INVENTION

The invention provides microfluidic cassettes or devices that can be used to effect a number of manipulations on a sample to ultimately result in target analytes detection or quantification. These manipulations can include cell handling (cell concentration, cell lysis, cell removal, cell separation, etc.), separation of the desired target analyte from other sample components, chemical or enzymatic reactions on the target analyte, detection of the target analyte, etc. The devices of the invention can include one or more wells for sample manipulation, waste or reagents; microchannels to and between these wells, including microchannels containing electrophoretic separation matrices; valves to control fluid movement; on-chip pumps such as electroosmotic, electrohydrodynamic, or electrokinetic pumps; and detection systems comprising electrodes, as is more fully described below. The devices of the invention can be configured to manipulate one or multiple samples or analytes.

The microfluidic devices of the invention are used to detect target analytes in samples. By "target analyte" or "analyte" or grammatical equivalents herein is meant any molecule, compound or particle to be detected. As outlined below, target analytes preferably bind to binding ligands, as is more fully described above. As will be appreciated by those in the art, a large number of analytes may be detected using the present methods; basically, any target analyte for which a binding ligand, described herein, may be made may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

In a preferred embodiment, the target analyte is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:1419 1986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), 0methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi at al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Left. 4:395 (1994); Jeffs et al., J. Biomolecular NMR 34:17 (1994); Tetrahedron Left. 37:743 (1996)) and nonribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169176). Several nucleic acid analogs are described in Rawls, C & E News Jun. 2, 1997 page 35. All of these references are hereby expressly incorporated by reference. These modifications of the ribosephosphate backbone may be done to facilitate the addition of electron transfer moieties, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or electron transfer moiety attachment, an analog structure may be used. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. This allows for better detection of mismatches. Similarly, due to their non-ionic nature, hybridization of the bases attached to these backbones is relatively insensitive to salt concentration. This is particularly advantageous in the systems of the present invention, as a reduced salt hybridization solution has a lower Faradaic current than a physiological salt solution (in the range of 150 mM).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribonucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as nucleosides.

In a preferred embodiment, the present invention provides methods of detecting target nucleic acids. By "target nucleic acid" or "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. In some embodiments, it may be desirable to fragment or cleave the sample nucleic acid into fragments of 100 to 10,000 basepairs, with fragments of roughly 500 basepairs being preferred in some embodiments. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others.

As is outlined more fully below, probes (including primers) are made to hybridize to target sequences to determine the presence or absence of the target sequence in a sample. Generally speaking, this term will be understood by those skilled in the art.

The target sequence may also be comprised of different target domains; for example, in "sandwich" type assays as outlined below, a first target domain of the sample target sequence may hybridize to a capture probe or a portion of capture extender probe, a second target domain may hybridize to a portion of an amplifier probe, a label probe, or a different capture or capture extender probe, etc. In addition, the target domains may be adjacent (i.e. contiguous) or separated. For example, when ligation chain reaction (LCR) techniques are used, a first primer may hybridize to a first target domain and a second primer may hybridize to a second target domain; either the domains are adjacent, or they may be separated by one or more nucleotides, coupled with the use of a polymerase and dNTPs, as is more fully outlined below.

The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

In a preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenytoin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g. respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus); hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (PA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-a and TGF-(3), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone and testosterone; and (4) other proteins (including a-fetoprotein, carcinoembryonic antigen CEA, cancer markers, etc.).

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), prostate cancer (PSA), CEA, and colorectal and pancreatic cancer (CA 19, CA 50, CA242).

Suitable target analytes include metal ions, particularly heavy and/or toxic metals, including but not limited to, aluminum, arsenic, cadmium, selenium, cobalt, copper, chromium, lead, silver and nickel.

These target analytes may be present in any number of different sample types, including, but not limited to, bodily fluids including blood, lymph, saliva, vaginal and anal secretions, urine, feces, perspiration and tears, and solid tissues, including liver, spleen, bone marrow, lung, muscle, brain, etc.

Accordingly, the present invention provides microfluidic devices for the detection of target analytes comprising a solid substrate. The solid substrate can be made of a wide variety of materials and can be configured in a large number of ways, as is discussed herein and will be apparent to one of skill in the art. In addition, a single device may be comprises of more than one substrate; for example, there may be a "sample treatment" cassette that interfaces with a separate "detection" cassette; a raw sample is added to the sample treatment cassette and is manipulated to prepare the sample for detection, which is removed from the sample treatment cassette and added to the detection cassette. There may be an additional functional cassette into which the device fits; for example, a heating element which is placed in contact with the sample cassette to effect reactions such as PCR. In some cases, a portion of the substrate may be removable; for example, the sample cassette may have a detachable detection cassette, such that the entire sample cassette is not contacted with the detection apparatus. See for example U.S. Pat. No. 5,603,351 and PCT US96/17116, hereby incorporated by reference.

The composition of the solid substrate will depend on a variety of factors, including the techniques used to create the device, the use of the device, the composition of the sample, the analyte to be detected, the size of the wells and microchannels, the presence or absence of electronic components, etc. Generally, the devices of the invention should be easily sterilizable as well.

In a preferred embodiment, the solid substrate can be made from a wide variety of materials, including, but not limited to, silicon such as silicon wafers, silicon dioxide, silicon nitride, glass and fused silica, gallium arsenide, indium phosphide, aluminum, ceramics, polyimide, quartz, plastics, resins and polymers including polymethylmethacrylate, acrylics, polyethylene, polyethylene terepthalate, polycarbonate, polystyrene and other styrene copolymers, polypropylene, polytetrafluoroethylene, superalloys, zircaloy, steel, gold, silver, copper, tungsten, molybdeumn, tantalum, KOVAR, KEVLAR, KAPTON, MYLAR, brass, sapphire, etc. High quality glasses such as high melting borosilicate or fused silicas may be preferred for their UV transmission properties when any of the sample manipulation steps require light based technologies. In addition, as outlined herein, portions of the internal surfaces of the device may be coated with a variety of coatings as needed, to reduce nonspecific binding, to allow the attachment of binding ligands, for biocompatibility, for flow resistance, etc.

The devices of the invention can be made in a variety of ways, as will be appreciated by those in the art. See for example WO96/39260, directed to the formation of fluid-tight electrical conduits; U.S. Pat. No. 5,747,169, directed to sealing; EP 0637996 131; EP 0637998 131; WO96/39260; WO97/16835; WO98/13683; WO97/16561; WO97/43629; WO96/39252; WO96/15576; WO96/15450; WO97/37755; and WO97/27324; and U.S. Pat. Nos. 5,304,487; 5,071,531; 5,061,336; 5,747,169; 5,296,375; 5,110,745; 5,587,128; 5,498,392; 5,643,738; 5,750,015; 5,726,026; 5,35,358; 5,126,022; 5,770,029; 5,631,337; 5,569,364; 5,135,627; 5,632,876; 5,593,838; 5,585,069; 5,637,469; 5,486,335; 5,755,942; 5,681,484; and 5,603,351, all of which are hereby incorporated by reference. Suitable fabrication techniques again will depend on the choice of substrate, but preferred methods include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding and bonding techniques (see U.S. Pat. No. 5,747,169, hereby incorporated by reference). In addition, there are printing techniques for the creation of desired fluid guiding pathways; that is, patterns of printed material can permit directional fluid transport. Thus, the build-up of "ink" can serve to define a flow channel. In addition, the use of different "inks" or "pastes" can allow different portions of the pathways having different flow properties. For example, materials can be used to change solute/solvent RF values (the ratio of the distance moved by a particular solute to that moved by a solvent front). For example, printed fluid guiding pathways can be manufactured with a printed layer or layers comprised of two different materials, providing different rates of fluid transport. Multi-material fluid guiding pathways can be used when it is desirable to modify retention times of reagents in fluid guiding pathways. Furthermore, printed fluid guiding pathways can also provide regions containing reagent substances, by including the reagents in the "inks" or by a subsequent printing step. See for example U.S. Pat. No. 5,795,453, herein incorporated by reference in its entirety.

In a preferred embodiment, the solid substrate is configured for handling a single sample that may contain a plurality of target analytes. That is, a single sample is added to the device and the sample may either be aliquoted for parallel processing for detection of the analytes or the sample may be processed serially, with individual targets being detected in a serial fashion. In addition, samples may be removed periodically or from different locations for in line sampling.

In a preferred embodiment, the solid substrate is configured for handling multiple samples, each of which may contain one or more target analytes. In general, in this embodiment, each sample is handled individually; that is, the manipulations and analyses are done in parallel, with preferably no contact or contamination between them. Alternatively, there may be some steps in common; for example, it may be desirable to process different samples separately but detect all of the target analytes on a single detection electrode, as described below.

In addition, it should be understood that while most of the discussion herein is directed to the use of planar substrates with microchannels and wells, other geometries can be used as well. For example, two or more planar substrates can be stacked to produce a three dimensional device, that can contain microchannels flowing within one plane or between planes; similarly, wells may span two or more substrates to allow for larger sample volumes. Thus for example, both sides of a substrate can be etched to contain microchannels; see for example U.S. Pat. Nos. 5,603,351 and 5,681,484, both of which are hereby incorporated by reference.

Thus, the devices of the invention include at least one microchannel or flow channel that allows the flow of sample from the sample inlet port to the other components or modules of the system. The collection of microchannels and wells is sometimes referred to in the art as a "mesoscale flow system". As will be appreciated by those in the art, the flow channels may be configured in a wide variety of ways, depending on the use of the channel. For example, a single flow channel starting at the sample inlet port may be separated into a variety of smaller channels, such that the original sample is divided into discrete subsamples for parallel processing or analysis. Alternatively, several flow channels from different modules, for example the sample inlet port and a reagent storage module may feed together into a mixing chamber or a reaction chamber. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer and sometimes tortuous flow channels can be used.

In general, the microfluidic devices of the invention are generally referred to as "mesoscale" devices. The devices herein are typically designed on a scale suitable to analyze microvolumes, although in some embodiments large samples (e.g. cc's of sample) may be reduced in the device to a small volume for subsequent analysis. That is, "mesoscale" as used herein refers to chambers and microchannels that have cross-sectional dimensions on the order of 0.1 µm to 500 µm. The mesoscale flow channels and wells have preferred depths on the order of 0.1 µm to 100 µm, typically 2-50 µm. The channels have preferred widths on the order of 2.0 to 500 µm, more preferably 3-100 µm. For many applications, channels of 5-50 µm are useful. However, for many applications, larger dimensions on the scale of millimeters may be used. Similarly, chambers (sometimes also referred to herein as "wells") in the substrates often will have larger dimensions, on the scale of a few millimeters.

In addition to the flow channel system, the devices of the invention are configured to include one or more of a variety of components, herein referred to as "modules", that will be present on any given device depending on its use. These modules include, but are not limited to: sample inlet ports; sample introduction or collection modules; cell handling modules (for example, for cell lysis, cell removal, cell concentration, cell separation or capture, cell growth, etc.); separation modules, for example, for electrophoresis, dielectrophoresis, gel filtration, ion exchange/affinity chromatography (capture and release) etc.; reaction modules for chemical or biological alteration of the sample, including amplification of the target analyte (for example, when the target analyte is nucleic acid, amplification techniques are useful, including, but not limited to polymerase chain reaction (PCR), ligase chain reaction (LCR), strand displacement amplification (SDA), and nucleic acid sequence based amplification (NASBA)), chemical, physical or enzymatic cleavage or alteration of the target analyte, or chemical modification of the target; fluid pumps; fluid valves; thermal modules for heating and cooling; storage modules for assay reagents; mixing chambers; and detection modules.

In a preferred embodiment, the devices of the invention include at least one sample inlet port for the introduction of the sample to the device. This may be part of or separate from a sample introduction or collection module; that is, the sample may be directly fed in from the sample inlet port to a separation chamber, or it may be pretreated in a sample collection well or chamber.

In a preferred embodiment, the devices of the invention include a sample collection module, which can be used to concentrate or enrich the sample if required; for example, see U.S. Pat. No. 5,770,029, including the discussion of enrichment channels and enrichment means.

In a preferred embodiment, the devices of the invention include a cell handling module. This is of particular use when the sample comprises cells that either contain the target analyte or that must be removed in order to detect the target analyte. Thus, for example, the detection of particular antibodies in blood can require the removal of the blood cells for efficient analysis, or the cells (and/or nucleus) must be lysed prior to detection. In this context, "cells" include eukaryotic and prokaryotic cells, and viral particles that may require treatment prior to analysis, such as the release of nucleic acid from a viral particle prior to detection of target sequences. In addition, cell handling modules may also utilize a downstream means for determining the presence or absence of cells. Suitable cell handling modules include, but are not limited to, cell lysis modules, cell removal modules, cell concentration modules, and cell separation or capture modules. In addition, as for all the modules of the invention, the cell handling module is in fluid communication via a flow channel with at least one other module of the invention.

In a preferred embodiment, the cell handling module includes a cell lysis module. As is known in the art, cells may be lysed in a variety of ways, depending on the cell type. In one embodiment, as described in EP 0 637 998 B1 and U.S. Pat. No. 5,635,358, hereby incorporated by reference, the cell lysis module may comprise cell membrane piercing protrusions that extend from a surface of the cell handling module. As fluid is forced through the device, the cells are ruptured. Similarly, this may be accomplished using sharp edged particles trapped within the cell handling region. Alternatively, the cell lysis module can comprise a region of restricted cross-sectional dimension, which results in cell lysis upon pressure.

In a preferred embodiment, the cell lysis module comprises a cell lysing agent, such as guanidium chloride, chaotropic salts, enzymes such as lysozymes, etc. In some embodiments, for example for blood cells, a simple dilution with water or buffer can result in hypotonic lysis. The lysis agent may be solution form, stored within the cell lysis module or in a storage module and pumped into the lysis module. Alternatively, the lysis agent may be in solid form, that is taken up in solution upon introduction of the sample.

The cell lysis module may also include, either internally or externally, a filtering module for the removal of cellular debris as needed. This filter may be microfabricated between the cell lysis module and the subsequent module to enable the removal of the lysed cell membrane and other cellular debris components; examples of suitable filters are shown in EP 0 637 998 B1, incorporated by reference.

In a preferred embodiment, the cell handling module includes a cell separation or capture module. This embodiment utilizes a cell capture region comprising binding sites capable of reversibly binding a cell surface molecule to enable the selective isolation (or removal) of a particular type of cell from the sample population, for example, white blood cells for the analysis of chromosomal nucleic acid, or subsets of white blood cells. These binding moieties may be immobilized either on the surface of the module or on a particle trapped within the module (i.e. a bead) by physical absorption or by covalent attachment. Suitable binding moieties will depend on the cell type to be isolated or removed, and generally includes antibodies and other binding ligands, such as ligands for cell surface receptors, etc.

Thus, a particular cell type may be removed from a sample prior to further handling, or the assay is designed to specifically bind the desired cell type, wash away the non-desirable cell types, followed by either release of the bound cells by the addition of reagents or solvents, physical removal (i.e. higher flow rates or pressures), or even in situ lysis.

Alternatively, a cellular "sieve" can be used to separate cells on the basis of size. This can be done in a variety of ways, including protrusions from the surface that allow size exclusion, a series of narrowing channels, a weir, or a diafiltration type setup.

In a preferred embodiment, the cell handling module includes a cell removal module. This may be used when the sample contains cells that are not required in the assay or are undesirable. Generally, cell removal will be done on the basis of size exclusion as for "sieving", above, with channels exiting the cell handling module that are too small for the cells.

In a preferred embodiment, the cell handling module includes a cell concentration module. As will be appreciated by those in the art, this is done using "sieving" methods, for example to concentrate the cells from a large volume of sample fluid prior to lysis.

In a preferred embodiment, the devices of the invention include a separation module. Separation in this context means that at least one component of the sample is separated from other components of the sample. This can comprise the separation or isolation of the target analyte, or the removal of contaminants that interfere with the analysis of the target analyte, depending on the assay.

In a preferred embodiment, the separation module includes chromatographic-type separation media such as absorptive phase materials, including, but not limited to reverse phase materials (e.g. $C_8$ or $C_{18}$ coated particles, etc.), ion-exchange materials, affinity chromatography materials such as binding ligands, etc. See U.S. Pat. No. 5,770,029, herein incorporated by reference.

In a preferred embodiment, the separation module utilizes binding ligands, as is generally outlined herein for cell separation or analyte detection. In this embodiment, binding ligands are immobilized (again, either by physical absorption or covalent attachment, described below) within the separation module (again, either on the internal surface of the module, on a particle such as a bead, filament or capillary trapped within the module, for example through the use of a frit). Suitable binding moieties will depend on the sample component to be isolated or removed. By "binding ligand" or grammatical equivalents herein is meant a compound that is used to bind a component of the sample, either a contaminant (for removal) or the target analyte (for enrichment).

In some embodiments, as outlined below, for binding ligand is used to probe for the presence of the target analyte, and that will bind to the analyte.

As will be appreciate by those in the art, the composition of the binding ligand will depend on the sample component to be separated. Binding ligands for a wide variety of analytes are known or can be readily found using known techniques. For example, when the component is a protein, the binding ligands include proteins (particularly including antibodies or fragments thereof (FAbs, etc.)) or small molecules. When the sample component is a metal ion, the binding ligand generally comprises traditional metal ion ligands or chelators. Preferred binding ligand proteins include peptides. For example, when the component is an enzyme, suitable binding ligands include substrates and inhibitors. Antigen-antibody pairs, receptor-ligands, and carbohydrates and their binding partners are also suitable component-binding ligand pairs. The binding ligand may be nucleic acid, when nucleic acid binding proteins are the targets; alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptomers" can be developed for binding to virtually any target analyte. Similarly, there is a wide body of literature relating to the development of binding partners based on combinatorial chemistry methods. In this embodiment, when the binding ligand is a nucleic acid, preferred compositions and techniques are outlined in PCT US97/20014, hereby incorporated by reference.

In a preferred embodiment, the binding of the sample component to the binding ligand is specific, and the binding ligand is part of a binding pair. By "specifically bind" herein is meant that the ligand binds the component, for example the target analyte, with specificity sufficient to differentiate between the analyte and other components or contaminants of the test sample. The binding should be sufficient to remain bound under the conditions of the separation step or assay, including wash steps to remove non-specific binding. In some embodiments, for example in the detection of certain biomolecules, the disassociation constants of the analyte to the binding ligand will be less than about $10^{-4}$-$10^{-6}$ M$^{-1}$, with less than about $10^{-5}$ to $10^{-9}$ M$^{-1}$ being preferred and less than about $10^{-7}$-$10^{-9}$ M$^{-1}$ being particularly preferred.

As will be appreciated by those in the art, the composition of the binding ligand will depend on the composition of the target analyte. Binding ligands to a wide variety of analytes are known or can be readily found using known techniques. For example, when the analyte is a single-stranded nucleic acid, the binding ligand is generally a substantially complementary nucleic acid. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins or small molecules. Preferred binding ligand proteins include peptides. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences. In a preferred embodiment, the binding ligands are portions (particularly the extracellular portions) of cell surface receptors that are known to multimerize, such as the growth hormone receptor, glucose transporters (particularly GLUT4 receptor), transferrin receptor, epidermal growth factor receptor, low density lipoprotein receptor, high density lipoprotein receptor, leptin receptor, interleukin receptors including IL1, IL-2, IL-3, IL-4, IL-5, IL-6, IL-7, IL-8, IL-9, IL-11, IL-12, IL-13, IL-15 and IL-17 receptors, VEGF receptor, PDGF receptor, EPO receptor, TPO receptor, ciliary neurotrophic factor receptor, prolactin receptor, and T-cell receptors.

When the sample component bound by the binding ligand is the target analyte, it may be released for detection purposes if necessary, using any number of known techniques, depending on the strength of the binding interaction, including changes in pH, salt concentration, temperature, etc. or the addition of competing ligands, detergents, chaotropic agents, organic compounds, or solvents, etc.

In some embodiments, preferential binding of molecules to surfaces can be achieved using coating agents or buffer conditions; for example, DNA and RNA may be differentially bound to glass surfaces depending on the conditions.

In a preferred embodiment, the separation module includes an electrophoresis module, as is generally described in U.S. Pat. Nos. 5,770,029; 5,126,022; 5,631,337; 5,569,364; 5,750,015, and 5,135,627, all of which are hereby incorporated by reference. In electrophoresis, molecules are primarily separated by different electrophoretic mobilities caused by their different molecular size, shape and/or charge. Microcapillary tubes have recently been used for use in microcapillary gel electrophoresis (high performance capillary electrophoresis (HPCE)). One advantage of HPCE is that the heat resulting from the applied electric field is efficiently dissipated due to the high surface area, thus allowing fast separation. The electrophoresis module serves to separate sample components by the application of an electric field, with the movement of the sample components being due either to their charge or, depending on the surface chemistry of the microchannel, bulk fluid flow as a result of electroosmotic flow (EOF).

As will be appreciated by those in the art, the electrophoresis module can take on a variety of forms, and generally comprises an electrophoretic microchannel and associated electrodes to apply an electric field to the electrophoretic microchannel. Waste fluid outlets and fluid reservoirs are present as required.

The electrodes comprise pairs of electrodes, either a single pair, or, as described in U.S. Pat. Nos. 5,126,022 and 5,750,015, a plurality of pairs. Single pairs generally have one electrode at each end of the electrophoretic pathway. Multiple electrode pairs may be used to precisely control the movement of sample components, such that the sample components may be continuously subjected to a plurality of electric fields either simultaneously or sequentially.

In a preferred embodiment, electrophoretic gel media may also be used. By varying the pore size of the media, employing two or more gel media of different porosity, and/or providing a pore size gradient, separation of sample components can be maximized. Gel media for separation based on size are known, and include, but are not limited to, polyacrylamide and agarose. One preferred electrophoretic separation matrix is described in U.S. Pat. No. 5,135,627, hereby incorporated by reference, that describes the use of "mosaic matrix", formed by polymerizing a dispersion of microdomains ("dispersoids") and a polymeric matrix. This allows enhanced separation of target analytes, particularly nucleic acids. Similarly, U.S. Pat. No. 5,569,364, hereby incorporated by reference, describes separation media for electrophoresis comprising submicron to above-micron sized crosslinked gel particles that find use in microfluidic systems. U.S. Pat. No. 5,631,337, hereby incorporated by reference, describes the use of thermoreversible hydrogels comprising polyacrylamide backbones with N-substituents that serve to provide hydrogen bonding groups for improved electrophoretic separation. See also U.S. Pat. Nos. 5,061,336 and 5,071,531, directed to methods of casting gels in capillary tubes.

In a preferred embodiment, the devices of the invention include a reaction module. This can include either physical, chemical or biological alteration of one or more sample components. Alternatively, it may include a reaction module wherein the target analyte alters a second moiety that can then be detected; for example, if the target analyte is an enzyme, the reaction chamber may comprise an enzyme substrate that upon modification by the target analyte, can then be detected. In this embodiment, the reaction module may contain the necessary reagents, or they may be stored in a storage module and pumped as outlined herein to the reaction module as needed.

In a preferred embodiment, the reaction module includes a chamber for the chemical modification of all or part of the sample. For example, chemical cleavage of sample components (CNBr cleavage of proteins, etc.) or chemical cross-linking can be done. PCT US97/07880, hereby incorporated by lists a large number of possible chemical reactions that can be done in the devices of the invention, including amide formation, acylation, alkylation, reductive amination, Mitsunobu, Diels Alder and Mannich reactions, Suzuki and Stille coupling, chemical labeling, etc. Similarly, U.S. Pat. Nos. 5,616,464 and 5,767,259 describe a variation of LCR that utilizes a "chemical ligation" of sorts. In this embodiment, similar to LCR, a pair of primers are utilized, wherein the first primer is substantially complementary to a first domain of the target and the second primer is substantially complementary t an adjacent second domain of the target (although, as for LCR, if a "gap" exists, a polymerase and dNTPs may be added to "fill in" the gap). Each primer has a portion that acts as a "side chain" that does not bind the target sequence and acts as one half of a stem structure that interacts noncovalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, can also form side chain hybridization complexes. At least one of the side chains of the primers comprises an activatable cross-linking agent, generally covalently attached to the side chain, that upon activation, results in a chemical cross-link or chemical ligation. The activatible group may comprise any moiety that will allo cross-linking of the side chains, and include groups activated chemically, photonically and thermally, with photo-activatable groups being preferred. In some embodiments a single activatable group on on of the side chains is enough to result in cross-linking via interaction to a functional group on the other side chain; in alternate embodiments, activatable groups are required on each side chain. In addition, the reaction chamber may contain chemical moieties for the protection or deprotection of certain functional groups, such as thiols or amines.

In a preferred embodiment, the reaction module includes a chamber for the biological alteration of all or part of the sample. For example, enzymatic processes including nucleic acid amplification, hydrolysis of sample components or the hydrolysis of substrates by a target enzyme, the addition or removal of detectable labels, the addition or removal of phosphate groups, etc.

In a preferred embodiment, the target analyte is a nucleic acid and the biological reaction chamber allows amplification of the target nucleic acid. Suitable amplification techniques include, both target amplification and probe amplification, including, but not limited to, polymerase chain reaction (PCR), ligase chain reaction (LCR), strand displacement amplification (SDA), self-sustained sequence replication (3SR), QB replicase amplification (QBR), repair chain reaction (RCR), cycling probe technology or reaction (CPT or CPR), and nucleic acid sequence based amplification (NASBA). Techniques utilizing these methods and the detection modules of the invention are described in PCT US99/01705, herein incorporated by reference in its entirety. In this embodiment, the reaction reagents generally comprise at least one enzyme (generally polymerase), primers, and nucleoside triphosphates as needed.

General techniques for nucleic acid amplification are discussed below. In most cases, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques such as the use of extra probes or nucleic acid binding proteins may also be used.

A probe nucleic acid (also referred to herein as a primer nucleic acid) is then contacted to the target sequence to form a hybridization complex. By "primer nucleic acid" herein is meant a probe nucleic acid that will hybridize to some portion, i.e. a domain, of the target sequence. Probes of the present invention are designed to be complementary to a target sequence (either the target sequence of the sample or to other probe sequences, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide. The hybridization conditions may also vary when a non-ionic backbone, i.e. PNA is used, as is known in the art. In addition, crosslinking agents may be added after target binding to cross-link, i.e. covalently attach, the two strands of the hybridization complex.

Thus, the assays are generally run under stringency conditions which allows formation of the hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency Conditions to reduce non-specific binding.

The size of the primer nucleic acid may vary, as will be appreciated by those in the art, in general varying from 5 to 500 nucleotides in length, with primers of between 10 and 100 being preferred, between 15 and 50 being particularly preferred, and from 10 to 35 being especially preferred, depending on the use and amplification technique.

In addition, the different amplification techniques may have further requirements of the primers, as is more fully described below.

Once the hybridization complex between the primer and the target sequence has been formed, an enzyme, sometimes termed an "amplification enzyme", is used to modify the primer. As for all the methods outlined herein, the enzymes may be added at any point during the assay, either prior to, during, or after the addition of the primers. The identification of the enzyme will depend on the amplification technique used, as is more fully outlined below. Similarly, the modification will depend on the amplification technique, as outlined below, although generally the first step of all the reactions herein is an extension of the primer, that is, nucleotides are added to the primer to extend its length.

Once the enzyme has modified the primer to form a modified primer, the hybridization complex is disassociated. Generally, the amplification steps are repeated for a period of time to allow a number of cycles, depending on the number of copies of the original target sequence and the sensitivity of detection, with cycles ranging from 1 to thousands, with from 10 to 100 cycles being preferred and from 20 to 50 cycles being especially preferred.

After a suitable time or amplification, the modified primer is moved to a detection module and incorporated into an assay complex, as is more fully outlined below. The assay complex is covalently attached to an electrode, and comprises at least one electron transfer moiety (ETM), described below. Electron transfer between the ETM and the electrode is then detected to indicate the presence or absence of the original target sequence, as described below.

In a preferred embodiment, the amplification is target amplification. Target amplification involves the amplification (replication) of the target sequence to be detected, such that the number of copies of the target sequence is increased. Suitable target amplification techniques include, but are not limited to, the polymerase chain reaction (PCR), strand displacement amplification (SDA), and nucleic acid sequence based amplification (NASBA).

In a preferred embodiment, the target amplification technique is PCR. The polymerase chain reaction (PCR) is widely used and described, and involve the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR". "panhandle PCR", and "PCR select cDNA subtraction", among others.

In general, PCR may be briefly described as follows. A double stranded target nucleic acid is denatured, generally by raising the temperature, and then cooled in the presence of an excess of a PCR primer, which then hybridizes to the first target strand. A DNA polymerase then acts to extend the primer, resulting in the synthesis of a new strand forming a hybridization complex. The sample is then heated again, to disassociate the hybridization complex, and the process is repeated. By using a second PCR primer for the complementary target strand, rapid and exponential amplification occurs. Thus PCR steps are denaturation, annealing and extension. The particulars of PCR are well known, and include the use of a thermostabile polymerase such as Taq I polymerase and thermal cycling.

Accordingly, the PCR reaction requires at least one PCR primer and a polymerase. Mesoscale PCR devices are described in U.S. Pat. Nos. 5,498,392 and 5,587,128, and WO 97/16561, incorporated by reference.

In a preferred embodiment, the target amplification technique is SDA. Strand displacement amplification (SDA) is generally described in Walker et al., in Molecular Methods for Virus Detection, Academic Press, Inc., 1995; and U.S. Pat. Nos. 5,455,166 and 5,130,238, all of which are hereby expressly incorporated by reference in their entirety.

In general, SDA may be described as follows. A single stranded target nucleic acid, usually a DNA target sequence, is contacted with an SDA primer. An "SDA primer" generally has a length of 25-100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease", as outlined below. The SDA primer then hybridizes to the target sequence. The SDA reaction mixture also contains a polymerase (an "SDA polymerase", as outlined below) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2'deoxyadenosine 5'-O-(1-thiotriphosphate), 5-methyldeoxycytidine 5'-triphosphate, 2'-deoxyuridine 5'-triphosphate, and 7-deaza-2'-deoxyguanosine 5'-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'→3' exonuclease activity. However, if less than all the nucleotides are substituted, the polymerase preferably lacks 5'→3' exonuclease activity.

As will be appreciated by those in the art, the recognition sitelendonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincII, HindII, AvaI, Fnu4HI, TthIIII, NcII, BstXI, BamI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5'→3', thereby creating another newly synthesized strand. The polymerase chosen should be able to initiate 5'→3' polymerization at a nick site, should also displace the polymerized strand downstream from the nick, and should lack 5'→ 3' exonuclease activity (this may be additionally accomplished by the addition of a blocking agent). Thus, suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

Accordingly, the SDA reaction requires, in no particular order, an SDA primer, an SDA polymerase, a nicking endonuclease, and dNTPs, at least one species of which is modified.

In general, SDA does not require thermocycling. The temperature of the reaction is generally set to be high enough to prevent non-specific hybridization but low enough to allow specific hybridization; this is generally from about 37° C. to about 42° C., depending on the enzymes.

In a preferred embodiment, as for most of the amplification techniques described herein, a second amplification reaction can be done using the complementary target sequence, resulting in a substantial increase in amplification during a set period of time. That is, a second primer nucleic acid is hybridized to a second target sequence, that is substantially complementary to the first target sequence, to form a second hybridization complex. The addition of the enzyme, followed by disassociation of the second hybridization complex, results in the generation of a number of newly synthesized second strands.

In this way, a number of target molecules are made, and transferred to a detection module, described below. As is more fully outlined below, these reactions (that is, the products of these reactions) can be detected in a number of ways. In general, either direct or indirect detection of the target products can be done. "Direct" detection as used in this context, as for the other amplification strategies outlined herein, requires the incorporation of a label, in this case an electron transfer moiety (ETM), into the target sequence, with detection proceeding according to either "mechanism-1" or "mechanism-2", outlined below. In this embodiment, the ETM(s) may be incorporated in three ways: (1) the primers comprise the ETM(s), for example attached to the base, a ribose, a phosphate, or to analogous structures in a nucleic acid analog; (2) modified nucleosides are used that are modified at either the base or the ribose (or to analogous structures in a nucleic acid analog) with the ETM(s); these ETM modified nucleosides are then converted to the triphosphate form and are incorporated into the newly synthesized strand by a polymerase; or (3) a "tail" of ETMs can be added, as outlined below. Either of these methods result in a newly synthesized strand that comprises ETMs, that can be directly detected as outlined below.

Alternatively, indirect detection proceeds as a sandwich assay, with the newly synthesized strands containing few or no ETMs. Detection then proceeds via the use of label probes that comprise the ETM(s); these label probes will hybridize either directly to the newly synthesized strand or to intermediate probes such as amplification probes, as is more fully outlined below. In this case, it is the ETMs on the label probes that are used for detection as outlined below.

In a preferred embodiment, the target amplification technique is nucleic acid sequence based amplification (NASBA). NASBA is generally described in U.S. Pat. No. 5,409,818 and "Profiting from Gene-based Diagnostics", CTB International Publishing Inc., N.J., 1996, both of which are expressly incorporated by reference in their entirety.

In general, NASBA may be described as follows. A single stranded target nucleic acid, usually an RNA target sequence (sometimes referred to herein as "the first target sequence" or "the first template"), is contacted with a first NASBA primer. A "NASBA primer" generally has a length of 25100 nucleotides, with NASBA primers of approximately 50-75 nucleotides being preferred. The first NASBA primer is preferably a DNA primer that has at its 3' end a sequence that is substantially complementary to the Tend of the first template. The first NASBA primer has an RNA polymerase promoter at its Fend. The first NASBA primer is then hybridized to the first template to form a first hybridization complex. The NASBA reaction mixture also includes a reverse transcriptase enzyme (an "NASBA reverse transcriptase") and a mixture of the four dNTPs, such that the first NASBA primer is modified, i.e. extended, to form a modified first primer, comprising a hybridization complex of RNA (the first template) and DNA (the newly synthesized strand).

By "reverse transcriptase" or "RNA-directed DNA polymerase" herein is meant an enzyme capable of synthesizing DNA from a DNA primer and an RNA template. Suitable RNA-directed DNA polymerases include, but are not limited to, avian myloblastosis virus reverse transcriptase ("AMV RT") and the Moloney murine leukemia virus RT.

In addition to the components listed above, the NASBA reaction also includes an RNA degrading enzyme, also sometimes referred to herein as a ribonuclease, that will hydrolyze RNA of an RNA:DNA hybrid without hydrolyzing single- or double-stranded RNA or DNA. Suitable ribonucleases include, but are not limited to, RNase H from E. coli and calf thymus.

The ribonuclease degrades the first RNA template in the hybridization complex, resulting in a disassociation of the hybridization complex leaving a first single stranded newly synthesized DNA strand, sometimes referred to herein as "the second template".

In addition, the NASBA reaction also includes a second NASBA primer, generally comprising DNA (although as for all the probes herein, including primers, nucleic acid analogs may also be used). This second NASBA primer has a sequence at its 3' end that is substantially complementary to the Tend of the second template, and also contains an antisense sequence for a functional promoter and the antisense sequence of a transcription initiation site. Thus, this primer sequence, when used as a template for synthesis of the third DNA template, contains sufficient information to allow specific and efficient binding of an RNA polymerase and initiation of transcription at the desired site. Preferred embodiments utilizes the antisense promoter and transcription initiation site are that of the T7 RNA polymerase, although other RNA polymerase promoters and initiation sites can be used as well, as outlined below.

The second primer hybridizes to the second template, and a DNA polymerase, also termed a "DNA-directed DNA polymerase", also present in the reaction, synthesizes a third template (a second newly synthesized DNA strand), resulting in second hybridization complex comprising two newly synthesized DNA strands.

Finally, the inclusion of an RNA polymerase and the required four ribonucleoside triphosphates (ribonucleotides or NTPs) results in the synthesis of an RNA strand (a third newly synthesized strand that is essentially the same as the first template). The RNA polymerase, sometimes referred to herein as a "DNA-directed RNA polymerase", recognizes the promoter and specifically initiates RNA synthesis at the initiation site. In addition, the RNA polymerase preferably synthesizes several copies of RNA per DNA duplex. Preferred RNA polymerases include, but are not limited to, T7 RNA polymerase, and other bacteriophage RNA polymerases including those of phage T3, phage φII, *Salmonella* phage sp6, or Pseudomonase phage gh-1.

Accordingly, the NASBA reaction requires, in no particular order, a first NASBA primer, a second NASBA primer comprising an antisense sequence of an RNA polymerase promoter, an RNA polymerase that recognizes the promoter, a reverse transcriptase, a DNA polymerase, an RNA degrading enzyme, NTPs and dNTPs, in addition to the detection components outlined below.

These components result in a single starting RNA template generating a single DNA duplex; however, since this DNA duplex results in the creation of multiple RNA strands, which can then be used to initiate the reaction again, amplification proceeds rapidly.

As outlined herein, the detection of the newly synthesized strands can proceed in several ways. Direct detection can be done in the detection module when the newly synthesized strands comprise ETM labels, either by incorporation into the primers or by incorporation of modified labelled nucleotides into the growing strand. Alternatively, as is more fully outlined below, indirect detection of unlabelled strands (which now serve as "targets" in the detection mode) can occur using a variety of sandwich assay configurations. As will be appreciated by those in the art, it is preferable to detect DNA strands during NASBA since the presence of the ribonuclease makes the RNA strands potentially labile.

In a preferred embodiment, the amplification technique is signal amplification. Signal amplification involves the use of limited number of target molecules as templates to either generate multiple signalling probes or allow the use of multiple signalling probes. Signal amplification strategies include LCR, CPT, and the use of amplification probes in sandwich assays.

In a preferred embodiment, the signal amplification technique is LCR. The method can be run in two different ways; in a first embodiment, only one strand of a target sequence is used as a template for ligation; alternatively, both strands may be used. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, and U.S. Ser. Nos. 60/078,102 and 60/073,011, all of which are incorporated by reference.

In a preferred embodiment, the single-stranded target sequence comprises a first target domain and a second target domain, and a first LCR primer and a second LCR primer nucleic acids are added, that are substantially complementary to its respective target domain and thus will hybridize to the target domains. These target domains may be directly adjacent, i.e. contiguous, or separated by a number of nucleotides. If they are non-contiguous, nucleotides are added along with means to join nucleotides, such as a polymerase, that will add the nucleotides to one of the primers. The two LCR primers are then covalently attached, for example using a ligase enzyme such as is known in the art. This forms a first hybridization complex comprising the ligated probe and the target sequence. This hybridization complex is then denatured (disassociated), and the process is repeated to generate a pool of ligated probes. In addition, it may be desirable to have the detection probes, described below, comprise a mismatch at the probe junction site, such that the detection probe cannot be used as a template for ligation.

In a preferred embodiment, LCR is done for two strands of a double-stranded target sequence. The target sequence is denatured, and two sets of probes are added: one set as outlined above for one strand of the target, and a separate set (i.e. third and fourth primer robe nucleic acids) for the other strand of the target. In a preferred embodiment, the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

Again, as outlined above, the detection of the LCR reaction can occur directly, in the case where one or both of the primers comprises at least one ETM, or indirectly, using sandwich assays, through the use of additional probes; that is, the ligated probes can serve as target sequences, and detection may utilize amplification probes, capture probes, capture extender probes, label probes, and label extender probes, etc.

In a preferred embodiment, the signal amplification technique is CPT. CPT technology is described in a number of patents and patent applications, including U.S. Pat. Nos. 5,011,769, 5,403,711, 5,660,988, and 4,876,187, and PCT published applications WO 95/05480, WO 95/1416, and WO 95/00667, and U.S. Ser. No. 09/014,304, all of which are expressly incorporated by reference in their entirety.

Generally, CPT may be described as follows. A CPT primer (also sometimes referred to herein as a "scissile primer"), comprises two probe sequences separated by a scissile linkage. The CPT primer is substantially complementary to the target sequence and thus will hybridize to it to form a hybridization complex. The scissile linkage is cleaved, without cleaving the target sequence, resulting in the two probe sequences being separated. The two probe sequences can thus be more easily disassociated from the target, and the reaction can be repeated any number of times. The cleaved primer is then detected as outlined herein.

By "scissile linkage" herein is meant a linkage within the scissile probe that can be cleaved when the probe is part of a hybridization complex, that is, when a double-stranded complex is formed. It is important that the scissile linkage cleave only the scissile probe and not the sequence to which it is hybridized (i.e. either the target sequence or a probe sequence), such that the target sequence may be reused in the reaction for amplification of the signal. As used herein, the scissile linkage, is any connecting chemical structure which joins two probe sequences and which is capable of being selectively cleaved without cleavage of either the probe sequences or the sequence to which the scissile probe is hybridized. The scissile linkage may be a single bond, or a multiple unit sequence. As will be appreciated by those in the art, a number of possible scissile linkages may be used.

In a preferred embodiment, the scissile linkage comprises RNA. This system, previously described in as outlined above, is based on the fact that certain double-stranded nucleases, particularly ribonucleases, will nick or excise RNA nucleosides from a RNA:DNA hybridization complex. Of particular use in this embodiment is RNAseH, Exo III, and reverse transcriptase.

In one embodiment, the entire scissile probe is made of RNA, the nicking is facilitated especially when carried out with a double-stranded ribonuclease, such as RNAseH or Exo III. RNA probes made entirely of RNA sequences are particularly useful because first, they can be more easily produced enzymatically, and second, they have more cleavage sites which are accessible to nicking or cleaving by a nicking agent, such as the ribonucleases. Thus, scissile probes made entirely of RNA do not rely on a scissile linkage since the scissile linkage is inherent in the probe.

In a preferred embodiment, when the scissile linkage is a nucleic acid such as RNA, the methods of the invention may be used to detect mismatches, as is generally described in U.S. Pat. No. 5,660,988, and WO 95/14106, hereby expressly incorporated by reference. These mismatch detection methods are based on the fact that RNAseH may not bind to and/or cleave an RNA:DNA duplex if there are mismatches present in the sequence. Thus, in the $NA_1$-R-$NA_2$ embodiments, $NA_1$, and $NA_2$ are non-RNA nucleic acids, preferably DNA. Preferably, the mismatch is within the RNA:DNA duplex, but in some embodiments the mismatch is present in an adjacent sequence very close to the desired sequence, close enough to affect the RNAseH (generally within one or two bases). Thus, in this embodiment, the nucleic acid scissile linkage is designed such that the sequence of the scissile linkage reflects the particular sequence to be detected, i.e. the area of the putative mismatch.

In some embodiments of mismatch detection, the rate of generation of the released fragments is such that the methods provide, essentially, a yes/no result, whereby the detection of the virtually any released fragment indicates the presence of the desired target sequence. Typically, however, when there is only a minimal mismatch (for example, a 1-, 2- or 3-base mismatch, or a 3-base detection), there is some generation of cleaved sequences even though the target sequence is not present. Thus, the rate of generation of cleaved fragments, and/or the final amount of cleaved fragments, is quantified to indicate the presence or absence of the target. In addition, the use of secondary and tertiary scissile probes may be particularly useful in this embodiment, as this can amplify the differences between a perfect match and a mismatch. These methods may be particularly useful in the determination of homozygotic or heterozygotic states of a patient.

In this embodiment, it is an important feature of the scissile linkage that its length is determined by the suspected difference between the target and the probe. In particular, this means that the scissile linkage must be of sufficient length to encompass the suspected difference, yet short enough the scissile linkage cannot inappropriately "specifically hybridize" to the selected nucleic acid molecule when the suspected difference is present; such inappropriate hybridization would permit excision and thus cleavage of scissile linkages even though the selected nucleic acid molecule was not fully complementary to the nucleic acid probe. Thus in a preferred embodiment, the scissile linkage is between 3 to 5 nucleotides in length, such that a suspected nucleotide difference from 1 nucleotide to 3 nucleotides is encompassed by the scissile linkage, and 0, 1 or 2 nucleotides are on either side of the difference.

Thus, when the scissile linkage is nucleic acid, preferred embodiments utilize from 1 to about 100 nucleotides, with from about 2 to about 20 being preferred and from about 5 to about 10 being particularly preferred.

CPT may be done enzymatically or chemically. That is, in addition to RNAseH, there are several other cleaving agents which may be useful in cleaving RNA (or other nucleic acid) scissile bonds. For example, several chemical nucleases have been reported; see for example Sigman et al., Annu. Rev. Biochem. 1990, 59, 207-236; Sigman et al., Chem. Rev. 1993, 93, 2295-2316; Bashkin et al., J. Org. Chem. 1990, 55, 5125-5132; and Sigman et al., Nucleic Acids and Molecular Biology, vol. 3, F. Eckstein and D. M. J. Lilley (Eds), Springer-Verlag, Heidelberg 1989, pp. 13-27; all of which are hereby expressly incorporated by reference.

Specific RNA hydrolysis is also an active area; see for example Chin, Acc. Chem. Res. 1991, 24, 145152; Breslow et al., Tetrahedron, 1991, 47, 2365-2376; Anslyn et al., Angew. Chem. Int. Ed. Engl., 1997, 36, 432-450; and references therein, all of which are expressly incorporated by reference. Reactive phosphate centers are also of interest in developing scissile linkages, see Hendry et al., Prog. Inorg. Chem.: Bioinorganic Chem. 1990, 31, 201-258 also expressly incorporated by reference.

Current approaches to site-directed RNA hydrolysis include the conjugation of a reactive moiety capable of cleaving phosphodiester bonds to a recognition element capable of sequence-specifically hybridizing to RNA. In most cases, a metal complex is covalently attached to a DNA strand which forms a stable heteroduplex. Upon hybridization, a Lewis acid is placed in close proximity to the RNA backbone to effect hydrolysis; see Magda et al., J. Am. Chem. Soc. 1994, 116, 7439; Hall et al., Chem. Biology 1994, 1, 185-190; Bashkin et al., J. Am. Chem. Soc. 1994, 116, 5981-5982; Hall et al., Nucleic Acids Res. 1996, 24, 3522; Magda et al., J. Am. Chem. Soc. 1997, 119, 2293; and Magda et al., J. Am. Chem. Soc. 1997, 119, 6947, all of which are expressly incorporated by reference.

In a similar fashion, DNA-polyamine conjugates have been demonstrated to induce site-directed RNA strand scission; see for example, Yoshinari et al., J. Am. Chem. Soc. 1991, 113, 5899-5901; Endo et al., J. Org. Chem. 1997, 62, 846; and Barbier et al., J. Am. Chem. Soc. 1992, 114, 3511-3515, all of which are expressly incorporated by reference.

In a preferred embodiment, the scissile linkage is not necessarily RNA. For example, chemical cleavage moieties may be used to cleave basic sites in nucleic acids; see Belmont, et al., New J. Chem. 1997, 21, 47-54; and references therein, all of which are expressly incorporated herein by reference. Similarly, photocleavable moieties, for example, using transition metals, may be used; see Moucheron, et al., Inorg. Chem. 1997, 36, 584-592, hereby expressly by reference.

Other approaches rely on chemical moieties or enzymes; see for example Keck et al., Biochemistry 1995, 34, 12029-12037; Kirk et al., Chem. Commun. 1998, in press; cleavage of G-U basepairs by metal complexes; see Biochemistry, 1992, 31, 5423-5429; diamine complexes for cleavage of RNA; Komiyama, et al., J. Org. Chem. 1997, 62, 2155-2160; and Chow et al., Chem. Rev. 1997, 97, 14891513, and references therein, all of which are expressly incorporated herein by reference.

The first step of the CPT method requires hybridizing a primary scissile primer (also called a primary scissile probe) probe to the target. This is preferably done at a temperature that allows both the binding of the longer primary probe and disassociation of the shorter cleaved portions of the primary probe, as will be appreciated by those in the art. As outlined herein, this may be done in solution, or either the target or one or more of the scissile probes may be attached to a solid support. For example, it is possible to utilize "anchor probes" on a solid support or the electrode which are substantially complementary to a portion of the target sequence, preferably a sequence that is not the same sequence to which a scissile probe will bind.

Similarly, as outlined herein, a preferred embodiment has one or more of the scissile probes attached to a solid support such as a bead. In this embodiment, the soluble target diffuses to allow the formation of the hybridization complex between the soluble target sequence and the support-bound scissile probe. In this embodiment, it may be desirable to include additional scissile linkages in the scissile probes to allow the release of two or more probe sequences, such that more than one probe sequence per scissile probe may be detected, as is outlined below, in the interests of maximizing the signal.

In this embodiment (and in other techniques herein), preferred methods utilize cutting or shearing techniques to cut the nucleic acid sample containing the target sequence into a size that will allow sufficient diffusion of the target sequence to the surface of a bead. This may be accomplished by shearing the nucleic acid through mechanical forces or by cleaving the nucleic acid using restriction endonucleases. Alternatively, a fragment containing the target may be generated using polymerase, primers and the sample as a template, as in polymerase chain reaction (PCR). In addition, amplification of the target using PCR or LCR or related methods may also be done; this may be particularly useful when the target sequence is present in the sample at extremely low copy numbers.

Similarly, numerous techniques are known in the art to increase the rate of mixing and hybridization including agitation, heating, techniques that increase the overall concentration such as precipitation, drying, dialysis, centrifugation, electrophoresis, magnetic bead concentration, etc.

In general, the scissile probes are introduced in a molar excess to their targets (including both the target sequence or other scissile probes, for example when secondary or tertiary scissile probes are used), with ratios of scissile probe:target of at least about 100:1 being preferred, at least about 1000:1 being particularly preferred, and at least about 10,000:1 being especially preferred. In some embodiments the excess of probe:target will be much greater. In addition, ratios such as these may be used for all the amplification techniques outlined herein.

Once the hybridization complex between the primary scissile probe and the target has been formed, the complex is subjected to cleavage conditions. As will be appreciated, this depends on the composition of the scissile probe; if it is RNA, RNAseH is introduced. It should be noted that under certain circumstances, such as is generally outlined in WO 95/00666 and WO 95/00667, hereby incorporated by reference, the use of a double-stranded binding agent such as RNAseH may allow the reaction to proceed even at temperatures above the Tm of the primary probe:target hybridization complex. Accordingly, the addition of scissile probe to the target can be done either first, and then the cleavage agent or cleavage conditions introduced, or the probes may be added in the presence of the cleavage agent or conditions.

The cleavage conditions result in the separation of the two (or more) probe sequences of the primary scissile probe. As a result, the shorter probe sequences will no longer remain hybridized to the target sequence, and thus the hybridization complex will disassociate, leaving the target sequence intact. The optimal temperature for carrying out the CPT reactions is generally from about 5° C. to about 25° C. below the melting temperatures of the probe:target hybridization complex. This provides for a rapid rate of hybridization and high degree of specificity for the target sequence. The Tm of any particular hybridization complex depends on salt concentration, G-C content, and length of the complex, as is known in the art.

During the reaction, as for the other amplification techniques herein, it may be necessary to suppress cleavage of the probe, as well as the target sequence, by nonspecific nucleases. Such nucleases are generally removed from the sample during the isolation of the DNA by heating or extraction procedures. A number of inhibitors of single-stranded nucleases such as vanadate, inhibitors it-ACE and RNAsin, a placental protein, do not affect the activity of RNAseH. This may not be necessary depending on the purity of the RNAseH and/or the target sample.

These steps are repeated by allowing the reaction to proceed for a period of time. The reaction is usually carried out for about 15 minutes to about 1 hour. Generally, each molecule of the target sequence will turnover between 100 and 1000 times in this period, depending on the length and sequence of the probe, the specific reaction conditions, and the cleavage method. For example, for each copy of the target sequence present in the test sample 100 to 1000 molecules will be cleaved by RNAseH. Higher levels of amplification can be obtained by allowing the reaction to proceed longer, or using secondary, tertiary, or quaternary probes, as is outlined herein.

Upon completion of the reaction, generally determined by time or amount of cleavage, the uncleaved scissile probes must be removed or neutralized prior to detection, such that the uncleaved probe does not bind to a detection probe, causing false positive signals. This may be done in a variety of ways, as is generally described below.

In a preferred embodiment, the separation is facilitated by the use of a solid support (either an internal surface of the device or beads trapped in the device) containing the primary probe. Thus, when the scissile probes are attached to the solid support, the flow of the sample past this solid support can result in the removal of the uncleaved probes.

In a preferred embodiment, the separation is based on gel electrophoresis of the reaction products to separate the longer uncleaved probe from the shorter cleaved probe sequences as is known in the art and described herein.

In a preferred embodiment, the separation is based on strong acid precipitation. This is useful to separate long (generally greater than 50 nucleotides) from smaller fragments (generally about 10 nucleotides). The introduction of a strong acid such as trichloroacetic acid into the solution (generally from a storage module) causes the longer probe to precipitate, while the smaller cleaved fragments remain in solution. The use of frits or filters can to remove the precipitate, and the cleaved probe sequences can be quantitated.

In a preferred embodiment, the scissile probe contains both an ETM and an affinity binding ligand or moiety, such that an affinity support is used to carry out the separation. In this embodiment, it is important that the ETM used for detection is not on the same probe sequence that contains the affinity moiety, such that removal of the uncleaved probe, and the cleaved probe containing the affinity moiety, does not remove all the detectable ETMs. Alternatively, the scissile probe may not contain a covalently attached ETM, but just an affinity label. Suitable affinity moieties include, but are not limited to, biotin, avidin, streptavidin, lectins, haptens, antibodies, etc. The binding partner of the affinity moiety is attached to a solid support (again, either an internal surface of the device or to beads trapped within the device) and the flow of the sample past this support is used to pull out the uncleaved probes, as is known in the art. The cleaved probe sequences, which do not contain the affinity moiety, remain in solution and then can be detected as outlined below.

In a preferred embodiment, similar to the above embodiment, a separation sequence of nucleic acid is included in the scissile probe, which is not cleaved during the reaction. A nucleic acid complementary to the separation sequence is attached to a solid support and serves as a catcher sequence. Preferably, the separation sequence is added to the scissile probes, and is not recognized by the target sequence, such that a generalized catcher sequence may be utilized in a variety of assays.

In a preferred embodiment, the uncleaved probe is neutralized by the addition of a substantially complementary neutralization nucleic acid, generally from a storage module. This is particularly useful in embodiments utilizing capture sequences, separation sequences, and one-step systems, as the complement to a probe containing capture sequences forms hybridization complexes that are more stable due to its length than the cleaved probe sequence:detection probe complex. As will be appreciated by those in the art, complete removal of the uncleaved probe is not required, since detection is based on electron transfer through nucleic acid; rather, what is important is that the uncleaved probe is not available for binding to a detection electrode probe specific for cleaved sequences. Thus, in one embodiment, this step occurs in the detection module and the neutralization nucleic acid is a detection probe on the surface of the electrode, at a separate "address", such that the signal from the neutralization hybridization complex does not contribute to the signal of the cleaved fragments. Alternatively, the neutralization nucleic acid may be attached to a solid support; the sample flowed past the neutralization surface to quench the reaction, and thus do not enter the detection module.

After removal or neutralization of the uncleaved probe, detection proceeds via the addition of the cleaved probe sequences to the detection module, as outlined below, which can utilize either "mechanism-1" or "mechanism-2" systems.

In a preferred embodiment, no higher order probes are used, and detection is based on the probe sequence(s) of the primary primer. In a preferred embodiment, at least one, and preferably more, secondary probes (also referred to herein as secondary primers) are used. The secondary scissile probes may be added to the reaction in several ways. It is important that the secondary scissile probes be prevented from hybridizing to the uncleaved primary probes, as this results in the generation of false positive signal. In a preferred embodiment, the primary and secondary probes are bound to solid supports. It is only upon hybridization of the primary probes with the target, resulting in cleavage and release of primary probe sequences from the bead, that the now diffusible primary probe sequences may bind to the secondary probes. In turn, the primary probe sequences serve as targets for the secondary scissile probes, resulting in cleavage and release of secondary probe sequences.

In an alternate embodiment, the complete reaction is done in solution. In this embodiment, the primary probes are added, the reaction is allowed to proceed for some period of time, and the uncleaved primary scissile probes are removed, as outlined above. The secondary probes are then added, and the reaction proceeds. The secondary uncleaved probes are then removed, and the cleaved sequences are detected as is generally outlined herein. In a preferred embodiment, at least one, and preferably more, tertiary probes are used. The tertiary scissile probes may be added to the reaction in several ways. It is important that the tertiary scissile probes be prevented from hybridizing to the uncleaved secondary probes, as this results in the generation of false positive signal. These methods are generally done as outlined above. Similarly, quaternary probes can be used as above.

Thus, CPT requires, again in no particular order, a first CPT primer comprising a first probe sequence, a scissile linkage and a second probe sequence; and a cleavage agent.

In this manner, CPT results in the generation of a large amount of cleaved primers, which then can be detected as outlined below.

In a preferred embodiment, the signal amplification technique is a "sandwich" assay, as is generally described in U.S. Ser. No. 60/073,011 and in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. Although sandwich assays do not result in the alteration of primers, sandwich assays can be considered signal amplification techniques since multiple signals (i.e. label probes) are bound to a single target, resulting in the amplification of the signal. Sandwich assays are used when the target sequence comprises little or no ETM labels; that is, when a secondary probe, comprising the ETM labels, is used to generate the signal.

As discussed herein, it should be noted that the sandwich assays can be used for the detection of primary target sequences (e.g. from a patient sample), or as a method to detect the product of an amplification reaction as outlined above; thus for example, any of the newly synthesized strands outlined above, for example using PCR, LCR, NASBA, SDA, etc., may be used as the "target sequence" in a sandwich assay.

Generally, sandwich signal amplification techniques may be described as follows. The reactions described below can occur either in the reaction module, with subsequent transfer to the detection module for detection, or in the detection module with the addition of the required components; for clarity, these are discussed together.

As a preliminary matter, as is more fully described below, capture extender probes may be added to the target sequence for attachment to an electrode in the detection module.

The methods include the addition of an amplifier probe, which is hybridized to the target sequence, either directly, or through the use of one or more label extender probes, which serves to allow "generic" amplifier probes to be made. Preferably, the amplifier probe contains a multiplicity of amplification sequences, although in some embodiments, as described below, the amplifier probe may contain only a single amplification sequence, or at least two amplification sequences. The amplifier probe may take on a number of different forms; either a branched conformation, a dendrimer conformation, or a linear "string" of amplification sequences. Label probes comprising ETMs then hybridize to the amplification sequences (or in some cases the label probes hybridize directly to the target sequence), and the ETMs are detected using the electrode, as is more fully outlined below.

As will be appreciated by those in the art, the systems of the invention may take on a large number of different configurations. In general, there are three types of systems that can be used: (1) "non-sandwich" systems (also referred to herein as "direct" detection) in which the target sequence itself is labeled with ETMs (again, either because the primers comprise ETMs or due to the incorporation of ETMs into the newly synthesized strand); (2) systems in which label probes directly bind to the target analytes; and (3) systems in which label probes are indirectly bound to the target sequences, for example through the use of amplifier probes.

Accordingly, the present invention provides compositions comprising an amplifier probe. By "amplifier probe" or "nucleic acid multimer" or "amplification multimer" or grammatical equivalents herein is meant a nucleic acid probe that is used to facilitate signal amplification. Amplifier probes comprise at least a first single-stranded nucleic acid probe sequence, as defined below, and at least one single stranded nucleic acid amplification sequence, with a multiplicity of amplification sequences being preferred.

Amplifier probes comprise a first probe sequence that is used, either directly or indirectly, to hybridize to the target sequence. That is, the amplifier probe itself may have a first probe sequence that is substantially complementary to the target sequence, or it has a first probe sequence that is substantially complementary to a portion of an additional probe, in this case called a label extender probe, that has a first portion that is substantially complementary to the target sequence. In a preferred embodiment, the first probe sequence of the amplifier probe is substantially complementary to the target sequence.

In general, as for all the probes herein, the first probe sequence is of a length sufficient to give specificity and stability. Thus generally, the probe sequences of the invention that are designed to hybridize to another nucleic acid (i.e. probe sequences, amplification sequences, portions or domains of larger probes) are at least about 5 nucleosides long, with at least about 10 being preferred and at least about 15 being especially preferred.

In a preferred embodiment, the amplifier probes, or any of the other probes of the invention, may form hairpin stem-loop structures in the absence of their target. The length of the stem double-stranded sequence will be selected such that the hairpin structure is not favored in the presence of target. The use of these type of probes, in the systems of the invention or in any nucleic acid detection systems, can result in a significant decrease in non-specific binding and thus an increase in the signal to noise ratio.

Generally, these hairpin structures comprise four components. The first component is a target binding sequence, i.e. a region complementary to the target (which may be the sample target sequence or another probe sequence to which binding is desired), that is about 10 nucleosides long, with about 15 being preferred. The second component is a loop sequence, that can facilitate the formation of nucleic acid loops. Particularly preferred in this regard are repeats of GTC, which has been identified in Fragile X Syndrome as forming turns. (When PNA analogs are used, turns comprising proline residues may be preferred). Generally, from three to five repeats are used, with four to five being preferred. The third component is a self-complementary region, which has a first portion that is complementary to a portion of the target sequence region and a second portion that comprises a first portion of the label probe binding sequence. The fourth component is substantially complementary to a label probe (or other probe, as the case may be). The fourth component further comprises a "sticky end", that is, a portion that does not hybridize to any other portion of the probe, and preferably contains most, if not all, of the ETMs. As will be appreciated by those in the art, any or all of the probes described herein may be configured to form hairpins in the absence of their targets, including the amplifier, capture, capture extender, label and label extender probes.

In a preferred embodiment, several different amplifier probes are used, each with first probe sequences that will hybridize to a different portion of the target sequence. That is, there is more than one level of amplification; the amplifier probe provides an amplification of signal due to a multiplicity of labelling events, and several different amplifier probes, each with this multiplicity of labels, for each target sequence is used. Thus, preferred embodiments utilize at least two different pools of amplifier probes, each pool having a different probe sequence for hybridization to different portions of the target sequence; the only real limitation on the number of different amplifier probes will be the length of the original target sequence. In addition, it is also possible that the different amplifier probes contain different amplification sequences, although this is generally not preferred.

In a preferred embodiment, the amplifier probe does not hybridize to the sample target sequence directly, but instead hybridizes to a first portion of a label extender probe. This is particularly useful to allow the use of "generic" amplifier probes, that is, amplifier probes that can be used with a variety of different targets. This may be desirable since several of the amplifier probes require special synthesis techniques. Thus, the addition of a relatively short probe as a label extender probe is preferred. Thus, the first probe sequence of the amplifier probe is substantially complementary to a first portion or domain of a first label extender single-stranded nucleic acid probe. The label extender probe also contains a second portion or domain that is substantially complementary to a portion of the target sequence. Both of these portions are preferably at least about 10 to about 50 nucleotides in length, with a range of about 15 to about 30 being preferred. The terms "first" and "second" are not meant to confer an orientation of the sequences with respect to the 5'→3' orientation of the target or probe sequences. For example, assuming a 5'→3' orientation of the complementary target sequence, the first portion may be located either 5' to the second portion, or 3' to the second portion. For convenience herein, the order of probe sequences are generally shown from left to right.

In a preferred embodiment, more than one label extender probe-amplifier probe pair may be used. That is, a plurality of label extender probes may be used, each with a portion that is substantially complementary to a different portion of the target sequence; this can serve as another level of amplification. Thus, a preferred embodiment utilizes pools of at least two label extender probes, with the upper limit being set by the length of the target sequence.

In a preferred embodiment, more than one label extender probe is used with a single amplifier probe to reduce non-specific binding, as is generally outlined in U.S. Pat. No. 5,681,697, incorporated by reference herein. In this embodiment, a first portion of the first label extender probe hybridizes to a first portion of the target sequence, and the second portion of the first label extender probe hybridizes to a first probe sequence of the amplifier probe. A first portion of the second label extender probe hybridizes to a second portion of the target sequence, and the second portion of the second label extender probe hybridizes to a second probe sequence of the amplifier probe. These form structures sometimes referred to as "cruciform" structures or configurations, and are generally done to confer stability when large branched or dendrimeric amplifier probes are used.

In addition, as will be appreciated by those in the art, the label extender probes may interact with a preamplifier probe, described below, rather than the amplifier probe directly.

Similarly, as outlined above, a preferred embodiment utilizes several different amplifier probes, each with first probe sequences that will hybridize to a different portion of the label extender probe. In addition, as outlined above, it is also possible that the different amplifier probes contain different amplification sequences, although this is generally not preferred.

In addition to the first probe sequence, the amplifier probe also comprises at least one amplification sequence. An "amplification sequence" or "amplification segment" or grammatical equivalents herein is meant a sequence that is used, either directly or indirectly, to bind to a first portion of a label probe as is more fully described below (although in some cases the amplification sequence may bind to a detection probe). Preferably, the amplifier probe comprises a multiplicity of amplification sequences, with from about 3 to about 1000 being preferred, from about 10 to about 100 being particularly preferred, and about 50 being especially preferred. In some cases, for example when linear amplifier probes are used, from 1 to about 20 is preferred with from about 5 to about 10 being particularly preferred.

The amplification sequences may be linked to each other in a variety of ways, as will be appreciated by those in the art. They may be covalently linked directly to each other, or to intervening sequences or chemical moieties, through nucleic acid linkages such as phosphodiester bonds, PNA bonds, etc., or through interposed linking agents such amino acid, carbohydrate or polyol bridges, or through other cross-linking agents or binding partners. The site(s) of linkage may be at the ends of a segment, and/or at one or more internal nucleotides in the strand. In a preferred embodiment, the amplification sequences are attached via nucleic acid linkages.

In a preferred embodiment, branched amplifier probes are used, as are generally described in U.S. Pat. No. 5,124,246, hereby incorporated by reference. Branched amplifier probes may take on "fork-like" or "comb-like" conformations. "Fork-like" branched amplifier probes generally have three or more oligonucleotide segments emanating from a point of origin to form a branched structure. The point of origin may be another nucleotide segment or a multifunctional molecule to which at least three segments can be covalently or tightly bound. "Comb-like" branched amplifier probes have a linear backbone with a multiplicity of sidechain oligonucleotides extending from the backbone. In either conformation, the pendant segments will normally depend from a modified nucleotide or other organic moiety having the appropriate functional groups for attachment of oligonucleotides. Furthermore, in either conformation, a large number of amplification sequences are available for binding, either directly or indirectly, to detection probes. In general, these structures are made as is known in the art, using modified multifunctional nucleotides, as is described in U.S. Pat. Nos. 5,635,352 and 5,124,246, among others.

In a preferred embodiment, dendrimer amplifier probes are used, as are generally described in U.S. Pat. No. 5,175,270, hereby expressly incorporated by reference. Dendrimeric amplifier probes have amplification sequences that are attached via hybridization, and thus have portions of double-stranded nucleic acid as a component of their structure. The outer surface of the dendrimer amplifier probe has a multiplicity of amplification sequences.

In a preferred embodiment, linear amplifier probes are used, that have individual amplification sequences linked end-to-end either directly or with short intervening sequences to form a polymer. As with the other amplifier configurations, there may be additional sequences or moieties between the amplification sequences. In addition, as outlined herein, linear amplification probes may form hairpin stem-loop structures.

In one embodiment, the linear amplifier probe has a single amplification sequence. This may be useful when cycles of hybridization/disassociation occurs, forming a pool of amplifier probe that was hybridized to the target and then removed to allow more probes to bind, or when large numbers of ETMs are used for each label probe. However, in a preferred embodiment, linear amplifier probes comprise a multiplicity of amplification sequences.

In addition, the amplifier probe may be totally linear, totally branched, totally dendrimeric, or any combination thereof.

The amplification sequences of the amplifier probe are used, either directly or indirectly, to bind to a label probe to allow detection. In a preferred embodiment, the amplification sequences of the amplifier probe are substantially complementary to a first portion of a label probe. Alternatively, amplifier extender probes are used, that have a first portion that binds to the amplification sequence and a second portion that binds to the first portion of the label probe.

In addition, the compositions of the invention may include "preamplifier" molecules, which serves a bridging moiety between the label extender molecules and the amplifier probes. In this way, more amplifier and thus more ETMs are ultimately bound to the detection probes. Preamplifier molecules may be either linear or branched, and typically contain in the range of about 30-3000 nucleotides.

Thus, label probes are either substantially complementary to an amplification sequence or to a portion of the target sequence. Accordingly, the label probes can be configured in a variety of ways, as is generally described herein, depending on whether a "mechanism-1" or "mechanism-2" detection system is utilized, as described below.

Detection of the amplification reactions of the invention, including the direct detection of amplification products and indirect detection utilizing label probes (i.e. sandwich assays), is done by detecting assay complexes comprising ETMs, which can be attached to the assay complex in a variety of ways, as is more fully described below.

In addition, as described in U.S. Pat. No. 5,587,128, the reaction chamber may comprise a composition, either in solution or adhered to the surface of the reaction chamber, that prevents the inhibition of an amplification reaction by the composition of the well. For example, the wall surfaces may be coated with a silane, for example using a silanization reagent such as dimethylchlorosilane, or coated with a siliconizing reagent such as Aquasil™ or Surfacil™ (Pierce, Rockford, Ill.), which are organosilanes containing a hydrolyzable group. This hydrolyzable group can hydrolyze in solution to form a silanol that can polymerize and form a tightly bonded film over the surface of the chamber. The coating may also include a blocking agent that can react with the film to further reduce inhibition; suitable blocking agents include amino acid polymers and polymers such as polyvinylpyrrolidone, polyadenylic acid and polymaleimide. Alternatively, for silicon substrates, a silicon oxide film may be provided on the walls, or the reaction chamber can be coated with a relatively inert polymer such as a polyvinylchloride. In addition, it may be desirable to add blocking polynucleotides to occupy any binding sites on the surface of the chamber.

In this and other embodiments, a thermal module may be used, that is either part of the reaction chamber or separate but can be brought into spatial proximity to the reaction module. The thermal module can include both heating and/or cooling capability. Suitable thermal modules are described in U.S. Pat. Nos. 5,498,392 and 5,587,128, and WO 97/16561, incorporated by reference, and may comprise electrical resistance heaters, pulsed lasers or other sources of electromagnetic energy directed to the reaction chamber. It should also be noted that when heating elements are used, it may be desirable to have the reaction chamber be relatively shallow, to facilitate heat transfer; see U.S. Pat. No. 5,587,128.

In a preferred embodiment, the biological reaction chamber allows enzymatic cleavage or alteration of the target analyte. For example, restriction endonucleases may be used to cleave target nucleic acids comprising target sequences, for example genomic DNA, into smaller fragments to facilitate either amplification or detection. Alternatively, when the target analyte is a protein, it may be cleaved by a protease. Other types of enzymatic hydrolysis may also be done, depending on the composition of the target analyte. In addition, as outlined herein, the target analyte may comprise an enzyme and the reaction chamber comprises a substrate that is then cleaved to form a detectable product.

In addition, in one embodiment the reaction module includes a chamber for the physical alteration of all or part of the sample, for example for shearing genomic or large nucleic acids, nuclear lysis, ultrasound, etc.

In a preferred embodiment, the devices of the invention include at least one fluid pump. Pumps generally fall into two categories: "on chip" and "off chip"; that is, the pumps (generally electrode based pumps) can be contained within the device itself, or they can be contained on an apparatus into which the device fits, such that alignment occurs of the required flow channels to allow pumping of fluids.

In a preferred embodiment, the pumps are contained on the device itself. These pumps are generally electrode based pumps; that is, the application of electric fields can be used to move both charged particles and bulk solvent, depending on the composition of the sample and of the device. Suitable on chip pumps include, but are not limited to, electroosmotic (EO) pumps and electrohydrodynamic (EHD) pumps; these electrode based pumps have sometimes been referred to in the art as "electrokinetic (EK) pumps". All of these pumps rely on configurations of electrodes placed along a flow channel to result in the pumping of the fluids comprising the sample components. As is described in the art, the configurations for each of these electrode based pumps are slightly different; for example, the effectiveness of an EHD pump depends on the spacing between the two electrodes, with the closer together they are, the smaller the voltage required to be applied to effect fluid flow. Alternatively, for EO pumps, the sampling between the electrodes should be larger, with up to one-half the length of the channel in which fluids are being moved, since the electrode are only involved in applying force, and not, as in EHD, in creating charges on which the force will act.

In a preferred embodiment, an electroosmotic pump is used. Electroosmosis (EO) is based on the fact that the surface of many solids, including quartz, glass and others, become variously charged, negatively or positively, in the presence of ionic materials. The charged surfaces will attract oppositely charged counterions in aqueous solutions. Applying a voltage results in a migration of the counterions to the oppositely changed electrode, and moves the bulk of the fluid as well. The volume flow rate is proportional to the current, and the volume flow generated in the fluid is also proportional to the applied voltage. Electroosmostic flow is useful for liquids having some conductivity is and generally not applicable for non-polar solvents. EO pumps are described in U.S. Pat. Nos. 4,908,112 and 5,632,876, PCT US95/14586 and WO97/43629, incorporated by reference.

In a preferred embodiment, an electrohydrodynamic (EHD) pump is used. In EHD, electrodes in contact with the fluid transfer charge when a voltage is applied. This charge transfer occurs either by transfer or removal of an electron to or from the fluid, such that liquid flow occurs in the direction from the charging electrode to the oppositely charged electrode. EHD pumps can be used to pump resistive fluids such as non-polar solvents. EHD pumps are described in U.S. Pat. No. 5,632,876, hereby incorporated by reference.

The electrodes of the pumps preferably have a diameter from about 25 microns to about 100 microns, more preferably from about 50 microns to about 75 microns. Preferably, the electrodes protrude from the top of a flow channel to a depth of from about 5% to about 95% of the depth of the channel, with from about 25% to about 50% being preferred. In addition, as described in PCT US95/14586, an electrode-based internal pumping system can be integrated into the liquid distribution system of the devices of the invention with flow-rate control at multiple pump sites and with fewer complex electronics if the pumps are operated by applying pulsed voltages across the electrodes; this gives the additional advantage of ease of integration into high density systems, reductions in the amount of electrolysis that occurs at electrodes, reductions in thermal convection near the electrodes, and the ability to use simpler drivers, and the ability to use both simple and complex pulse wave geometries.

The voltages required to be applied to the electrodes cause fluid flow depends on the geometry of the electrodes and the properties of the fluids to be moved. The flow rate of the fluids is a function of the amplitude of the applied voltage between electrode, the electrode geometry and the fluid properties, which can be easily determined for each fluid. Test voltages used may be up to about 1500 volts, but an operating voltage of about 40 to 300 volts is desirable. An analog driver is generally used to vary the voltage applied to the pump from a DC power source. A transfer function for each fluid is determined experimentally as that applied voltage that produces the desired flow or fluid pressure to the fluid being moved in the channel. However, an analog driver is generally required for each pump along the channel and is suitable an operational amplifier.

In a preferred embodiment, a micromechanical pump is used, either on- or off chip, as is known in the art.

In a preferred embodiment, an "off-chip" pump is used. For example, the devices of the invention may fit into an apparatus or appliance that has a nesting site for holding the device, that can register the ports (i.e. sample inlet ports, fluid inlet ports, and waste outlet ports) and electrode leads. The apparatus can including pumps that can apply the sample to the device; for example, can force cell containing samples into cell lysis modules containing protrusions, to cause cell lysis upon application of sufficient flow pressure. Such pumps are well known in the art.

In a preferred embodiment, the devices of the invention include at least one fluid valve that can control the flow of fluid into or out of a module of the device, or divert the flow into one or more channels. A variety of valves are known in the art. For example, in one embodiment, the valve may comprise a capillary barrier, as generally described in PCT US97/07880, incorporated by reference. In this embodiment, the channel opens into a larger space designed to favor the formation of an energy minimizing liquid surface such as a meniscus at the opening. Preferably, capillary barriers include a dam that raises the vertical height of the channel immediated before the opening into a larger space such a chamber. In addition, as described in U.S. Pat. No. 5,858,195, incorporated herein by reference, a type of "virtual valve" can be used.

In a preferred embodiment, the devices of the invention include sealing ports, to allow the introduction of fluids, including samples, into any of the modules of the invention, with subsequent closure of the port to avoid the loss of the sample.

In a preferred embodiment, the devices of the invention include at least one storage modules for assay reagents. These are connected to other modules of the system using flow channels and may comprise wells or chambers, or extended flow channels. They may contain any number of reagents, buffers, enzymes, electronic mediators, salts, etc., including freeze dried reagents.

In a preferred embodiment, the devices of the invention include a mixing module; again, as for storage modules, these may be extended flow channels (particularly useful for timed mixing), wells or chambers. Particularly in the case of extended flow channels, there may be protrusions on the side of the channel to cause mixing.

In a preferred embodiment, the devices of the invention include a detection module. The present invention is directed to methods and compositions useful in the detection of biological target analyte species such as nucleic acids and proteins. In general, the detection module is based on work outlined in U.S. Pat. Nos. 5,591,578; 5,824,473; 5,770,363; 5,705,348 and 5,780,234; U.S. Ser. Nos. 09/096,593; 08/911,589; 09/135,183; and 60/105,875; and PCT applications US97/20014 and US98/12082; all of which are hereby incorporated by reference in their entirety. The system is generally described as follows. A target analyte is introduced to the detection module, and is combined with other components to form an assay complex in a variety of ways, as is more fully outlined below. The assay complexes comprise electron transfer moieties (ETMs), which can be attached to the assay complex in a variety of ways, as is more fully described below. In general, there are two basic detection mechanisms. In a preferred embodiment, detection of an ETM is based on electron transfer through the stacked π-orbitals of double stranded nucleic acid. This basic mechanism is described in U.S. Pat. Nos. 5,591,578, 5,770,369, and 5,705,348 and PCT US97/20014 and is termed "mechanism-1" herein. Briefly, previous work has shown that electron transfer can proceed rapidly through the stacked π-orbitals of double stranded nucleic acid, and significantly more slowly through single-stranded nucleic acid. Accordingly, this can serve as the basis of an assay. Thus, by adding ETMs (either covalently to one of the strands or non-covalently to the hybridization complex through the use of hybridization indicators, described below) to a nucleic acid that is attached to a detection electrode via a conductive oligomer, electron transfer between the ETM and the electrode, through the nucleic acid and conductive oligomer, may be detected.

This may be done where the target analyte is a nucleic acid; alternatively, a non-nucleic acid target analyte is used, with an optional capture binding ligand (to attach the target analyte to the detection electrode) and a soluble binding ligand that carries a nucleic acid "tail", that can then bind either directly or indirectly to a detection probe on the surface to effect detection.

Alternatively, the ETM can be detected, not necessarily via electron transfer through nucleic acid, but rather can be directly detected using conductive oligomers; that is, the electrons from the ETMs need not travel through the stacked n orbitals in order to generate a signal. Instead, the presence of ETMs on the surface of a SAM, that comprises conductive oligomers, can be directly detected. This basic idea is termed "mechanism-2" herein. Thus, upon binding of a target analyte, a soluble binding ligand comprising an ETM is brought to the surface, and detection of the ETM can proceed, putatively through the conductive oligomer to the electrode. Essentially, the role of the SAM comprising the conductive oligomers is to "raise" the electronic surface of the electrode, while still providing the benefits of shielding the electrode from solution components and reducing the amount of non-specific binding to the electrodes. Viewed differently, the role of the binding ligand is to provide specificity for a recruitment of ETMs to the surface, where they can be detected using conductive oligomers with electronically exposed termini.

Thus, in either embodiment, an assay complex is formed that contains an ETM, which is then detected using the detection electrode.

The present system finds particular utility in array formats, i.e. wherein there is a matrix of addressable microscopic detection electrodes (herein generally referred to as "pads", "addresses" or "micro-locations").

Accordingly, the present invention provides methods for detecting target analytes in sample solutions using an electrode. If required, the target analyte is prepared using known techniques, generally within the devices outlined above. For example, the sample may be treated to lyse the cells, using known lysis buffers, sonication, electroporation, etc., with purification occurring as needed, as will be appreciated by those in the art.

The detection modules of the invention comprise electrodes. By "electrode" herein is meant a composition, which, when connected to an electronic device, is able to sense a current or charge and convert it to a signal. Alternatively an electrode can be defined as a composition which can apply a potential to and/or pass electrons to or from species in the solution. Thus, an electrode is an ETM as described herein. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including, glassy carbon electrodes, graphite and carbon paste). Preferred electrodes include gold, silicon, platinum, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of nucleic acids are made, thus requiring addressable locations for both synthesis and detection. Alternatively, for single probe analysis, the electrode may be in the form of a tube, with the SAMs comprising conductive oligomers and nucleic acids bound to the inner surface. Electrode coils may be preferred in some embodiments as well. This allows a maximum of surface area containing the nucleic acids to be exposed to a small volume of sample.

The detection electrode comprises a self-assembled monolayer (SAM) comprising conductive oligomers. By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. The SAM may comprise conductive oligomers alone, or a mixture of conductive oligomers and insulators. As outlined herein, the efficiency of target analyte binding (for example, oligonucleotide hybridization) may increase when the analyte is at a distance from the electrode. Similarly, nonspecific binding of biomolecules, including the target analytes, to an electrode is generally reduced when a monolayer is present. Thus, a monolayer facilitates the maintenance of the analyte away from the electrode surface. In addition, a monolayer serves to keep charged species away from the surface of the electrode. Thus, this layer helps to prevent electrical contact between the electrodes and the ETMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accessibility to the electrode.

In a preferred embodiment, the monolayer comprises conductive oligomers. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated ETM. Furthermore, the conductive oligomer is more conductive than the insulators as defined herein. Additionally, the conductive oligomers of the invention are to be distinguished from electroactive polymers, that themselves may donate or accept electrons.

In a preferred embodiment, the conductive oligomers have a conductivity, S, of from between about $10^{-6}$ to about $10^4$ $\Omega^{-1}cm^{-1}$, with from about $10^{-5}$ to about $10^3$ $\Omega^{-1}cm^{-1}$ being preferred, with these S values being calculated for molecules ranging from about 20 Å to about 200 Å. As described below, insulators have a conductivity S of about $10^{-7}$ $\Omega^{-1}cm^{-1}$ or lower, with less than about $10^{-8}$ $\Omega^{-1}cm^{-1}$ being preferred. See generally Gardner et al., Sensors and Actuators A 51 (1995) 57-66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during binding ligand synthesis (i.e. nucleic acid synthesis, such that nucleosides containing the conductive oligomers may be added to a nucleic acid synthesizer during the synthesis of the compositions of the invention, ii) during the attachment of the conductive oligomer to an electrode, or iii) during binding assays. In addition, conductive oligomers that will promote the formation of self-assembled monolayers are preferred.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 1:

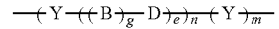

Structure 1

As will be understood by those in the art, all of the structures depicted herein may have additional atoms or structures; i.e. the conductive oligomer of Structure 1 may be attached to ETMs, such as electrodes, transition metal complexes, organic ETMs, and metallocenes, and to binding ligands such as nucleic acids, or to several of these. Unless otherwise noted, the conductive oligomers depicted herein will be attached at the left side to an electrode; that is, as depicted in Structure 1, the left "Y" is connected to the electrode as described herein. If the conductive oligomer is to be attached to a binding ligand, the right "Y", if present, is attached to the binding ligand such as a nucleic acid, either directly or through the use of a linker, as is described herein.

In this embodiment, Y is an aromatic group, n is an integer from 1 to 50, g is either 1 or zero, e is an integer from zero to 10, and m is zero or 1. When g is 1, B-D is a bond able to conjugate with neighboring bonds (herein referred to as a "conjugated bond"), preferably selected from acetylene, alkene, substituted alkene, amide, azo, —C=N— (including —N=C—, —CR=N— and —N=CR—), —Si=Si—, and —Si=C— (including —C=Si—, —Si=CR— and —CR=Si—). When g is zero, e is preferably 1, D is preferably carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—$SO_2$—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups.

The aromatic group may be substituted with a substitution group, generally depicted herein as R. R groups may be added as necessary to affect the packing of the conductive oligomers, i.e. R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first two or three oligomer subunits, depending on the average length of the molecules making up the monolayer.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —$NH_2$, —NHR and —$NR_2$ groups, with R being as defined herein.

By "nitro group" herein is meant an —$NO_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCHO groups.

By "alcohol" herein is meant —OH groups, and alkyl alcohols —ROH. By "amido" herein is meant —RCONH— or RCONR— groups.

By "ethylene glycol" or "(poly)ethylene glycol" herein is meant a —$(O-CH_2-CH_2)_n$ group, although each carbon atom of the ethylene group may also be singly or doubly substituted, i.e. —$(O-CR_2-CR_2)_n$—, with R as described above. Ethylene glycol derivatives with other heteroatoms in place of oxygen (i.e. —$(N-CH_2-CH_2)_n$— or —$(S-CH_2-CH_2)_n$—, or with substitution groups) are also preferred.

Preferred substitution groups include, but are not limited to, methyl, ethyl, propyl, alkoxy groups such as —O—$(CH_2)_2CH_3$ and —O—$(CH_2)_4CH_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B-D is a bond linking two atoms or chemical moieties. In a preferred embodiment, B-D is a conjugated bond, containing overlapping or conjugated π-orbitals.

Preferred B-D bonds are selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —CR═N—, —N═CH— and —N═CR—), (—SiH═SiH—, —SiR═SiH—, —SiR═SiH—, and —SiR═SiR—), (—SiH═CH—, —SiR═CH—, —SiH═CR—, —SiR═CR—, —CH═SiH—, —CR═SiH—, —CH═SiR—, and —CR═SiR—). Particularly preferred B-D bonds are acetylene, alkene, amide, and substituted derivatives of these three, and azo. Especially preferred B-D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 1 conductive oligomer, e is preferably 1 and the D moiety may be carbonyl or a heteroatom moiety as defined above.

As above for the Y rings, within any single conductive oligomer, the B-D bonds (or D moieties, when g=0) may be all the same, or at least one may be different. For example, when m is zero, the terminal B-D bond may be an amide bond, and the rest of the B-D bonds may be acetylene bonds. Generally, when amide bonds are present, as few amide bonds as possible are preferable, but in some embodiments all the B-D bonds are amide bonds. Thus, as outlined above for the Y rings, one type of B-D bond may be present in the conductive oligomer within a monolayer as described below, and another type above the monolayer level, for example to give greater flexibility for nucleic acid hybridization when the nucleic acid is attached via a conductive oligomer.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient hybridization of nucleic acids on a surface, the hybridization should occur at a distance from the surface, i.e. the kinetics of hybridization increase as a function of the distance from the surface, particularly for long oligonucleotides of 200 to 300 basepairs. Accordingly, when a nucleic acid is attached via a conductive oligomer, as is more fully described below, the length of the conductive oligomer is such that the closest nucleotide of the nucleic acid is positioned from about 6 Å to about 100 Å (although distances of up to 500 Å may be used) from the electrode surface, with from about 15 Å to about 60 Å being preferred and from about 25 Å to about 60 Å also being preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B-D bond or D moiety, i.e. the D atom is attached to the nucleic acid either directly or via a linker. In some embodiments, for example when the conductive oligomer is attached to a phosphate of the ribose-phosphate backbone of a nucleic acid, there may be additional atoms, such as a linker, attached between the conductive oligomer and the nucleic acid. Additionally, as outlined below, the D atom may be the nitrogen atom of the amino-modified ribose. Alternatively, when m is 1, the conductive oligomer may terminate in Y, an aromatic group, i.e. the aromatic group is attached to the nucleic acid or linker.

As will be appreciated by those in the art, a large number of possible conductive oligomers may be utilized. These include conductive oligomers falling within the Structure 1 and Structure 8 formulas, as well as other conductive oligomers, as are generally known in the art, including for example, compounds comprising fused aromatic rings or Teflon®-like oligomers, such as —(CF$_2$)$_n$, (CHF)$_n$— and —(CFR)$_n$—. See for example, Schumm et al., Angew. Chem. Intl. Ed. Engl. 33:1361 (1994); Grosshenny et al., Platinum Metals Rev. 40(1):26-35 (1996); Tour, Chem. Rev. 96:537-553 (1996); Hsung et al., Organometallics 14:4808-4815 (1995; and references cited therein, all of which are expressly incorporated by reference.

Particularly preferred conductive oligomers of this embodiment are depicted below:

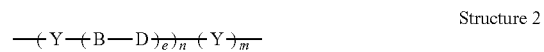

Structure 2

Structure 2 is Structure 1 when g is 1. Preferred embodiments of Structure 2 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B-D is acetylene and Y is phenyl or substituted phenyl (see Structure 4 below). A preferred embodiment of Structure 2 is also when e is one, depicted as Structure 3 below:

Structure 3

Preferred embodiments of Structure 3 are: Y is phenyl or substituted phenyl and B-D is azo; Y is phenyl or substituted phenyl and B-D is acetylene; Y is phenyl or substituted phenyl and B-D is alkene; Y is pyridine or substituted pyridine and B-D is acetylene; Y is thiophene or substituted thiophene and B-D is acetylene; Y is furan or substituted furan and B-D is acetylene; Y is thiophene or furan (or substituted thiophene or furan) and B-D are alternating alkene and acetylene bonds.

Most of the structures depicted herein utilize a Structure 3 conductive oligomer. However, any. Structure 3 oligomers may be substituted with any of the other structures depicted herein, i.e. Structure 1 or 8 oligomer, or other conducting oligomer, and the use of such Structure 3 depiction is not meant to limit the scope of the invention.

Particularly preferred embodiments of Structure 3 include Structures 4, 5, 6 and 7, depicted below:

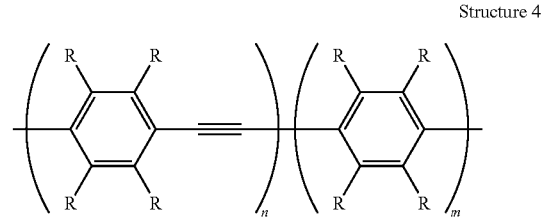

Structure 4

Particularly preferred embodiments of Structure 4 include: n is two, m is one, and R is hydrogen; n is three, m is zero, and R is hydrogen; and the use of R groups to increase solubility.

Structure 5

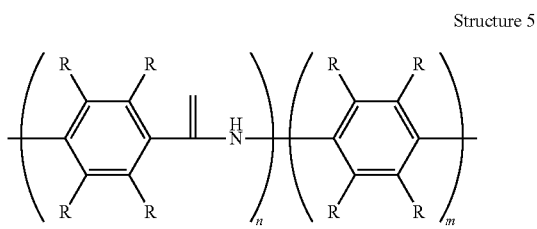

When the B-D bond is an amide bond, as in Structure 5, the conductive oligomers are pseudopeptide oligomers. Although the amide bond in Structure 5 is depicted with the carbonyl to the left, i.e. —CONH—, the reverse may also be used, i.e. —NHCO—. Particularly preferred embodiments of Structure 5 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

Structure 6

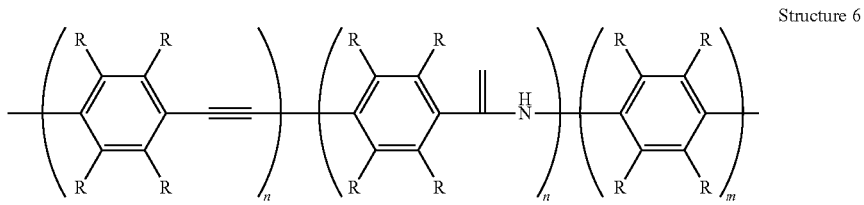

Preferred embodiments of Structure 6 include the first n is two, second n is one, m is zero, and all R groups are hydrogen, or the use of R groups to increase solubility.

Structure 7

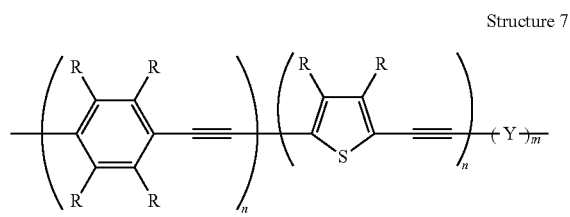

Preferred embodiments of Structure 7 include: the first n is three, the second n is from 1-3, with m being either 0 or 1, and the use of R groups to increase solubility.

In a preferred embodiment, the conductive oligomer has the structure depicted in Structure 8:

Structure 8

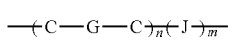

In this embodiment, C are carbon atoms, n is an integer from 1 to 50, m is 0 or 1, J is a heteroatom selected from the group consisting of oxygen, nitrogen, silicon, phosphorus, sulfur, carbonyl or sulfoxide, and G is a bond selected from alkane, alkene or acetylene, such that together with the two carbon atoms the C-G-C group is an alkene (—CH=CH—), substituted alkene (—CR=CR—) or mixtures thereof (—CH=CR— or —CR=CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In some embodiments, for example when ETMs are not present, if m=0 then at least one of the G bonds is not an alkane bond.

In a preferred embodiment, the m of Structure 8 is zero. In a particularly preferred embodiment, m is zero and G is an alkene bond, as is depicted in Structure 9:

Structure 9

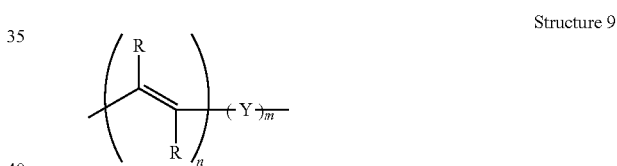

The alkene oligomer of structure 9, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 1 and 8.

In addition, particularly for use with mechanism-2 systems, the monolayer comprises conductive oligomers, and the terminus of at least some of the conductive oligomers in the monolayer are electronically exposed. By "electronically exposed" herein is meant that upon the placement of an ETM in close proximity to the terminus, and after initiation with the appropriate signal, a signal dependent on the presence of the ETM may be detected. The conductive oligomers may or may not have terminal groups. Thus, in a preferred embodiment, there is no additional terminal group, and the conductive oligomer terminates with one of the groups depicted in Structures 1 to 9; for example, a BD bond such as an acetylene bond. Alternatively, in a preferred embodiment, a terminal group is added, sometimes depicted herein as "Q". A terminal group may be used for several reasons; for example, to contribute to the electronic availability of the conductive oligomer for detection of ETMs, or to alter the surface of the SAM for other reasons, for example to prevent non-specific binding. For example, when the target analyte is a nucleic acid, there may be negatively charged groups on the terminus to form a negatively charged surface such that when the nucleic acid is DNA or RNA the nucleic acid is repelled or prevented from lying down on the surface, to facilitate hybridization. Preferred terminal groups include —NH$_2$, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

It will be appreciated that the monolayer may comprise different conductive oligomer species, although preferably the different species are chosen such that a reasonably uniform SAM can be formed. Thus, for example, when capture binding ligands such as nucleic acids are covalently attached to the electrode using conductive oligomers, it is possible to have one type of conductive oligomer used to attach the nucleic acid, and another type functioning to detect the ETM. Similarly, it may be desirable to have mixtures of different lengths of conductive oligomers in the monolayer, to help reduce nonspecific signals. Thus, for example, preferred embodiments utilize conductive oligomers that terminate below the surface of the rest of the monolayer, i.e. below the insulator layer, if used, or below some fraction of the other conductive oligomers. Similarly, the use of different conductive oligomers may be done to facilitate monolayer formation, or to make monolayers with altered properties.

In a preferred embodiment, the monolayer may further comprise insulator moieties. By "insulator" herein is meant a substantially nonconducting oligomer, preferably linear. By "substantially nonconducting" herein is meant that the insulator will not transfer electrons at 100 Hz. The rate of electron transfer through the insulator is preferably slower than the rate through the conductive oligomers described herein.

In a preferred embodiment, the insulators have a conductivity, S, of about $10^{-7}$ $\Omega^{-1}$cm$^{-1}$ or lower, with less than about $10^{-8}$ $\Omega^{-1}$ cm$^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

Suitable insulators are known in the art, and include, but are not limited to, —(CH$_2$)$_n$—, —(CRH)$_n$—, and —(CR$_2$)$_n$—, ethylene glycol or derivatives using other heteroatoms in place of oxygen, i.e. nitrogen or sulfur (sulfur derivatives are not preferred when the electrode is gold).

As for the conductive oligomers, the insulators may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. Similarly, the insulators may contain terminal groups, as outlined above, particularly to influence the surface of the monolayer.

The length of the species making up the monolayer will vary as needed. As outlined above, it appears that binding of target analytes (for example, hybridization of nucleic acids) is more efficient at a distance from the surface. The species to which capture binding ligands are attached (as outlined below, these can be either insulators or conductive oligomers) may be basically the same length as the monolayer forming species or longer than them, resulting in the capture binding ligands being more accessible to the solvent for hybridization. In some embodiments, the conductive oligomers to which the capture binding ligands are attached may be shorter than the monolayer.

As will be appreciated by those in the art, the actual combinations and ratios of the different species making up the monolayer can vary widely, and will depend on whether mechanism-1 or -2 is used, and whether a one electrode system or two electrode system is used, as is more fully outlined below. Generally, three component systems are preferred for mechanism-2 systems, with the first species comprising a capture binding ligand containing species (termed a capture probe when the target analyte is a nucleic acid), attached to the electrode via either an insulator or a conductive oligomer. The second species are the conductive oligomers, and the third species are insulators. In this embodiment, the first species can comprise from about 90% to about 1%, with from about 20% to about 40% being preferred. When the target analytes are nucleic acids, from about 30% to about 40% is especially preferred for short oligonucleotide targets and from about 10% to about 20% is preferred for longer targets. The second species can comprise from about 1% to about 90%, with from about 20% to about 90% being preferred, and from about 40% to about 60% being especially preferred. The third species can comprise from about 1% to about 90%, with from about 20% to about 40% being preferred, and from about 15% to about 30% being especially preferred. Preferred ratios of first:second:third species are 2:2:1 for short targets, 1:3:1 for longer targets, with total thiol concentration (when used to attach these species, as is more fully outlined below) in the 500 µM to 1 mM range, and 833 µM being preferred.

Alternatively, two component systems can be used. In one embodiment, for use in either mechanism-1 or mechanism-2 systems, the two components are the first and second species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred. Alternatively, for mechanism-1 systems, the two components are the first and the third species. In this embodiment, the first species can comprise from about 1% to about 90%, with from about 1% to about 40% being preferred, and from about 10% to about 40% being especially preferred. The second species can comprise from about 1% to about 90%, with from about 10% to about 60% being preferred, and from about 20% to about 40% being especially preferred.

The covalent attachment of the conductive oligomers and insulators to the electrode may be accomplished in a variety of ways, depending on the electrode and the composition of the insulators and conductive oligomers used. In a preferred embodiment, the attachment linkers with covalently attached nucleosides or nucleic acids as depicted herein are covalently attached to an electrode. Thus, one end or terminus of the attachment linker is attached to the nucleoside or nucleic acid, and the other is attached to an electrode. In some embodiments it may be desirable to have the attachment linker attached at a position other than a terminus, or even to have a branched attachment linker that is attached to an electrode at one terminus and to two or more nucleosides at other termini, although this is not preferred. Similarly, the attachment linker may be attached at two sites to the electrode, as is generally depicted in Structures 11-13. Generally, some type of linker is used, as depicted below as "A" in Structure 10, where "X" is the conductive oligomer, "I" is an insulator and the hatched surface is the electrode:

Structure 10

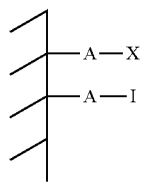

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the insulators and conductive oligomers may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 11, 12 and 13. As will be appreciated by those in the art, other such structures can be made. In Structures 11, 12 and 13, the A moiety is just a sulfur atom, but substituted sulfur moieties may also be used.

Structure 11

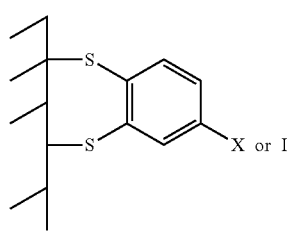

Structure 12

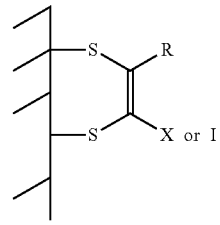

Structure 13

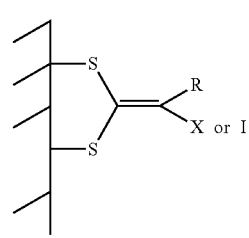

It should also be noted that similar to Structure 13, it may be possible to have a conductive oligomer terminating in a single carbon atom with three sulfur moities attached to the electrode. Additionally, although not always depicted herein, the conductive oligomers and insulators may also comprise a "Q" terminal group.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 14, using the Structure 3 conductive oligomer, although as for all the structures depicted herein, any of the conductive oligomers, or combinations of conductive oligomers, may be used. Similarly, any of the conductive oligomers or insulators may also comprise terminal groups as described herein. Structure 14 depicts the "A" linker as comprising just a sulfur atom, although additional atoms may be present (i.e. linkers from the sulfur to the conductive oligomer or substitution groups). In addition, Structure 14 shows the sulfur atom attached to the Y aromatic group, but as will be appreciated by those in the art, it may be attached to the B-D group (i.e. an acetylene) as well.

Structure 14

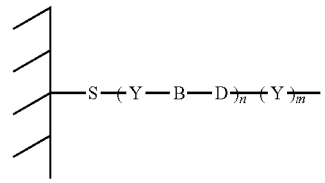

In general, thiol linkages are preferred when either two sets of electrodes are used (i.e. the detection electrodes comprising the SAMs are not used at high electrophoretic voltages (i.e. greater than 800 or 900 mV), that can cause oxidation of the thiol linkage and thus loss of the SAM), or, if one set of electrodes is used, lower electrophoretic voltages are used as is generally described below.

In a preferred embodiment, the electrode is a carbon electrode, i.e. a glassy carbon electrode, and attachment is via a nitrogen of an amine group. A representative structure is depicted in Structure 15. Again, additional atoms may be present, i.e. Z type linkers and/or terminal groups.

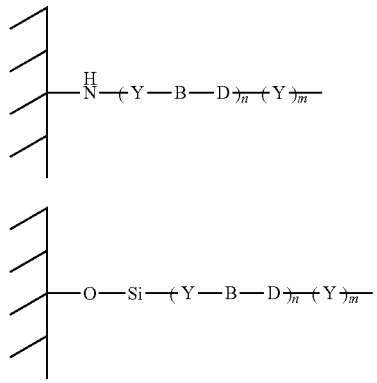

Structure 15

Structure 16

In Structure 16, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

In a preferred embodiment, the detection electrode further comprises a capture binding ligand, preferably covalently attached. In general, for most of the "mechanism-2" embodiments described herein, there are at least two binding ligands used per target analyte molecule; a "capture" or "anchor" binding ligand (also referred to herein as a "capture probe", particularly in reference to a nucleic acid binding ligand) that is attached to the detection electrode as described herein, and a soluble binding ligand, that binds independently to the target analyte, and either directly or indirectly comprises at least one ETM.

Thus, in preferred embodiments, although it is not required, the target sequences are immobilized on the electrode surface. This is preferably done using capture probes and optionally one or more capture extender probes. When only capture probes are utilized, it is necessary to have unique capture probes for each target sequence; that is, the surface must be customized to contain unique capture probes. Alternatively, capture extender probes may be used, that allow a "universal" surface, i.e. a surface containing a single type of capture probe that can be used to detect any target sequence. "Capture extender" probes have a first portion that will hybridize to all or part of the capture probe, and a second portion that will hybridize to a first portion of the target sequence. This then allows the generation of customized soluble probes, which as will be appreciated by those in the art is generally simpler and less costly. As shown herein, two capture extender probes may be used. This has generally been done to stabilize assay complexes (for example when the target sequence is large, or when large amplifier probes (particularly branched or dendrimer amplifier probes) are used.

In a preferred embodiment, the nucleic acids are added after the formation of the SAM, discussed herein. This may be done in a variety of ways, as will be appreciated by those in the art. In one embodiment, conductive oligomers with terminal functional groups are made, with preferred embodiments utilizing activated carboxylates and isothiocyanates, that will react with primary amines that are put onto the nucleic acid using an activated carboxylate. These two reagents have the advantage of being stable in aqueous solution, yet react with primary alkylamines. However, the primary aromatic amines and secondary and tertiary amines of the bases should not react, thus allowing site specific addition of nucleic acids to the surface. This allows the spotting of probes (either capture or detection probes, or both) using known methods (ink jet, spotting, etc.) onto the surface.

In addition, there are a number of non-nucleic acid methods that can be used to immobilize a nucleic acid on a surface. For example, binding partner pairs can be utilized; i.e. one binding partner is attached to the terminus of an attachment linker, described below, and the other to the end of the nucleic acid. This may also be done without using a nucleic acid capture probe; that is, one binding partner serves as the capture probe and the other is attached to either the target sequence or a capture extender probe. That is, either the target sequence comprises the binding partner, or a capture extender probe that will hybridize to the target sequence comprises the binding partner. Suitable binding partner pairs include, but are not limited to, hapten pairs such as biotin/streptavidin; antigens/antibodies; NTA/histidine tags; etc. In general, smaller binding partners are preferred, such that the electrons can pass from the nucleic acid into the conductive oligomer to allow detection.

In a preferred embodiment, when the target sequence itself is modified to contain a binding partner, the binding partner is attached via a modified nucleotide that can be enzymatically attached to the target sequence, for example during a PCR target amplification step. Alternatively, the binding partner should be easily attached to the target sequence.

Alternatively, a capture extender probe may be utilized that has a nucleic acid portion for hybridization to the target as well as a binding partner (for example, the capture extender probe may comprise a non-nucleic acid portion such as an alkyl linker that is used to attach a binding partner). In this embodiment, it may be desirable to cross-link the double-stranded nucleic acid of the target and capture extender probe for stability, for example using psoralen as is known in the art.

In one embodiment, the target is not bound to the electrode surface using capture probes. In this embodiment, what is important, as for all the assays herein, is that excess label probes be removed prior to detection and that the assay complex be in proximity to the surface. As will be appreciated by those in the art, this may be accomplished in other ways. For example, the assay complex comprising the ETMs may be present on beads that are added to the electrode comprising the monolayer, and then the beads brought into proximity of the electrode surface using techniques well known in the art, including gravity settling of the beads on the surface, electrostatic or magnetic interactions between bead components and the surface, using binding partner attachment as outlined above. Alternatively, after the removal of excess reagents such as excess label probes, the assay complex may be driven down to the surface, for example by pulsing the system with a voltage sufficient to drive the assay complex to the surface.

However, preferred embodiments utilize assay complexes attached via nucleic acid capture probes.

Generally, the capture binding ligand allows the attachment of a target analyte to the detection electrode, for the purposes of detection. As is more fully outlined below, attachment of the target analyte to the capture binding ligand may be direct (i.e. the target analyte binds to the capture binding ligand) or indirect (one or more capture extender ligands may be used).

The method of attachment of the capture binding ligands to the attachment linker (either an insulator or conductive oligomer) will generally be done as is known in the art, and will depend on both the composition of the attachment linker and the capture binding ligand. In general, the capture binding ligands are attached to the attachment linker through the use of functional groups on each that can then be used for attachment. Preferred functional groups for attachment are amino groups, carboxy groups, oxo groups and thiol groups. These functional groups can then be attached, either directly or indirectly through the use of a linker, sometimes depicted herein as "Z". Linkers are well known in the art; for example, homo- or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and C2 alkene being especially preferred. Z may also be a sulfone group, forming sulfonamide linkages.

In this way, capture binding ligands comprising proteins, lectins, nucleic acids, small organic molecules, carbohydrates, etc. can be added.

A preferred embodiment utilizes proteinaceous capture binding ligands. As is known in the art, any number of techniques may be used to attach a proteinaceous capture binding ligand to an attachment linker. "Protein" as used herein includes proteins, polypeptides, and peptides. The protein may be made up of naturally occurring amino acids and peptide bonds, or synthetic peptidomimetic structures. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. A wide variety of techniques are known to add moieties to proteins.

A preferred embodiment utilizes nucleic acids as the capture binding ligand. As will be appreciated by those in the art, many of the techniques outlined below apply in a similar manner to non-nucleic acid systems.

The capture probe nucleic acid is covalently attached to the electrode, via an "attachment linker", that can be either a conductive oligomer (required for mechanism-1 systems) or an insulator. By "covalently attached" herein is meant that two moieties are attached by at least one bond, including sigma bonds, pi bonds and coordination bonds.

Thus, one end of the attachment linker is attached to a nucleic acid (or other binding ligand), and the other end (although as will be appreciated by those in the art, it need not be the exact terminus for either) is attached to the electrode. Thus, any of structures depicted herein may further comprise a nucleic acid effectively as a terminal group. Thus, the present invention provides compositions comprising nucleic acids covalently attached to electrodes as is generally depicted below in Structure 17:

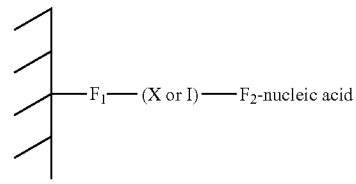

Structure 17

In Structure 17, the hatched marks on the left represent an electrode. X is a conductive oligomer and I is an insulator as defined herein. $F_1$ is a linkage that allows the covalent attachment of the electrode and the conductive oligomer or insulator, including bonds, atoms or linkers such as is described herein, for example as "A", defined below. $F_2$ is a linkage that allows the covalent attachment of the conductive oligomer or insulator to the nucleic acid, and may be a bond, an atom or a linkage as is herein described. $F_2$ may be part of the conductive oligomer, part of the insulator, part of the nucleic acid, or exogeneous to both, for example, as defined herein for "Z".

In a preferred embodiment, the capture probe nucleic acid is covalently attached to the electrode via a conductive oligomer. The covalent attachment of the nucleic acid and the conductive oligomer may be accomplished in several ways. In a preferred embodiment, the attachment is via attachment to the base of the nucleoside, via attachment to the backbone of the nucleic acid (either the ribose, the phosphate, or to an analogous group of a nucleic acid analog backbone), or via a transition metal ligand, as described below. The techniques outlined below are generally described for naturally occurring nucleic acids, although as will be appreciated by those in the art, similar techniques may be used with nucleic acid analogs, and in some cases with other binding ligands.

In a preferred embodiment, the conductive oligomer is attached to the base of a nucleoside of the nucleic acid. This may be done in several ways, depending on the oligomer, as is described below. In one embodiment, the oligomer is attached to a terminal nucleoside, i.e. either the 3' or 5' nucleoside of the nucleic acid. Alternatively, the conductive oligomer is attached to an internal nucleoside.

The point of attachment to the base will vary with the base. Generally, attachment at any position is possible. In some embodiments, for example when the probe containing the ETMs may be used for hybridization (i.e. mechanism-1 systems), it is preferred to attach at positions not involved in hydrogen bonding to the complementary base. Thus, for example, generally attachment is to the 5 or 6 position of pyrimidines such as uridine, cytosine and thymine. For purines such as adenine and guanine, the linkage is preferably via the 8 position. Attachment to non-standard bases is preferably done at the comparable positions.

In one embodiment, the attachment is direct; that is, there are no intervening atoms between the conductive oligomer and the base. In this embodiment, for example, conductive oligomers with terminal acetylene bonds are attached directly to the base. Structure 18 is an example of this linkage, using a Structure 3 conductive oligomer and uridine as the base, although other bases and conductive oligomers can be used as will be appreciated by those in the art:

Structure 18

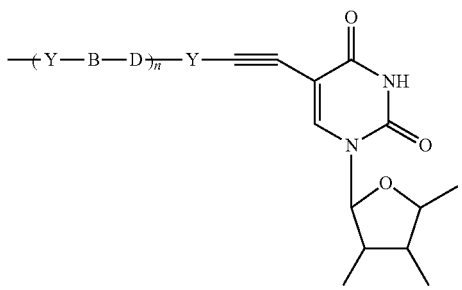

It should be noted that the pentose structures depicted herein may have hydrogen, hydroxy, phosphates or other groups such as amino groups attached. In addition, the pentose and nucleoside structures depicted herein are depicted non-conventionally, as mirror images of the normal rendering. In addition, the pentose and nucleoside structures may also contain additional groups, such as protecting groups, at any position, for example as needed during synthesis.

In addition, the base may contain additional modifications as needed, i.e. the carbonyl or amine group may be altered or protected, for example as is depicted in FIG. 3 or 10.

In an alternative embodiment, the attachment is any number of different Z linkers, including amide and amine linkages, as is generally depicted in Structure 19 using uridine as the base and a Structure 3 oligomer:

Structure 19

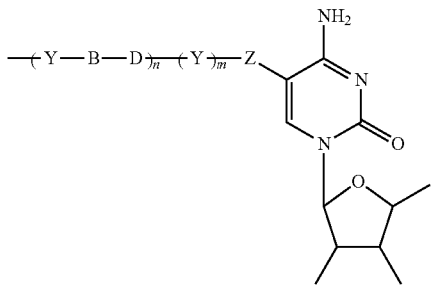

In this embodiment, Z is a linker. Preferably, Z is a short linker of about 1 to about 10 atoms, with from 1 to 5 atoms being preferred, that may or may not contain alkene, alkynyl, amine, amide, azo, imine, etc., bonds. Linkers are known in the art; for example, homo- or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages as discussed below.

In a preferred embodiment, the attachment of the nucleic acid and the conductive oligomer is done via attachment to the backbone of the nucleic acid. This may be done in a number of ways, including attachment to a ribose of the ribose-phosphate backbone, or to the phosphate of the backbone, or other groups of analogous backbones.

As a preliminary matter, it should be understood that the site of attachment in this embodiment may be to a 3' or 5' terminal nucleotide, or to an internal nucleotide, as is more fully described below.

In a preferred embodiment, the conductive oligomer is attached to the ribose of the ribose-phosphate backbone. This may be done in several ways. As is known in the art, nucleosides that are modified at either the 2' or 3' position of the ribose with amino groups, sulfur groups, silicone groups, phosphorus groups, or oxo groups can be made (Imazawa et al., J. Org. Chem., 44:2039 (1979); Hobbs et al., J. Org. Chem. 42(4):714 (1977); Verheyden et al., J. Org. Chem. 36(2):250 (1971); McGee et al., J. Org. Chem. 61:781-785 (1996); Mikhailopulo et al., Liebigs. Ann. Chem. 513-519 (1993); McGee et al., Nucleosides & Nucleotides 14(6): 1329 (1995), all of which are incorporated by reference). These modified nucleosides are then used to add the conductive oligomers.

A preferred embodiment utilizes amino-modified nucleosides. These amino-modified riboses can then be used to form either amide or amine linkages to the conductive oligomers. In a preferred embodiment, the amino group is attached directly to the ribose, although as will be appreciated by those in the art, short linkers such as those described herein for "Z" may be present between the amino group and the ribose.

In a preferred embodiment, an amide linkage is used for attachment to the ribose. Preferably, if the conductive oligomer of Structures 1-3 is used, m is zero and thus the conductive oligomer terminates in the amide bond. In this embodiment, the nitrogen of the amino group of the amino-modified ribose is the "D" atom of the conductive oligomer. Thus, a preferred attachment of this embodiment is depicted in Structure 20 (using the Structure 3 conductive oligomer):

Structure 20

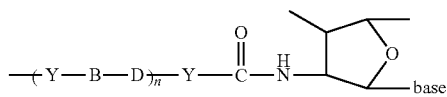

As will be appreciated by those in the art, Structure 20 has the terminal bond fixed as an amide bond.

In a heteroatom linkage, a heteroatom linkage is used, i.e. oxo, amine, sulfur, etc. A preferred embodiment utilizes an amine linkage. Again, as outlined above for the amide linkages, for amine linkages, the nitrogen of the amino-modified ribose may be the "D" atom of the conductive oligomer when the Structure 3 conductive oligomer is used. Thus, for example, Structures 21 and 22 depict nucleosides with the Structures 3 and 9 conductive oligomers, respectively, using the nitrogen as the heteroatom, although other heteroatoms can be used:

Structure 21

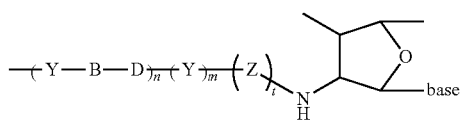

In Structure 21, preferably both m and t are not zero. A preferred Z here is a methylene group, or other aliphatic alkyl linkers. One, two or three carbons in this position are particularly useful for synthetic reasons.

Structure 22

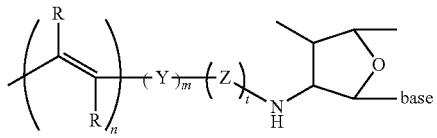

In Structure 22, Z is as defined above. Suitable linkers include methylene and ethylene.

In an alternative embodiment, the conductive oligomer is covalently attached to the nucleic acid via the phosphate of the ribose-phosphate backbone (or analog) of a nucleic acid. In this embodiment, the attachment is direct, utilizes a linker or via an amide bond. Structure 23 depicts a direct linkage, and Structure 24 depicts linkage via an amide bond (both utilize the Structure 3 conductive oligomer, although Structure 8 conductive oligomers are also possible). Structures 23 and 24 depict the conductive oligomer in the 3' position, although the 5' position is also possible. Furthermore, both Structures 23 and 24 depict naturally occurring phosphodiester bonds, although as those in the art will appreciate, non-standard analogs of phosphodiester bonds may also be used.

Structure 23

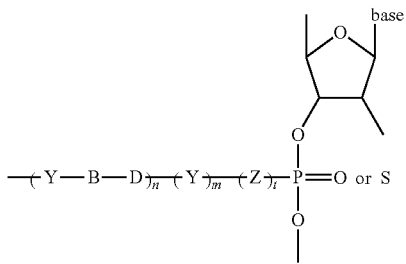

In Structure 23, if the terminal Y is present (i.e. m=1), then preferably Z is not present (i.e. t=0). If the terminal Y is not present, then Z is preferably present.

Structure 24 depicts a preferred embodiment, wherein the terminal B-D bond is an amide bond, the terminal Y is not present, and Z is a linker, as defined herein.

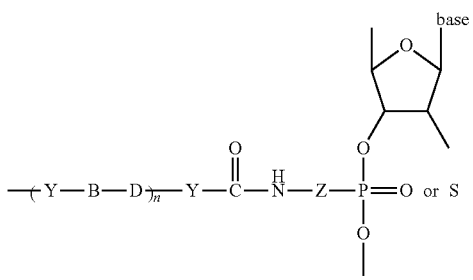

In a preferred embodiment, the conductive oligomer is covalently attached to the nucleic acid via a transition metal ligand. In this embodiment, the conductive oligomer is covalently attached to a ligand which provides one or more of the coordination atoms for a transition metal. In one embodiment, the ligand to which the conductive oligomer is attached also has the nucleic acid attached, as is generally depicted below in Structure 25. Alternatively, the conductive oligomer is attached to one ligand, and the nucleic acid is attached to another ligand, as is generally depicted below in Structure 26. Thus, in the presence of the transition metal, the conductive oligomer is covalently attached to the nucleic acid. Both of these structures depict Structure 3 conductive oligomers, although other oligomers may be utilized. Structures 25 and 26 depict two representative structures:

Structure 25

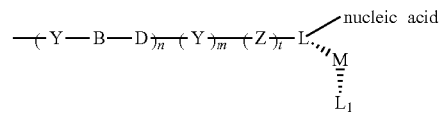

Structure 26

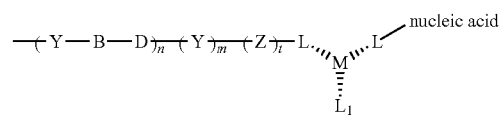

In the structures depicted herein, M is a metal atom, with transition metals being preferred. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinum (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinum, cobalt and iron.

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π)

donors, and depicted herein as $L_m$). Suitable nitrogen donating ligands are well known in the art and include, but are not limited to, $NH_2$; NHR; NRR; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10phenanthrenequinone diimine (abbreviated phi); 1,4,5,8-tetraazaphenanthrene (abbreviated tap); 1,4,8,11-tetra-azacyclotetradecane (abbreviated cyclam), EDTA, EGTA and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with n-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (−1) ion, that yield a class of bis(cyclopentadieyl) metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene $[(C_5H_5)_2Fe]$ and its derivatives are prototypical examples which have been used in a wide variety of chemical (Connelly et al., Chem. Rev. 96:877910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene)chromium is a prototypical example, Other acyclic rr-bonded ligands such as the allyl(−1) ion, or butadiene yield potentially suitable organometallic compounds, and all such ligands, in conjunction with other n-bonded and 5 bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture. These combinations are depicted in representative structures using the conductive oligomer of Structure 3 are depicted in Structures 27 (using phenanthroline and amino as representative ligands), 28 (using ferrocene as the metal-ligand combination) and 29 (using cyclopentadienyl and amino as representative ligands).

Structure 27

Structure 28

Structure 29

In a preferred embodiment, the ligands used in the invention show altered fluorescent properties depending on the redox state of the chelated metal ion. As described below, this thus serves as an additional mode of detection of electron transfer between the ETM and the electrode.

In a preferred embodiment, as is described more fully below, the ligand attached to the nucleic acid is an amino group attached to the 2' or 3' position of a ribose of the ribose-phosphate backbone. This ligand may contain a multiplicity of amino groups so as to form a polydentate ligand which binds the metal ion. Other preferred ligands include cyclopentadiene and phenanthroline.

The use of metal ions to connect the nucleic acids can serve as an internal control or calibration of the system, to evaluate the number of available nucleic acids on the surface. However, as will be appreciated by those in the art, if metal ions are used to connect the nucleic acids to the conductive oligomers, it is generally desirable to have this metal ion complex have a different redox potential than that of the ETMs used in the rest of the system, as described below. This is generally true so as to be able to distinguish the presence of the capture probe from the presence of the target sequence. This may be useful for identification, calibration and/or quantification. Thus, the amount of capture probe on an electrode may be compared to the amount of hybridized double stranded nucleic acid to quantify the amount of target sequence in a sample. This is quite significant to serve as an internal control of the sensor or system. This allows a measurement either prior to the addition of target or after, on the same molecules that will be used for detection, rather than rely on a similar but different control system. Thus, the actual molecules that will be used for the detection can be quantified prior to any experiment. This is a significant advantage over prior methods.

In a preferred embodiment, the capture probe nucleic acids (or other binding ligands) are covalently attached to the electrode via an insulator. The attachment of nucleic acids (and other binding ligands) to insulators such as alkyl groups is well known, and can be done to the base or the backbone, including the ribose or phosphate for backbones containing these moieties, or to alternate backbones for nucleic acid analogs.

In a preferred embodiment, there may be one or more different capture probe species on the surface. In some embodiments, there may be one type of capture probe, or one type of capture probe extender, as is more fully described below. Alternatively, different capture probes, or one capture probes with a multiplicity of different capture extender probes can be used. Similarly, it may be desirable (particular in the case of nucleic acid analytes and binding ligands in mechanism-2 systems) to use auxiliary capture probes that comprise relatively short probe sequences, that can be used to "tack down" components of the system, for example the recruitment linkers, to increase the concentration of ETMs at the surface.

Thus the present invention provides substrates comprising at least one detection electrode comprising monolayers and capture binding ligands, useful in target analyte detection systems.

In a preferred embodiment, the compositions further comprise a solution or soluble binding ligand, although as is more fully described below, for mechanism-1 systems, the ETMs may be added in the form of non-covalently attached hybridization indicators. Solution binding ligands are similar to capture binding ligands, in that they bind, preferably specifically, to target analytes. The solution binding ligand may be the same or different from the capture binding ligand. Generally, the solution binding ligands are not directed attached to the surface, although they may be. The solution binding ligand either directly comprises a recruitment linker that comprises at least one ETM or the recruitment linker binds, either directly or indirectly, to the solution binding ligand.

Thus, "solution binding ligands" or "soluble binding ligands" or "signal carriers" or "label probes" or "label binding ligands" with recruitment linkers comprising covalently attached ETMs are provided. That is, one portion of the label probe or solution binding ligand directly or indirectly binds to the target analyte, and one portion comprises a recruitment linker comprising covalently attached ETMs. In some systems, for example in mechanism-1 nucleic acid systems, these may be the same. Similarly, for mechanism-1 systems, the recruitment linker comprises nucleic acid that will hybridize to detection probes. The terms "electron donor moiety", "electron acceptor moiety", and "ETMs" (ETMs) or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred ETMs include, but are not limited to, transition metal complexes, organic ETMs, and electrodes.

In a preferred embodiment, the ETMs are transition metal complexes. Transition metals are those whose atoms have a partial or complete d shell of electrons. Suitable transition metals for use in the invention are listed above.

The transition metals are complexed with a variety of ligands, L, defined above, to form suitable transition metal complexes, as is well known in the art.

In addition to transition metal complexes, other organic electron donors and acceptors may be covalently attached to the nucleic acid for use in the invention. These organic molecules include, but are not limited to, riboflavin, xanthene dyes, azine dyes, acridine orange, N,N'-dimethyl-2, 7diazapyrenium dichloride ($DAP^{2+}$), methylviologen, ethidium bromide, quinones such as N,N' dimethylanthra (2,1,9-def:6,5,10-def:)diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and substituted derivatives of these compounds.

In one embodiment, the electron donors and acceptors are redox proteins as are known in the art. However, redox proteins in many embodiments are not preferred.

The choice of the specific ETMs will be influenced by the type of electron transfer detection used, as is generally outlined below. Preferred ETMs are metallocenes, with ferrocene being particularly preferred.

In a preferred embodiment, a plurality of ETMs are used. As is shown in the examples, the use of multiple ETMs provides signal amplification and thus allows more sensitive detection limits. As discussed below, while the use of multiple ETMs on nucleic acids that hybridize to complementary strands can cause decreases in $T_m$s of the hybridization complexes depending on the number, site of attachment and spacing between the multiple ETMs, this is not a factor when the ETMs are on the recruitment linker (i.e. "mechanism-2" systems), since this does not hybridize to a complementary sequence. Accordingly, pluralities of ETMs are preferred, with at least about 2 ETMs per recruitment linker being preferred, and at least about 10 being particularly preferred, and at least about 20 to 50 being especially preferred. In some instances, very large numbers of ETMs (50 to 1000) can be used.

Thus, solution binding ligands, or label probes, with covalently attached ETMs are provided. The method of attachment of the ETM to the solution binding ligand will vary depending on the mode of detection (i.e. mechanism-1 or -2 systems) and the composition of the solution binding ligand. As is more fully outlined below, in mechanism-2 systems, the portion of the solution binding ligand (or label probe) that comprises the ETM is referred to as a "recruitment linker" and can comprise either nucleic acid or non-nucleic acid. For mechanism-1 systems, the recruitment linker must be nucleic acid.

Thus, as will be appreciated by those in the art, there are a variety of configurations that can be used. In a preferred embodiment, the recruitment linker is nucleic acid (including analogs), and, attachment of the ETMs can be via (1) a base; (2) the backbone, including the ribose, the phosphate, or comparable structures in nucleic acid analogs; (3) nucleoside replacement, described below; or (4) metallocene polymers, as described below. In a preferred embodiment, the recruitment linker is non-nucleic acid, and can be either a metallocene polymer or an alkyl-type polymer (including heteroalkyl, as is more fully described below) containing ETM substitution groups.

In a preferred embodiment, the recruitment linker is a nucleic acid, and comprises covalently attached ETMs. The ETMs may be attached to nucleosides within the nucleic acid in a variety of positions. Preferred embodiments include, but are not limited to, (1) attachment to the base of the nucleoside, (2) attachment of the ETM as a base replacement, (3) attachment to the backbone of the nucleic acid, including either to a ribose of the ribose-phosphate backbone or to a phosphate moiety, or to analogous structures in nucleic acid analogs, and (4) attachment via metallocene polymers.

In addition, as is described below, when the recruitment linker is nucleic acid, it may be desirable to use secondary label probes, that have a first portion that will hybridize to a portion of the primary label probes and a second portion comprising a recruitment linker as is defined herein. This is similar to the use of an amplifier probe, except that both the primary and the secondary label probes comprise ETMs.

In a preferred embodiment, the ETM is attached to the base of a nucleoside as is generally outlined above for attachment of the conductive oligomer. Attachment can be to an internal nucleoside or a terminal nucleoside.

The covalent attachment to the base will depend in part on the ETM chosen, but in general is similar to the attachment of conductive oligomers to bases, as outlined above. Attachment may generally be done to any position of the base. In a preferred embodiment, the ETM is a transition metal complex, and thus attachment of a suitable metal ligand to the base leads to the covalent attachment of the ETM. Alternatively, similar types of linkages may be used for the attachment of organic ETMs, as will be appreciated by those in the art.

In one embodiment, the C4 attached amino group of cytosine, the C6 attached amino group of adenine, or the C2 attached amino group of guanine may be used as a transition metal ligand.

Ligands containing aromatic groups can be attached via acetylene linkages as is known in the art (see Comprehensive Organic Synthesis, Trost et al., Ed., Pergamon Press, Chapter 2.4: Coupling Reactions Between sp$^2$ and sp Carbon Centers, Sonogashira, pp 521-549, and pp 950-953, hereby incorporated by reference). Structure 30 depicts a representative structure in the presence of the metal ion and any other necessary ligands; Structure 30 depicts uridine, although as for all the structures herein, any other base may also be used.

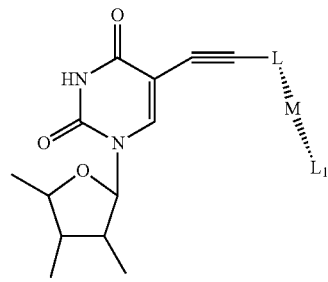

Structure 30

$L_a$ is a ligand, which may include nitrogen, oxygen, sulfur or phosphorus donating ligands or organometallic ligands such as metallocene ligands. Suitable $L_a$ ligands include, but not limited to, phenanthroline, imidazole, bpy and terpy. $L_r$ and M are as defined above. Again, it will be appreciated by those in the art, a linker ("Z") may be included between the nucleoside and the ETM.

Similarly, as for the conductive oligomers, the linkage may be done using a linker, which may utilize an amide linkage (see generally Telser et al., J. Am. Chem. Soc. 111:7221-7226 (1989); Telser et al., J. Am. Chem. Soc. 111:7226-7232 (1989), both of which are expressly incorporated by reference). These structures are generally depicted below in Structure 31, which again uses uridine as the base, although as above, the other bases may also be used:

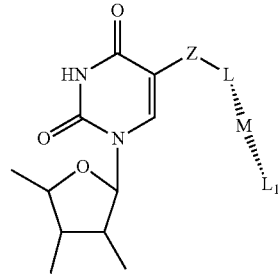

Structure 31

In this embodiment, L is a ligand as defined above, with L, and M as defined above as well. Preferably, L is amino, phen, byp and terpy.

In a preferred embodiment, the ETM attached to a nucleoside is a metallocene; i.e. the L and $L_r$ of Structure 31 are both metallocene ligands, $L_m$, as described above. Structure 32 depicts a preferred embodiment wherein the metallocene is ferrocene, and the base is uridine, although other bases may be used:

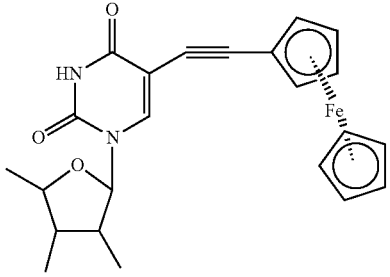

Structure 32

Preliminary data suggest that Structure 32 may cyclize, with the second acetylene carbon atom attacking the carbonyl oxygen, forming a furan-like structure. Preferred metallocenes include ferrocene, cobaltocene and osmiumocene.

In a preferred embodiment, the ETM is attached to a ribose at any position of the ribose-phosphate backbone of the nucleic acid, i.e. either the 5' or 3' terminus or any internal nucleoside. Ribose in this case can include ribose analogs. As is known in the art, nucleosides that are modified at either the 2' or 3' position of the ribose can be made, with nitrogen, oxygen, sulfur and phosphorus-containing modifications possible. Amino-modified and oxygen-modified ribose is preferred. See generally PCT publication WO 95/15971, incorporated herein by reference. These modification groups may be used as a transition metal ligand, or as a chemically functional moiety for attachment of other transition metal ligands and organometallic ligands, or organic electron donor moieties as will be appreciated by those in the art. In this embodiment, a linker such as depicted herein for "Z" may be used as well, or a conductive oligomer between the ribose and the ETM. Preferred embodiments utilize attachment at the 2' or 3' position of the ribose, with the 2' position being preferred. Thus for example, the conductive oligomers depicted in Structure 13, 14 and 15 may be replaced by ETMs; alternatively, the ETMs may be added to the free terminus of the conductive oligomer.

In a preferred embodiment, a metallocene serves as the ETM, and is attached via an amide bond as depicted below in Structure 33. The examples outline the synthesis of a preferred compound when the metallocene is ferrocene.

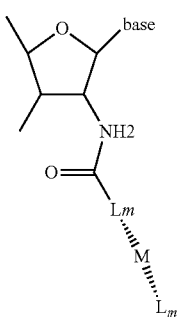

Structure 33

In a preferred embodiment, amine linkages are used, as is generally depicted in Structure 34.

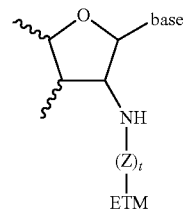

Structure 34

Z is a linker, as defined herein, with 1-16 atoms being preferred, and 2-4 atoms being particularly preferred, and t is either one or zero.

In a preferred embodiment, oxo linkages are used, as is generally depicted in Structure 35.

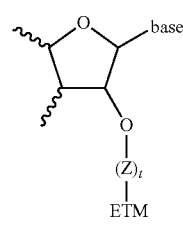

Structure 35

In Structure 35, Z is a linker, as defined herein, and t is either one or zero. Preferred Z linkers include alkyl groups including heteroalkyl groups such as $(CH_2)n$ and $(CH_2CH_2O)n$, with n from 1 to 10 being preferred, and n=1 to 4 being especially preferred, and n=4 being particularly preferred.

Linkages utilizing other heteroatoms are also possible.

In a preferred embodiment, an ETM is attached to a phosphate at any position of the ribose-phosphate backbone of the nucleic acid. This may be done in a variety of ways. In one embodiment, phosphodiester bond analogs such as phosphoramide or phosphoramidite linkages may be incorporated into a nucleic acid, where the heteroatom (i.e. nitrogen) serves as a transition metal ligand (see PCT publication WO 95/15971, incorporated by reference). Alternatively, the conductive oligomers depicted in Structures 23 and 24 may be replaced by ETMs. In a preferred embodiment, the composition has the structure shown in Structure 36.

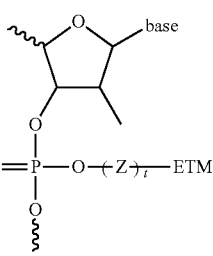

Structure 36

In Structure 36, the ETM is attached via a phosphate linkage, generally through the use of a linker, Z. Preferred Z linkers include alkyl groups, including heteroalkyl groups such as $(CH_2)_n$, $(CH_2CH_2O)_n$, with n from 1 to 10 being preferred, and n=1 to 4 being especially preferred, and n=4 being particularly preferred.

In mechanism-2 systems, when the ETM is attached to the base or the backbone of the nucleoside, it is possible to attach the ETMs via "dendrimer" structures, as is more fully outlined below. As is generally depicted in FIG. 8, alkyl-based linkers can be used to create multiple branching structures comprising one or more ETMs at the terminus of each branch. Generally, this is done by creating branch points containing multiple hydroxy groups, which optionally can then be used to add additional branch points. The terminal hydroxy groups can then be used in phosphoramidite reactions to add ETMs, as is generally done below for the nucleoside replacement and metallocene polymer reactions.

In a preferred embodiment, an ETM such as a metallocene is used as a "nucleoside replacement", serving as an ETM. For example, the distance between the two cyclopentadiene rings of ferrocene is Similar to the orthongonal distance between two bases in a double stranded nucleic acid. Other metallocenes in addition to ferrocene may be used, for example, air stable metallocenes such as those containing cobalt or ruthenium. Thus, metallocene moieties may be incorporated into the backbone of a nucleic acid, as is generally depicted in Structure 37 (nucleic acid with a ribose-phosphate backbone) and Structure 38 (peptide nucleic acid backbone). Structures 37 and 38 depict ferrocene, although as will be appreciated by those in the art, other metallocenes may be used as well. In general, air stable metallocenes are preferred, including metallocenes utilizing ruthenium and cobalt as the metal.

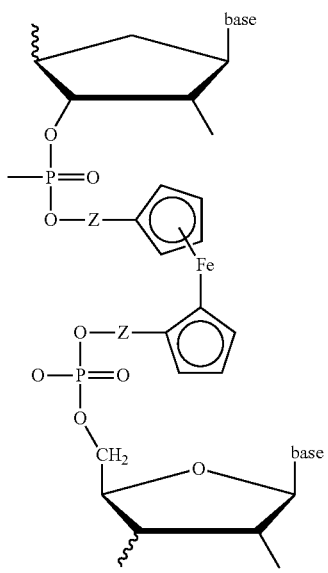

Structure 37

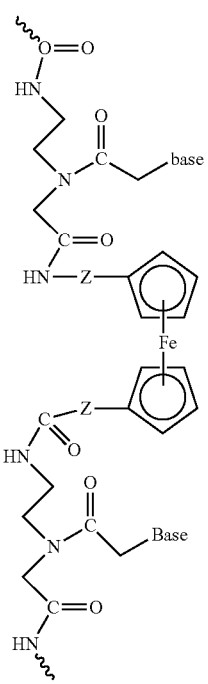

Structure 38

In Structure 37, Z is a linker as defined above, with generally short, alkyl groups, including heteroatoms such as oxygen being preferred. Generally, what is important is the length of the linker, such that minimal perturbations of a double stranded nucleic acid is effected, as is more fully described below. Thus, methylene, ethylene, ethylene glycols, propylene and butylene are all preferred, with ethylene and ethylene glycol being particularly preferred. In addition, each Z linker may be the same or different. Structure 37 depicts a ribose-phosphate backbone, although as will be appreciated by those in the art, nucleic acid analogs may also be used, including ribose analogs and phosphate bond analogs.

In Structure 38, preferred Z groups are as listed above, and again, each Z linker can be the same or different. As above, other nucleic acid analogs may be used as well.

In addition, although the structures and discussion above depicts metallocenes, and particularly ferrocene, this same general idea can be used to add ETMs in addition to metallocenes, as nucleoside replacements or in polymer embodiments, described below. Thus, for example, when the ETM is a transition metal complex other than a metallocene, comprising one, two or three (or more) ligands, the ligands can be functionalized as depicted for the ferrocene to allow the addition of phosphoramidite groups. Particularly preferred in this embodiment are complexes comprising at least two ring (for example, aryl and substituted aryl) ligands, where each of the ligands comprises functional groups for attachment via phosphoramidite chemistry. As will be appreciated by those in the art, this type of reaction, creating polymers of ETMs either as a portion of the backbone of the nucleic acid or as "side groups" of the nucleic acids, to allow amplification of the signals generated herein, can be done with virtually any ETM that can be functionalized to contain the correct chemical groups.

Thus, by inserting a metallocene such as ferrocene (or other ETM) into the backbone of a nucleic acid, nucleic acid analogs are made; that is, the invention provides nucleic acids having a backbone comprising at least one metallocene. This is distinguished from nucleic acids having metallocenes attached to the backbone, i.e. via a ribose, a phosphate, etc. That is, two nucleic acids each made up of a traditional nucleic acid or analog (nucleic acids in this case including a single nucleoside), may be covalently attached to each other via a metallocene. Viewed differently, a metallocene derivative or substituted metallocene is provided, wherein each of the two aromatic rings of the metallocene has a nucleic acid substitutent group.

In addition, as is more fully outlined below, it is possible to incorporate more than one metallocene into the backbone, either with nucleotides in between and/or with adjacent metallocenes. When adjacent metallocenes are added to the backbone, this is similar to the process described below as "metallocene polymers": that is, there are areas of metallocene polymers within the backbone.

In addition to the nucleic acid substitutent groups, it is also desirable in some instances to add additional substituent groups to one or both of the aromatic rings of the metallocene (or ETM). For example, as these nucleoside replacements are generally part of probe sequences to be hybridized with a substantially complementary nucleic acid, for example a target sequence or another probe sequence, it is possible to add substitutent groups to the metallocene rings to facilitate hydrogen bonding to the base or bases on the opposite strand. These may be added to any position on the metallocene rings. Suitable substituent groups include, but are not limited to, amide groups, amine groups, carboxylic acids, and alcohols, including substituted alcohols. In addition, these substitutent groups can be attached via linkers as well, although in general this is not preferred.

In addition, substituent groups on an ETM, particularly metallocenes such as ferrocene, may be added to alter the redox properties of the ETM. Thus, for example, in some embodiments, as is more fully described below, it may be desirable to have different ETMs attached in different ways (i.e. base or ribose attachment), on different probes, or for different purposes (for example, calibration or as an internal standard). Thus, the addition of substituent groups on the metallocene may allow two different ETMs to be distinguished.

In order to generate these metallocene-backbone nucleic acid analogs, the intermediate components are also provided. Thus, in a preferred embodiment, the invention provides phosphoramidite metallocenes, as generally depicted in Structure 39:

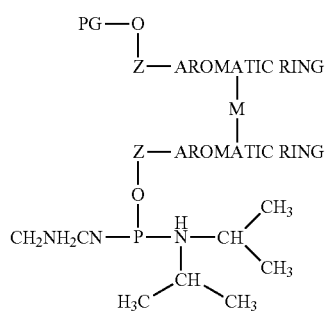

Structure 39

In Structure 39, PG is a protecting group, generally suitable for use in nucleic acid synthesis, with DMT, MMT and TMT all being preferred. The aromatic rings can either be the rings of the metallocene, or aromatic rings of ligands for transition metal complexes or other organic ETMs. The aromatic rings may be the same or different, and may be substituted as discussed herein.

Structure 40 depicts the ferrocene derivative:

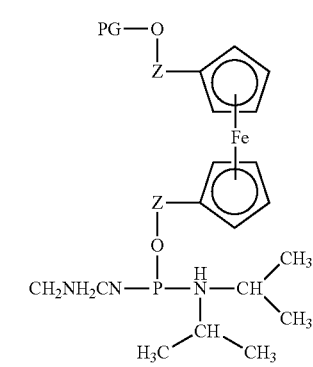

Structure 40

These phosphoramidite analogs can be added to standard oligonucleotide syntheses as is known in the art.

Structure 41 depicts the ferrocene peptide nucleic acid (PNA) monomer, that can be added to PNA synthesis as is known in the art:

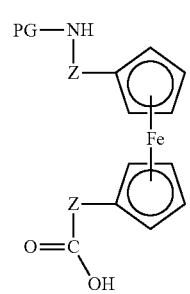

Structure 41

In Structure 41, the PG protecting group is suitable for use in peptide nucleic acid synthesis, with MMT, boc and Fmoc being preferred.

These same intermediate compounds can be used to form ETM or metallocene polymers, which are added to the nucleic acids, rather than as backbone replacements, as is more fully described below.

In a preferred embodiment, particularly for use in mechanism-2 systems, the ETMs are attached as polymers, for example as metallocene polymers, in a "branched" configuration similar to the "branched DNA" embodiments herein and as outlined in U.S. Pat. No. 5,124,246, using modified functionalized nucleotides. The general idea is as follows. A modified phosphoramidite nucleotide is generated that can ultimately contain a free hydroxy group that can be used in the attachment of phosphoramidite ETMs such as metallocenes. This free hydroxy group could be on the base or the backbone, such as the ribose or the phosphate (although as will be appreciated by those in the art, nucleic acid analogs containing other structures can also be used). The modified nucleotide is incorporated into a nucleic acid, and any hydroxy protecting groups are removed, thus leaving the free hydroxyl. Upon the addition of a phosphoramidite ETM such as a metallocene, as described above in structures 39 and 40, ETMs, such as metallocene ETMs, are added. Additional phosphoramidite ETMs such as metallocenes can be added, to form "ETM polymers", including "metallocene polymers" as depicted in FIG. 9 with ferrocene. In addition, in some embodiments, it is desirable to increase the solubility of the polymers by adding a "capping" group to the terminal ETM in the polymer, for example a final phosphate group to the metallocene. Other suitable solubility enhancing "capping" groups will be appreciated by those in the art. It should be noted that these solubility enhancing groups can be added to the polymers in other places, including to the ligand rings, for example on the metallocenes as discussed herein.

In this embodiment, the 2' position of a ribose of a phosphoramidite nucleotide is first functionalized to contain a protected hydroxy group, in this case via an oxo-linkage, although any number of linkers can be used, as is generally described herein for Z linkers. The protected modified nucleotide is then incorporated via standard phosphoramidite chemistry into a growing nucleic acid. The protecting group is removed, and the free hydroxy group is used, again using standard phosphoramidite chemistry to add a phosphoramidite metallocene such as ferrocene. A similar reaction is possible for nucleic acid analogs. For example, using peptide nucleic acids and the metallocene monomer shown in Structure 41, peptide nucleic acid structures containing metallocene polymers could be generated.

Thus, the present invention provides recruitment linkers of nucleic acids comprising "branches" of metallocene polymers. Preferred embodiments also utilize metallocene polymers from one to about 50 metallocenes in length, with from about 5 to about 20 being preferred and from about 5 to about 10 being especially preferred.

In addition, when the recruitment linker is nucleic acid, any combination of ETM attachments may be done. In general, as outlined herein, when mechanism-1 systems are used, clusters of nucleosides containing ETMs can decrease the Tm of hybridization of the probe to its target sequence; thus in general, for mechanism-1 systems, the ETMs are spaced out over the length of the sequence, or only small numbers of them are used.

In mechanism-1 systems, non-covalently attached ETMs may be used. In one embodiment, the ETM is a hybridization indicator. Hybridization indicators serve as an ETM that will preferentially associate with double stranded nucleic acid is added, usually reversibly, similar to the method of Millan et al., Anal. Chem. 65:2317-2323 (1993); Millan et al., Anal. Chem. 662943-2948 (1994), both of which are hereby expressly incorporated by reference. In this embodiment, increases in the local concentration of ETMs, due to the association of the ETM hybridization indicator with double stranded nucleic acid at the surface, can be monitored using the monolayers comprising the conductive oligomers. Hybridization indicators include intercalators and minor and/or major groove binding moieties. In a preferred embodiment, intercalators may be used; since intercalation generally only occurs in the presence of double stranded nucleic acid, only in the presence of double stranded nucleic acid will the ETMs concentrate. Intercalating transition metal complex ETMs are known in the art. Similarly, major or minor groove binding moieties, such as methylene blue, may also be used in this embodiment.

Similarly, the systems of the invention may utilize non-covalently attached ETMs, as is generally described in Napier et al., Bioconj. Chem. 8:906 (1997), hereby expressly incorporated by reference. In this embodiment, changes in the redox state of certain molecules as a result of the presence of DNA (i.e. guanine oxidation by ruthenium complexes) can be detected using the SAMs comprising conductive oligomers as well.

In a preferred embodiment, the recruitment linker is not nucleic acid, and instead may be any sort of linker or polymer. As will be appreciated by those in the art, generally any linker or polymer that can be modified to contain ETMs can be used. In general, the polymers or linkers should be reasonably soluble and contain suitable functional groups for the addition of ETMs.

As used herein, a "recruitment polymer" comprises at least two or three subunits, which are covalently attached. At least some portion of the monomeric subunits contain functional groups for the covalent attachment of ETMs. In some embodiments coupling moieties are used to covalently link the subunits with the ETMs. Preferred functional groups for attachment are amino groups, carboxy groups, oxo groups and thiol groups, with amino groups being particularly preferred. As will be appreciated by those in the art, a wide variety of recruitment polymers are possible.

Suitable linkers include, but are not limited to, alkyl linkers (including heteroalkyl (including (poly)ethylene glycol-type structures), substituted alkyl, aryalkyl linkers, etc. As above for the polymers, the linkers will comprise one or more functional groups for the attachment of ETMs, which will be done as will be appreciated by those in the art, for example through the use homo- or heterobifunctional linkers as are well known (see 1994 Pierce Chemical Company catalog, technical section on cross-linkers, pages 155-200, incorporated herein by reference).

Suitable recruitment polymers include, but are not limited to, functionalized styrenes, such as amino styrene, functionalized dextrans, and polyamino acids. Preferred polymers are polyamino acids (both poly-D-amino acids and poly-L-amino acids), such as polylysine, and polymers containing lysine and other amino acids being particularly preferred. As outlined above, in some embodiments, charged recruitment linkers are preferred, for example when non-charged target analytes are to be detected. Other suitable polyamino acids are polyglutamic acid, polyaspartic acid, co-polymers of lysine and glutamic or aspartic acid, co-polymers of lysine with alanine, tyrosine, phenylalanine, serine, tryptophan, and/or proline.

In a preferred embodiment, the recruitment linker comprises a metallocene polymer, as is described above.

The attachment of the recruitment linkers to the first portion of the label probe, i.e. the portion that binds either directly or indirectly to the target analyte, will depend on the composition of the recruitment linker, as will be appreciated by those in the art. When the recruitment linker is nucleic acid, it is generally formed during the synthesis of the first portion of the label probe, with incorporation of nucleosides containing ETMs as required. Alternatively, the first portion of the label probe and the recruitment linker may be made separately, and then attached. For example, there may be an overlapping section of complementarity, forming a section of double stranded nucleic acid that can then be chemically crosslinked, for example by using psoralen as is known in the art.

When non-nucleic acid recruitment linkers are used, attachment of the linker/polymer of the recruitment linker will be done generally using standard chemical techniques, such as will be appreciated by those in the art. For example, when alkyl-based linkers are used, attachment can be similar to the attachment of insulators to nucleic acids.

In addition, it is possible to have recruitment linkers that are mixtures of nucleic acids and non-nucleic acids, either in a linear form (i.e. nucleic acid segments linked together with alkyl linkers) or in branched forms (nucleic acids with alkyl "branches" that may contain ETMs and may be additionally branched).

In a preferred embodiment, for example when the target analyte is a nucleic acid, it is the target sequence itself that carries the ETMs, rather than the recruitment linker of a label probe. For example, as is more fully described below, it is possible to enzymatically add triphosphate nucleotides comprising the ETMs of the invention to a growing nucleic acid, for example during a polymerase chain reaction (PCR). As will be recognized by those in the art, while several enzymes have been shown to generally tolerate modified nucleotides, some of the modified nucleotides of the invention, for example the "nucleoside replacement" embodiments and putatively some of the phosphate attachments, may or may not be recognized by the enzymes to allow incorporation into a growing nucleic acid. Therefore, preferred attachments in this embodiment are to the base or ribose of the nucleotide.

Thus, for example, PCR amplification of a target sequence, as is well known in the art, will result in target sequences comprising ETMs, generally randomly incorporated into the sequence. The system of the invention can then be configured to allow detection using these ETMs.

Alternatively, as outlined more fully below, it is possible to enzymatically add nucleotides comprising ETMs to the terminus of a nucleic acid, for example a target nucleic acid. In this embodiment, an effective "recruitment linker" is added to the terminus of the target sequence, that can then be used for detection. Thus the invention provides compositions utilizing electrodes comprising monolayers of conductive oligomers and capture probes, and target sequences that comprises a first portion that is capable of hybridizing to a component of an assay complex, and a second portion that does not hybridize to a component of an assay complex and comprises at least one covalently attached electron transfer moiety. Similarly, methods utilizing these compositions are also provided.

It is also possible to have ETMs connected to probe sequences, i.e. sequences designed to hybridize to complementary sequences, i.e. in mechanism-1 sequences, although this may also be used in mechanism-2 systems. Thus, ETMs may be added to non-recruitment linkers as well. For example, there may be ETMs added to sections of label probes that do hybridize to components of the assay complex, for example the first portion, or to the target sequence as outlined above. These ETMs may be used for electron transfer detection in some embodiments, or they may not, depending on the location and system. For example, in some embodiments, when for example the target sequence containing randomly incorporated ETMs is hybridized directly to the capture probe, there may be ETMs in the portion hybridizing to the capture probe. If the capture probe is attached to the electrode using a conductive oligomer, these ETMs can be used to detect electron transfer as has been previously described. Alternatively, these ETMs may not be specifically detected.

Similarly, in some embodiments, when the recruitment linker is nucleic acid, it may be desirable in some instances to have some or all of the recruitment linker be double stranded, for example in the mechanism-2 systems. In one embodiment, there may be a second recruitment linker, substantially complementary to the first recruitment linker, that can hybridize to the first recruitment linker. In a preferred embodiment, the first recruitment linker comprises the covalently attached ETMs. In an alternative embodiment, the second recruitment linker contains the ETMs, and the first recruitment linker does not, and the ETMs are recruited to the surface by hybridization of the second recruitment linker to the first. In yet another embodiment, both the first and second recruitment linkers comprise ETMs. It should be noted, as discussed above, that nucleic acids comprising a large number of ETMs may not hybridize as well, i.e. the $T_m$ may be decreased, depending on the site of attachment and the characteristics of the ETM. Thus, in general, when multiple ETMs are used on hybridizing strands, i.e. in mechanism-1 systems, generally there are less than about 5, with less than about 3 being preferred, or alternatively the ETMs should be spaced sufficiently far apart that the intervening nuclides can sufficiently hybridize to allow good kinetics.

Thus, the present invention provides compositions comprising detection electrodes comprising monolayers comprising conductive oligomers, generally including capture probes, and either target sequences or label probes comprising recruitment linkers containing ETMs. In a preferred embodiment, the compositions of the invention are used to detect target analytes in a sample. In a preferred embodiment, the target analyte is a nucleic acid, and target sequences are detected.

As will be appreciated by those in the art, the systems of the invention may take on a large number of different configurations. In general, there are three types of systems that can be used: (1) systems in which the target sequence itself is labeled with ETMs; this is generally useful for nucleic acid systems); (2) systems in which label probes directly bind to the target analytes; and (3) systems in which label probes are indirectly bound to the target sequences, for example through the use of amplifier probes In a preferred embodiment, the target sequence itself contains the ETMs. As discussed above, this may be done using target sequences that have ETMs incorporated at any number of positions, as outlined above. In this embodiment, as for the others of the system, the 3'-5' orientation of the probes and targets is chosen to get the ETM-containing structures (i.e. recruitment linkers or target sequences) as close to the surface of the monolayer as possible, and in the correct orientation. This may be done using attachment via insulators or conductive oligomers as is generally shown in the Figures. In addition, as will be appreciated by those in the art, multiple capture probes can be utilized, for example in a configuration, wherein the 5'-3' orientation of the capture probes is different, or where "loops" of target form when multiples of capture probes are used.

In a preferred embodiment, the label probes directly hybridize to the target sequences. In these embodiments, the target sequence is preferably, but not required to be, immobilized on the surface using capture probes, including capture extender probes. Label probes are then used to bring the ETMs into proximity of the surface of the monolayer comprising conductive oligomers. In a preferred embodiment, multiple label probes are used; that is, label probes are designed such that the portion that hybridizes to the target sequence can be different for a number of different label probes, such that amplification of the signal occurs, since multiple label probes can bind for every target sequence. Thus, as depicted in the figures, n is an integer of at least one. Depending on the sensitivity desired, the length of the target sequence, the number of ETMs per label probe, etc., preferred ranges of n are from 1 to 50, with from about 1 to about 20 being particularly preferred, and from about 2 to about 5 being especially preferred. In addition, if "generic" label probes are desired, label extender probes can be used as generally described below for use with amplifier probes.

As above, generally in this embodiment the configuration of the system and the label probes are designed to recruit the ETMs as close as possible to the monolayer surface.

In a preferred embodiment, the label probes are hybridized to the target sequence indirectly. That is, the present invention finds use in novel combinations of signal amplification technologies and electron transfer detection on electrodes, which may be particularly useful in sandwich hybridization assays, as generally depicted in the Figures for nucleic acid embodiments; similar systems can be developed for non-nucleic acid target analytes. In these embodiments, the amplifier probes of the invention are bound to the target sequence in a sample either directly or indirectly. Since the amplifier probes preferably contain a relatively large number of amplification sequences that are available for binding of label probes, the detectable signal is significantly increased, and allows the detection limits of the target to be significantly improved. These label and amplifier probes, and the detection methods described herein, may be used in essentially any known nucleic acid hybridization formats, such as those in which the target is bound directly to a solid phase or in sandwich hybridization assays in which the target is bound to one or more nucleic acids that are in turn bound to the solid phase.

In general, these embodiments may be described as follows with particular reference to nucleic acids. An amplifier probe is hybridized to the target sequence, either directly or through the use of a label extender probe, which serves to allow "generic" amplifier probes to be made. The target sequence is preferably, but not required to be, immobilized on the electrode using capture probes. Preferably, the amplifier probe contains a multiplicity of amplification sequences, although in some embodiments, as described below, the amplifier probe may contain only a single amplification sequence. The amplifier probe may take on a number of different forms; either a branched conformation, a dendrimer conformation, or a linear "string" of amplification sequences. These amplification sequences are used to form hybridization complexes with label probes, and the ETMs can be detected using the electrode.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Generally, the methods are as follows. In a preferred embodiment, the target is moved into the detection module. In general, two methods may be employed; the assay complexes as described below are formed first (i.e. all the soluble components are added together, either simultaneously or sequentially, including capture extender probes, label probes, amplification probes, label extender probes, etc.), "upstream" of the detection module, and then the complex is added to the surface for subsequent binding to a detection electrode. Alternatively, the target may be added where it binds the capture binding ligand and then additional components are added. The latter is described in detail below, but either procedure may be followed. Similarly, some components may be added, electrophoresed, and other components added; for example, the target analyte may be combined with any capture extender probes and then transported, etc.

In addition, as outlined herein, "washing" steps may be done using the introduction of buffer into the detection module, wherein excess reagents (non-bound analytes, excess probes, etc.) can be driven from the surface.

The sample is introduced to the electrode in the detection module, and then immobilized or attached to the detection electrode. In one embodiment, this is done by forming an attachment complex (frequently referred to herein as a hybridization complex when nucleic acid components are used) between a capture probe and a portion of the target analyte. A preferred embodiment utilizes capture extender binding ligands (also called capture extender probes herein); in this embodiment, an attachment complex is formed between a portion of the target sequence and a first portion of a capture extender probe, and an additional attachment complex between a second portion of the capture extender probe and a portion of the capture probe. Additional preferred embodiments utilize additional capture probes, thus forming an attachment complex between a portion of the target sequence and a first portion of a second capture extender probe, and an attachment complex between a second portion of the second capture extender probe and a second portion of the capture probe.

Alternatively, the attachment of the target sequence to the electrode is done simultaneously with the other reactions.

The method proceeds with the introduction of amplifier probes, if utilized. In a preferred embodiment, the amplifier probe comprises a first probe sequence that is substantially complementary to a portion of the target sequence, and at least one amplification sequence.

In one embodiment, the first probe sequence of the amplifier probe is hybridized to the target sequence, and any unhybridized amplifier probe is removed. This will generally be done as is known in the art, and depends on the type of assay. When the target sequence is immobilized on a surface such as an electrode, the removal of excess reagents generally is done via one or more washing steps, as will be appreciated by those in the art. In this embodiment, the target may be immobilized on any solid support. When the target sequence is not immobilized on a surface, the removal of excess reagents such as the probes of the invention may be done by flowing the sample past a solid support that contain complementary sequences to the probes, such that the excess probes bind to the solid support.

The reaction mixture is then subjected to conditions (temperature, high salt, changes in pH, etc.) under which the amplifier probe disassociates from the target sequence, and the amplifier probe is collected. The amplifier probe may then be added to an electrode comprising capture probes for the amplifier probes, label probes added, and detection is achieved.

In a preferred embodiment, a larger pool of probe is generated by adding more amplifier probe to the target sequence and the hybridization/disassociation reactions are repeated, to generate a larger pool of amplifier probe. This pool of amplifier probe is then added to an electrode comprising amplifier capture probes, label probes added, and detection proceeds.

In this embodiment, it is preferred that the target sequence be immobilized on a solid support, including an electrode, using the methods described herein; although as will be appreciated by those in the art, alternate solid support attachment technologies may be used, such as attachment to glass, polymers, etc. It is possible to do the reaction on one solid support and then add the pooled amplifier probe to an electrode for detection.

In a preferred embodiment, the amplifier probe comprises a multiplicity of amplification sequences.

In one embodiment, the first probe sequence of the amplifier probe is hybridized to the target sequence, and any unhybridized amplifier probe is removed. Again, preferred embodiments utilize immobilized target sequences, wherein the target sequences are immobilized by hybridization with capture probes that are attached to the electrode, or hybridization to capture extender probes that in turn hybridize with immobilized capture probes as is described herein. Generally, in these embodiments, the capture probes and the detection probes are immobilized on the electrode, generally at the same "address".

In a preferred embodiment, the first probe sequence of the amplifier probe is hybridized to a first portion of at least one label extender probe, and a second portion of the label extender probe is hybridized to a portion of the target sequence. Other preferred embodiments utilize more than one label extender probe.

In a preferred embodiment, the amplification sequences of the amplifier probe are used directly for detection, by hybridizing at least one label probe sequence.

The invention thus provides assay complexes that minimally comprise a target sequence and a label probe. "Assay complex" herein is meant the collection of attachment or hybridization complexes comprising analytes, including binding ligands and targets, that allows detection. The composition of the assay complex depends on the use of the different probe component outlined herein. The assay complexes may include the target sequence, label probes, capture extender probes, label extender probes, and amplifier probes, as outlined herein, depending on the configuration used.

The assays are generally run under stringency conditions which allows formation of the label probe attachment complex only in the presence of target. Stringency can be controlled by altering a step parameter that is a thermodynamic variable, including, but not limited to, temperature, formamide concentration, salt concentration, chaotropic salt concentration pH, organic solvent concentration, etc. Stringency may also include the use of an electrophoretic step to drive non-specific (i.e. low stringency) materials away from the detection electrode.

These parameters may also be used to control non-specific binding, as is generally outlined in U.S. Pat. No. 5,681,697. Thus it may be desirable to perform certain steps at higher stringency conditions; for example, when an initial hybridization step is done between the target sequence and the label extender and capture extender probes. Running this step at conditions which favor specific binding can allow the reduction of non-specific binding.

In a preferred nucleic acid embodiment, when all of the components outlined herein are used, a preferred method is as follows. Single-stranded target sequence is incubated under hybridization conditions with the capture extender probes and the label extender probes. A preferred embodiment does this reaction in the presence of the electrode with immobilized capture probes, although this may also be done in two steps, with the initial incubation and the subsequent addition to the electrode. Excess reagents are washed off, and amplifier probes are then added. If preamplifier probes are used, they may be added either prior to the amplifier probes or simultaneously with the amplifier probes. Excess reagents are washed off, and label probes are then added. Excess reagents are washed off, and detection proceeds as outlined below.

In one embodiment, a number of capture probes (or capture probes and capture extender probes) that are each substantially complementary to a different portion of the target sequence are used.

Again, as outlined herein, when amplifier probes are used, the system is generally configured such that upon label probe binding, the recruitment linkers comprising the ETMs are placed in proximity either to the monolayer surface containing conductive oligomers (mechanism-2) or in proximity to detection probes. Thus for example, for mechanism-2 systems, when the ETMs are attached via "dendrimer" type structures as outlined herein, the length of the linkers from the nucleic acid point of attachment to the ETMs may vary, particularly with the length of the capture probe when capture extender probes are used. That is, longer capture probes, with capture extenders, can result in the target sequences being "held" further away from the surface than for shorter capture probes. Adding extra linking sequences between the probe nucleic acid and the ETMs can result in the ETMs being spatially closer to the surface, giving better results. Similarly, for mechanism-1 systems, the length of the recruitment linker, the length of the detection probe, and their distance, may be optimized.

In addition, if desirable, nucleic acids utilized in the invention may also be ligated together prior to detection, if applicable, by using standard molecular biology techniques such as the use of a ligase. Similarly, if desirable for stability, cross-linking agents may be added to hold the structures stable.

As will be appreciated by those in the art, while described for nucleic acids, the systems outlined herein can be used for other target analytes as well.

The compositions of the invention are generally synthesized as outlined herein and in U.S. Ser. Nos. 08/743,798, 08/873,978, 08/911,085, 08/911,085, and PCT US97/20014, all of which are expressly incorporated by reference, generally utilizing techniques well known in the art. As will be appreciated by those in the art, many of the techniques outlined below are directed to nucleic acids containing a ribose-phosphate backbone. However, as outlined above, many alternate nucleic acid analogs may be utilized, some of which may not contain either ribose or phosphate in the backbone. In these embodiments, for attachment at positions other than the base, attachment is done as will be appreciated by those in the art, depending on the backbone. Thus, for example, attachment can be made at the carbon atoms of the PNA backbone, as is described below, or at either terminus of the PNA.

The compositions may be made in several ways. A preferred method first synthesizes a conductive oligomer attached to a nucleoside, with addition of additional nucleosides to form the capture probe followed by attachment to the electrode. Alternatively, the whole capture probe may be made and then the completed conductive oligomer added, followed by attachment to the electrode. Alternatively, a monolayer of conductive oligomer (some of which have functional groups for attachment of capture probes) is attached to the electrode first, followed by attachment of the capture probe. The latter two methods may be preferred when conductive oligomers are used which are not stable in the solvents and under the conditions used in traditional nucleic acid synthesis.

In a preferred embodiment, the detection module compositions of the invention are made by first forming the conductive oligomer covalently attached to the nucleoside, followed by the addition of additional nucleosides to form a capture probe nucleic acid, with the last step comprising the addition of the conductive oligomer to the electrode.

The attachment of the conductive oligomer to the nucleoside may be done in several ways. In a preferred embodiment, all or part of the conductive oligomer is synthesized first (generally with a functional group on the end for attachment to the electrode), which is then attached to the nucleoside. Additional nucleosides are then added as required, with the last step generally being attachment to the electrode. Alternatively, oligomer units are added one at a time to the nucleoside, with addition of additional nucleosides and attachment to the electrode. A number of representative syntheses are shown in the Figures of PCT US97/20014.

The conductive oligomer is then attached to a nucleoside that may contain one (or more) of the oligomer units, attached as depicted herein.

In a preferred embodiment, attachment is to a ribose of the ribose-phosphate backbone, including amide and amine linkages. In a preferred embodiment, there is at least a methylene group or other short aliphatic alkyl groups (as a Z group) between the nitrogen attached to the ribose and the aromatic ring of the conductive oligomer.

Alternatively, attachment is via a phosphate of the ribose-phosphate backbone, as generally outlined in PCT US97/20014.

In a preferred embodiment, attachment is via the base. In a preferred embodiment, protecting groups may be added to the base prior to addition of the conductive oligomers, as is generally known in the art. In addition, the palladium cross-coupling reactions may be altered to prevent dimerization problems; i.e. two conductive oligomers dimerizing, rather than coupling to the base.

Alternatively, attachment to the base may be done by making the nucleoside with one unit of the oligomer, followed by the addition of others.

Once the modified nucleosides are prepared, protected and activated, prior to attachment to the electrode, they may be incorporated into a growing oligonucleotide by standard synthetic techniques (Gait, Oligonucleotide Synthesis: A Practical Approach, IRL Press, Oxford, UK 1984; Eckstein) in several ways.

In one embodiment, one or more modified nucleosides are converted to the triphosphate form and incorporated into a growing oligonucleotide chain by using standard molecular biology techniques such as with the use of the enzyme DNA polymerase I, T4 DNA polymerase, T7 DNA polymerase, Taq DNA polymerase, reverse transcriptase, and RNA polymerases. For the incorporation of a 3' modified nucleoside to a nucleic acid, terminal deoxynucleotidyltransferase may be used. (Ratliff, Terminal deoxynucleotidyltransferase. In The Enzymes, Vol 14A. P. D. Boyer ed. pp 105-118. Academic Press, San Diego, Calif. 1981). Thus, the present invention provides deoxyribonucleoside triphosphates comprising a covalently attached ETM. Preferred embodiments utilize ETM attachment to the base or the backbone, such as the ribose (preferably in the 2' position), as is generally depicted below in Structures 42 and 43:

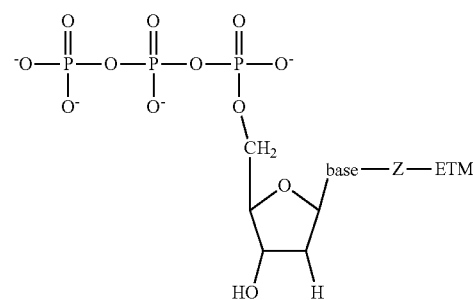

Structure 42

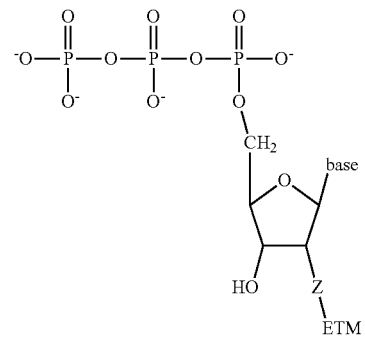

Structure 43

Thus, in some embodiments, it may be possible to generate the nucleic acids comprising ETMs in situ. For example, a target sequence can hybridize to a capture probe (for example on the surface) in such a way that the terminus of the target sequence is exposed, i.e. unhybridized. The addition of enzyme and triphosphate nucleotides labelled with ETMs allows the in situ creation of the label. Similarly, using labeled nucleotides recognized by polymerases can allow simultaneous PCR and detection; that is, the target sequences are generated in situ.

In a preferred embodiment, the modified nucleoside is converted to the phosphoramidite or Hphosphonate form, which are then used in solid-phase or solution syntheses of oligonucleotides. In this way the modified nucleoside, either for attachment at the ribose (i.e. amino- or thiol-modified nucleosides) or the base, is incorporated into the oligonucleotide at either an internal position or the 5' terminus. This is generally done in one of two ways. First, the 5' position of the ribose is protected with 4',4-dimethoxytrityl (DMT) followed by reaction with either 2-cyanoethoxy-bisdiisopropylaminophosphine in the presence of diisopropylammonium tetrazolide, or by reaction with chlorodiisopropylamino 2'-cyanoethyoxyphosphine, to give the phosphoramidite as is known in the art although other techniques may be used as will be appreciated by those in the art. See Gait, supra; Caruthers, Science 230:281 (1985), both of which are expressly incorporated herein by reference.

For attachment of a group to the 3' terminus, a preferred method utilizes the attachment of the modified nucleoside (or the nucleoside replacement) to controlled pore glass (CPG) or other oligomeric supports. In this embodiment, the modified nucleoside is protected at the 5' end with DMT, and then reacted with succinic anhydride with activation. The resulting succinyl compound is attached to CPG or other oligomeric supports as is known in the art. Further phosphoramidite nucleosides are added, either modified or not, to the 5' end after deprotection. Thus, the present invention provides conductive oligomers or insulators covalently attached to nucleosides attached to solid oligomeric supports such as CPG, and phosphoramidite derivatives of the nucleosides of the invention.

The invention further provides methods of making label probes with recruitment linkers comprising ETMs. These synthetic reactions will depend on the character of the recruitment linker and the method of attachment of the ETM, as will be appreciated by those in the art. For nucleic acid recruitment linkers, the label probes are generally made as outlined herein with the incorporation of ETMs at one or more positions. When a transition metal complex is used as the ETM, synthesis may occur in several ways. In a preferred embodiment, the ligand(s) are added to a nucleoside, followed by the transition metal ion, and then the nucleoside with the transition metal complex attached is added to an oligonucleotide, i.e. by addition to the nucleic acid synthesizer. Alternatively, the ligand(s) may be attached, followed by incorporation into a growing oligonucleotide chain, followed by the addition of the metal ion.

In a preferred embodiment, ETMs are attached to a ribose of the ribose-phosphate backbone. This is generally done as is outlined herein for conductive oligomers, as described herein, and in PCT publication WO 95/15971, using amino-modified or oxo-modified nucleosides, at either the 2' or 3' position of the ribose. The amino group may then be used either as a ligand, for example as a transition metal ligand for attachment of the metal ion, or as a chemically functional group that can be used for attachment of other ligands or organic ETMs, for example via amide linkages, as will be appreciated by those in the art. For example, the examples describe the synthesis of nucleosides with a variety of ETMs attached via the ribose.

In a preferred embodiment, ETMs are attached to a phosphate of the ribose-phosphate backbone. As outlined herein, this may be done using phosphodiester analogs such as phosphoramidite bonds, see generally PCT publication WO 95115971, or can be done in a similar manner to that described in PCT US97/20014, where the conductive oligomer is replaced by a transition metal ligand or complex or an organic ETM.

Attachment to alternate backbones, for example peptide nucleic acids or alternate phosphate linkages will be done as will be appreciated by those in the art.

In a preferred embodiment, ETMs are attached to a base of the nucleoside. This may be done in a variety of ways. In one embodiment, amino groups of the base, either naturally occurring or added as is described herein (see the figures, for example), are used either as ligands for transition metal complexes or as a chemically functional group that can be used to add other ligands, for example via an amide linkage, or organic ETMs. This is done as will be appreciated by those in the art. Alternatively, nucleosides containing halogen atoms attached to the heterocyclic ring are commercially available. Acetylene linked ligands may be added using the halogenated bases, as is generally known; see for example, Tzalis et al., Tetrahedron Lett. 36(34):6017-6020 (1995); Tzalis et al., Tetrahedron Lett. 36(2):3489-3490 (1995); and Tzalis et al., Chem. Communications (in press) 1996, all of which are hereby expressly incorporated by reference. See also the figures and the examples, which describes the synthesis of metallocenes (in this case, ferrocene) attached via acetylene linkages to the bases.

In one embodiment, the nucleosides are made with transition metal ligands, incorporated into a nucleic acid, and then the transition metal ion and any remaining necessary ligands are added as is known in the art. In an alternative embodiment, the transition metal ion and additional ligands are added prior to incorporation into the nucleic acid.

Once the nucleic acids of the invention are made, with a covalently attached attachment linker (i.e. either an insulator or a conductive oligomer), the attachment linker is attached to the electrode. The method will vary depending on the type of electrode used. As is described herein, the attachment linkers are generally made with a terminal "A" linker to facilitate attachment to the electrode. For the purposes of this application, a sulfur-gold attachment is considered a covalent attachment.

In a preferred embodiment, conductive oligomers, insulators, and attachment linkers are covalently attached via sulfur linkages to the electrode. However, surprisingly, traditional protecting groups for use of attaching molecules to gold electrodes are generally not ideal for use in both synthesis of the compositions described herein and inclusion in oligonucleotide synthetic reactions. Accordingly, the present invention provides novel methods for the attachment of conductive oligomers to gold electrodes, utilizing unusual protecting groups, including ethylpyridine, and trimethylsilylethyl as is depicted in the Figures. However, as will be appreciated by those in the art, when the conductive oligomers do not contain nucleic acids, traditional protecting groups such as acetyl groups and others may be used. See Greene et al., supra.

This may be done in several ways. In a preferred embodiment, the subunit of the conductive oligomer which contains the sulfur atom for attachment to the electrode is protected with an ethyl-pyridine or trimethylsilylethyl group. For the former, this is generally done by contacting the subunit containing the sulfur atom (preferably in the form of a sulfhydryl) with a vinyl pyridine group or vinyl trimethylsilylethyl group under conditions whereby an ethylpyridine group or trimethylsilylethyl group is added to the sulfur atom.

This subunit also generally contains a functional moiety for attachment of additional subunits, and thus additional subunits are attached to form the conductive oligomer. The conductive oligomer is then attached to a nucleoside, and additional nucleosides attached. The protecting group is then removed and the sulfur-gold covalent attachment is made. Alternatively, all or part of the conductive oligomer is made, and then either a subunit containing a protected sulfur atom is added, or a sulfur atom is added and then protected. The conductive oligomer is then attached to a nucleoside, and additional nucleosides attached. Alternatively, the conductive oligomer attached to a nucleic acid is made, and then either a subunit containing a protected sulfur atom is added, or a sulfur atom is added and then protected. Alternatively, the ethyl pyridine protecting group may be used as above, but removed after one or more steps and replaced with a standard protecting group like a disulfide. Thus, the ethyl pyridine or trimethylsilylethyl group may serve as the protecting group for some of the synthetic reactions, and then removed and replaced with a traditional protecting group.

By "subunit" of a conductive polymer herein is meant at least the moiety of the conductive oligomer to which the sulfur atom is attached, although additional atoms may be present, including either functional groups which allow the addition of additional components of the conductive oligomer, or additional components of the conductive oligomer. Thus, for example, when Structure 1 oligomers are used, a subunit comprises at least the first Y group.

A preferred method comprises 1) adding an ethyl pyridine or trimethylsilylethyl protecting group to a sulfur atom attached to a first subunit of a conductive oligomer, generally done by adding a vinyl pyridine or trimethylsilylethyl group to a sulfhydryl; 2) adding additional subunits to form the conductive oligomer; 3) adding at least a first nucleoside to the conductive oligomer; 4) adding additional nucleosides to the first nucleoside to form a nucleic acid; 5) attaching the conductive oligomer to the gold electrode. This may also be done in the absence of nucleosides.

The above method may also be used to attach insulator molecules to a gold electrode.

In a preferred embodiment, a monolayer comprising conductive oligomers (and optionally insulators) i added to the electrode. Generally, the chemistry of addition is similar to or the same as the addition of conductive oligomers to the electrode, i.e. using a sulfur atom for attachment to a gold electrode, etc. Compositions comprising monolayers in addition to the conductive oligomers covalently attached to nucleic acids may be made in at least one of five ways: (1) addition of the monolayer, followed by subsequent addition of the attachment linker-nucleic acid complex; (2) addition of the attachment linker-nucleic acid complex followed by addition of the monolayer; (3) simultaneous addition of the monolayer and attachment linker-nucleic acid complex; (4) formation of a monolayer (using any of 1, or 3) which includes attachment linkers which terminate in a functional moiety suitable for attachment of a completed nucleic acid; or (5) formation of a monolayer which includes attachment linkers which terminate in a functional moiety suitable for nucleic acid synthesis, i.e. the nucleic acid is synthesized on the surface of the monolayer as is known in the art. Such suitable functional moieties include, but are not limited to, nucleosides, amino groups, carboxyl groups, protected sulfur moieties, or hydroxyl groups for phosphoramidite additions. The examples describe the formation of a monolayer on a gold electrode using the preferred method (1).

In a preferred embodiment, the nucleic acid is a peptide nucleic acid or analog. In this embodiment, the invention provides peptide nucleic acids with at least one covalently attached ETM or attachment linker. In a preferred embodiment, these moieties are covalently attached to an monomeric subunit of the PNA. By "monomeric subunit of PNA" herein is meant the —NH—CH$_2$CH$_2$—N(COCH$_2$-Base)-CH$_2$—CO monomer, or derivatives (herein included within the definition of "nucleoside") of PNA. For example, the number of carbon atoms in the PNA backbone may be altered; see generally Nielsen et al., Cherr Soc. Rev. 1997 page 73, which discloses a number of PNA derivatives, herein expressly incorporated by reference. Similarly, the amide bond linking the base to the backbone may be altered; phosphoramide and sulfonamide bonds may be used. Alternatively, the moieties are attached to an internal monomeric subunit. By "internal" herein is meant that the monomeric subunit is not either the N-terminal monomeric subunit or the C-terminal monomeric subunit. In this embodiment, the moieties can be attached either to a base or to the backbone of the monomeric subunit. Attachment to the base is done as outlined herein or known in the literature. In general, the moieties are added to a base which is then incorporated into a PNA as outlined herein. The base may be either protected, as required for incorporation into the PNA synthetic reaction, or derivatized, to allow incorporation, either prior to the addition of the chemical substituent or afterwards. Protection and derivatization of the bases is shown in PCT US97/20014. The bases can then be incorporated into monomeric subunits.

In a preferred embodiment, the moieties are covalently attached to the backbone of the PNA monomer. The attachment is generally to one of the unsubstituted carbon atoms of the monomeric subunit, preferably the a-carbon of the backbone, although attachment at either of the carbon 1 or 2 positions, or the a-carbon of the amide bond linking the base to the backbone may be done. In the case of PNA analogs, other carbons or atoms may be substituted as well. In a preferred embodiment moieties are added at the a-carbon atoms, either to a terminal monomeric subunit or an internal one.

In this embodiment, a modified monomeric subunit is synthesized with an ETM or an attachment linker, or a functional group for its attachment, and then the base is added and the modified monomer can be incorporated into a growing PNA chain.

Once generated, the monomeric subunits with covalently attached moieties are incorporated into a PNA using the techniques outlined in Will et al., Tetrahedron 51(44):12069-12082 (1995), and Vanderlaan et al., Tett. Let. 38:2249-2252 (1997), both of which are hereby expressly incorporated in their entirety. These procedures allow the addition of chemical substituents to peptide nucleic acids without destroying the chemical substituents.

As will be appreciated by those in the art, electrodes may be made that have any combination of nucleic acids, conductive oligomers and insulators.

The compositions of the invention may additionally contain one or more labels at any position. By "label" herein is meant an element (e.g. an isotope) or chemical compound that is attached to enable the detection of the compound. Preferred labels are radioactive isotopic labels, and colored or fluorescent dyes. The labels may be incorporated into the compound at any position. In addition, the compositions of the invention may also contain other moieties such as cross-linking agents to facilitate cross-linking of the target-probe complex. See for example, Lukhtanov et al., Nucl. Acids. Res. 24(4):683 (1996) and Tabone et al., Biochem. 33:375 (1994), both of which are expressly incorporate by reference.

Once made, the compositions find use in a number of applications, as described herein. In particular the compositions of the invention find use in binding assays for the detection of target analytes, in particular nucleic acid target sequences. As will be appreciated by those in the art, electrodes can be made that have a single species of binding ligand, or multiple binding ligand species, i.e. in an array format.

In addition, as outlined herein, the use of a solid support such as an electrode enables the use of these assays in an array form. For example, the use of oligonucleotide arrays are well known in the art. In addition, techniques are known for "addressing" locations within an electrode and for the surface modification of electrodes. Thus, in a preferred embodiment, arrays of different binding ligands, including nucleic acids, are laid down on the electrode, each of which are covalently attached to the electrode via an attachment linker. In this embodiment, the number of different binding ligands may vary widely, from one to thousands, with from about 4 to about 100,000 being preferred, and from about 10 to about 10,000 being particularly preferred.

Once the assay complexes of the invention are made, that minimally comprise a target analyte and a label probe, detection proceeds with electronic initiation. Without being limited by the mechanism or theory, detection is based on the transfer of electrons from the ETM to the electrode, including via the "π-way"

Detection of electron transfer, i.e. the presence of the ETMs, is generally initiated electronically, with voltage being preferred. A potential is applied to the assay complex.

Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of ETMs and in part on the conductive oligomer used, the composition and integrity of the monolayer, and what type of reference electrode is used. As described herein, ferrocene is a preferred ETM.

In a preferred embodiment, a co-reductant or co-oxidant (collectively, co-redoxant) is used, as an additional electron source or sink. See generally Sato et al., Bull. Chem. Soc. Jpn 66:1032 (1993); Uosaki et al., Electrochimica Acta 36:1799 (1991); and Alleman et al., J. Phys. Chem 100: 17050 (1996); all of which are incorporated by reference. In some cases, a copper electrode is used, which serves as a catalytic electrode, creating co-reductants or co-oxidants in situ. See Fingal et al. Anal. Chem. 69:4828 (1997), incorporated herein by reference.

In a preferred embodiment, an input electron source in solution is used in the initiation of electron transfer, preferably when initiation and detection are being done using DC current or at AC frequencies where diffusion is not limiting. In general, as will be appreciated by those in the art, preferred embodiments utilize monolayers that contain a minimum of "holes", such that short-circuiting of the system is avoided. This may be done in several general ways. In a preferred embodiment, an input electron source is used that has a lower or similar redox potential than the ETM of the label probe. Thus, at voltages above the redox potential of the input electron source, both the ETM and the input electron source are oxidized and can thus donate electrons; the ETM donates an electron to the electrode and the input source donates to the ETM. For example, ferrocene, as a ETM attached to the compositions of the invention as described in the examples, has a redox potential of roughly 200 mV in aqueous solution (which can change significantly depending on what the ferrocene is bound to, the manner of the linkage and the presence of any substitution groups). Ferrocyanide, an electron source, has a redox potential of roughly 200 mV as well (in aqueous solution). Accordingly, at or above voltages of roughly 200 mV, ferrocene is converted to ferricenium, which then transfers an electron to the electrode. Now the ferricyanide can be oxidized to transfer an electron to the ETM. In this way, the electron source (or co-reductant) serves to amplify the signal generated in the system, as the electron source molecules rapidly and repeatedly donate electrons to the ETM attached to the nucleic acid. The rate of electron donation or acceptance will be limited by the rate of diffusion of the co-reductant, the electron transfer between the co-reductant and the ETM, which in turn is affected by the concentration and size, etc.

Alternatively, input electron sources that have lower redox potentials than the ETM are used. At voltages less than the redox potential of the ETM, but higher than the redox potential of the electron source, the input source such as ferrocyanide is unable to be oxidized and thus is unable to donate an electron to the ETM; i.e. no electron transfer occurs. Once ferrocene is oxidized, then there is a pathway for electron transfer.

In an alternate preferred embodiment, an input electron source is used that has a higher redox potential than the ETM of the label probe. For example, luminol, an electron source, has a redox potential of roughly 720 mV. At voltages higher than the redox potential of the ETM, but lower than the redox potential of the electron source, i.e. 200-720 mV, the ferrocene is oxidized, and transfers a single electron to the electrode via the conductive oligomer. However, the ETM is unable to accept any electrons from the luminol electron source, since the voltages are less than the redox potential of the luminol. However, at or above the redox potential of luminol, the luminol then transfers an electron to the ETM, allowing rapid and repeated electron transfer. In this way, the electron source (or co-reductant) serves to amplify the signal generated in the system, as the electron source molecules rapidly and repeatedly donate electrons to the ETM of the label probe.

Luminol has the added benefit of becoming a chemiluminiscent species upon oxidation (see Jirka et al., Analytica Chimica Acta 284:345 (1993)), thus allowing photo-detection of electron transfer from the ETM to the electrode. Thus, as long as the luminol is unable to contact the electrode directly, i.e. in the presence of the SAM such that there is no efficient electron transfer pathway to the electrode, luminol can only be oxidized by transferring an electron to the ETM on the label probe. When the ETM is not present, i.e. when the target sequence is not hybridized to the composition of the invention, luminol is not significantly oxidized, resulting in a low photon emission and thus a low (if any) signal from the luminol. In the presence of the target, a much larger signal is generated. Thus, the measure of luminol oxidation by photon emission is an indirect measurement of the ability of the ETM to donate electrons to the electrode. Furthermore, since photon detection is generally more sensitive than electronic detection, the sensitivity of the system may be increased. Initial results suggest that luminescence may depend on hydrogen peroxide concentration, pH, and luminol concentration, the latter of which appears to be non-linear.

Suitable electron source molecules are well known in the art, and include, but are not limited to, ferricyanide, and luminol.

Alternatively, output electron acceptors or sinks could be used, i.e. the above reactions could be run in reverse, with the ETM such as a metallocene receiving an electron from the electrode, converting it to the metallicenium, with the output electron acceptor then accepting the electron rapidly and repeatedly. In this embodiment, cobalticenium is the preferred ETM.

The presence of the ETMs at the surface of the monolayer can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperometry, voltammetry, capacitance and impedance. These methods include time or frequency dependent methods based on AC or DC currents, pulsed methods, lock-in techniques, filtering (high pass, low pass, band pass), and time-resolved techniques including time-resolved fluorescence.

In one embodiment, the efficient transfer of electrons from the ETM to the electrode results in stereotyped changes in the redox state of the ETM. With many ETMs including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp 197-202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include Ru(NH$_3$)$_4$py and Ru(bpy)$_2$im as preferred examples. It should be understood that only the donor or acceptor that is being monitored by absorbance need have ideal spectral characteristics.

In a preferred embodiment, the electron transfer is detected fluorometrically. Numerous transition metal complexes, including those of ruthenium, have distinct fluorescence properties. Therefore, the change in redox state of the electron donors and electron acceptors attached to the nucleic acid can be monitored very sensitively using fluorescence, for example with Ru(4,7-biphenyl$_2$-phenanthroline)$_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays:

Alternatively, fluorescence can be measured using fiber optic sensors with nucleic acid probes in solution or attached to the fiber optic. Fluorescence is monitored using a photomultiplier tube or other, light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified nucleic acid molecules arrayed on solid surfaces. The advantage of this system is the large number of electron transfer probes that can be scanned at once using chips covered with thousands of distinct nucleic acid probes.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85-277, 1988). Preferred examples display efficient fluorescence (reasonably high quantum yields) as well as low reorganization energies. These include Ru(4,7-biphenyl$_2$-phenanthroline)$_3^{2+}$, Ru(4,4'-diphenyl-2,2'bipyridine)$_3^{2+}$ and platinum complexes (see Cummings et al., J. Am. Chem. Soc. 118:1949-1960 (1996), incorporated by reference). Alternatively, a reduction in fluorescence associated with hybridization can be measured using these systems.

In a further embodiment, electrochemiluminescence is used as the basis of the electron transfer detection. With some ETMs such as Ru$^{2+}$(bpy)$_3$, direct luminescence accompanies excited state decay. Changes in this property are associated with nucleic acid hybridization and can be monitored with a simple photomultiplier tube arrangement (see Blackburn, G. F. Clin. Chem. 37: 1534-1539 (1991); and Juris et al., supra.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry, (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the nucleic acid-conjugated electrode and a reference (counter) electrode in the sample containing target genes of interest. Electron transfer of differing efficiencies is induced in samples in the presence or absence of target nucleic acid; that is, the presence or absence of the target nucleic acid, and thus the label probe, can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the ETM and the electrode. In addition, other properties of insulators (such as resistance) and of conductors (such as conductivity, impedance and capacitance) could be used to monitor electron transfer between ETM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In a preferred embodiment, electron transfer is initiated using alternating current (AC) methods. Without being bound by theory, it appears that ETMs, bound to an electrode, generally respond similarly to an AC voltage across a circuit containing resistors and capacitors. Basically, any methods which enable the determination of the nature of these complexes, which act as a resistor and capacitor, can be used as the basis of detection. Surprisingly, traditional electrochemical theory, such as exemplified in Laviron et al., J. Electroanal. Chem. 97:135 (1979) and Laviron et al., J. Electroanal. Chem. 105:35 (1979), both of which are incorporated by reference, do not accurately model the systems described herein, except for very small $E_{AC}$ (less than 10 mV) and relatively large numbers of molecules. That is, the AC current (I) is not accurately described by Laviron's equation. This may be due in part to the fact that this theory assumes an unlimited source and sink of electrons, which is not true in the present systems.

Accordingly, alternate equations were developed, using the Nernst equation and first principles to develop a model which more closely simulates the results. This was derived as follows. The Nernst equation, Equation 1 below, describes the ratio of oxidized (0) to reduced (R) molecules (number of molecules=n) at any given voltage and temperature, since not every molecule gets oxidized at the same oxidation potential.

Equation 1

$$E_{DC} = E_O + \frac{RT}{nF} \ln \frac{[O]}{[R]} \tag{1}$$

$E_{DC}$ is the electrode potential, $E_0$ is the formal potential of the metal complex, R is the gas constant, T is the temperature in degrees Kelvin, n is the number of electrons transferred, F is faraday's constant, [0] is the concentration of oxidized molecules and [R] is the concentration of reduced molecules.

The Nernst equation can be rearranged as shown in Equations 2 and 3: inr

Equation 2

$$E_{DC} - E_O = \frac{RT}{nF} \ln \frac{[O]}{[R]} \tag{2}$$

$E_{DC}$ is the DC component of the potential.

Equation 3

$$\exp \frac{nF}{RT}(E_{DC} - E_O) = \frac{[O]}{[R]} \tag{3}$$

Equation 3 can be rearranged as follows, using normalization of the concentration to equal I for simplicity, as shown in Equations 4, 5 and 6. This requires the subsequent multiplication by the total number of molecules.

[O]+[R]=1    Equation 4

[O]=1-[R]    Equation 5

[R]=1-[O]    Equation 6

Plugging Equation 5 and 6 into Equation 3, and the fact that nF/RT equals 38.9 V$^{-1}$, for n=1, gives Equations 7 and 8, which define [0] and [R], respectively:

Equation 7

$$[O] = \frac{\exp^{38.9(E-E_O)}}{1 + \exp^{38.9(E-E_O)}} \tag{4}$$

Equation 8

$$[R] = \frac{1}{1 + \exp^{38.9(E-E_O)}} \tag{5}$$

Taking into consideration the generation of an AC faradaic current, the ratio of [O]|[R] at any given potential must be evaluated. At a particular $E_{DC}$ with an applied $E_{AC}$, as is generally described herein, at the apex of the $E_{AC}$, more molecules will be in the oxidized state, since the voltage on the surface is now ($E_{DC}$), +$E_{AC}$); at the bottom, more will be reduced since the voltage is lower. Therefore, the AC current at a given $E_{DC}$ will be dictated by both the AC and DC voltages, as well as the shape of the Nernstian curve. Specifically, if the number of oxidized molecules at the bottom of the AC cycle is subtracted from the amount at the top of the AC cycle, the total change in a given AC cycle is obtained, as is generally described by Equation 9. Dividing by 2 then gives the AC amplitude.

Equation 9

$$i_{AC} = \frac{(\text{electrons at } [E_{DC} + E_{AC}]) - (\text{electrons at } [E_{DC} - E_{AC}])}{2}$$

Equation 10 thus describes the AC current which should result:

Equation 10

$$i_{AC} = C_o F \omega^{1/2}([O]_{E_{DC}+E_{AC}} - [O]_{E_{DC}-E_{AC}}) \tag{6}$$

As depicted in Equation 11, the total AC current will be the number of redox molecules C), times faraday's constant (F), times the AC frequency (w), times 0.5 (to take into account the AC amplitude), times the ratios derived above in Equation 7. The AC voltage is approximated by the average, $E_{AC}^{2/\pi}$.

$$AC = \frac{C_O F_\omega}{2} \left( \frac{\exp^{38.9\left[E_{DC} + \frac{2E_{AC}}{\pi} - E_O\right]}}{1 + \exp^{38.9\left[E_{DC} + \frac{2E_{AC}}{\pi} - E_O\right]}} \right) - \frac{\exp^{38.9\left[E_{DC} - \frac{2E_{AC}}{\pi} - E_O\right]}}{1 + \exp^{38.9\left[E_{DC} - \frac{2E_{AC}}{\pi} - E_O\right]}}$$

Equation 11

Using Equation 11, simulations were generated using increasing overpotential (AC voltage). FIG. 22A shows one of these simulations, while FIG. 22B depicts a simulation based on traditional theory. FIGS. 23A and 23B depicts actual experimental data using the Fc-wire of Example 7 plotted with the simulation, and shows that the model fits the experimental data very well. In some cases the current is smaller than predicted, however this has been shown to be caused by ferrocene degradation which may be remedied in a number of ways. However, Equation 11 does not incorporate the effect of electron transfer rate nor of instrument factors. Electron transfer rate is important when the rate is close to or lower than the applied frequency. Thus, the true $i_{AC}$ should be a function of all three, as depicted in Equation 12.

$i_{AC}=f(\text{Nernst factors})f(K_{ET})f(\text{instrument factors})$    Equation 12

These equations can be used to model and predict the expected AC currents in systems which use input signals comprising both AC and DC components. As outlined above, traditional theory surprisingly does not model these systems at all, except for very low voltages.

In general, non-specifically bound label probes/ETMs show differences in impedance (i.e. higher impedances) than when the label probes containing the ETMs are specifically bound in the correct orientation. In a preferred embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of ETM-containing probes and target-specific assay complex formation may be monitored.

Accordingly, when using AC initiation and detection methods, the frequency response of the system changes as a result of the presence of the ETM. By "frequency response" herein is meant a modification of signals as a result of electron transfer between the electrode and the ETM. This modification is different depending on signal frequency. A frequency response includes AC currents at one or more frequencies, phase shifts, DC offset voltages, faradaic impedance, etc.

Once the assay complex including the target sequence and label probe is made, a first input electrical signal is then applied to the system, preferably via at least the sample electrode (containing the complexes of the invention) and the counter electrode, to initiate electron transfer between the electrode and the ETM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 100 MHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In a preferred embodiment, the first input signal comprises a DC component and an AC component. That is, a DC offset voltage between the sample and counter electrodes is swept through the electrochemical potential of the ETM (for example, when ferrocene is used, the sweep is generally from 0 to 500 mV) (or alternatively, the working electrode is grounded and the reference electrode is swept from 0 to −500 mV). The sweep is used to identify the DC voltage at which the maximum response of the system is seen. This is generally at or about the electrochemical potential of the ETM. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. In a preferred embodiment, the DC offset voltage is not zero. On top of the DC offset voltage, an AC signal component of variable amplitude and frequency is applied. If the ETM is present, and can respond to the AC perturbation, an AC current will be produced due to electron transfer between the electrode and the ETM.

For defined systems, it may be sufficient to apply a single input signal to differentiate between the presence and absence of the ETM (i.e. the presence of the target sequence) nucleic acid. Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are used, although as outlined above, DC voltage sweeps are preferred. This may be done at a single frequency, or at two or more frequencies.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as those that do not possess optimal spacing configurations.

In a preferred embodiment, measurements of the system are taken at at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the ETM, higher frequencies result in a loss or decrease of output signal. At some point, the frequency will be greater than the rate of electron transfer between the ETM and the electrode, and then the output signal will also drop.

In one embodiment, detection utilizes a single measurement of output signal at a single frequency. That is, the frequency response of the system in the absence of target sequence, and thus the absence of label probe containing ETMs, can be previously determined to be very low at a particular high frequency. Using this information, any response at a particular frequency, will show the presence of the assay complex. That is, any response at a particular frequency is characteristic of the assay complex. Thus, it may only be necessary to use a single input high frequency, and any changes in frequency response is an indication that the ETM is present, and thus that the target sequence is present.

In addition, the use of AC techniques allows the significant reduction of background signals at any single frequency due to entities other than the ETMs, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, i.e. have partial or insufficient monolayers, i.e. where the solvent is accessible to the electrode. As outlined above, in DC techniques, the presence of "holes" where the electrode is accessible to the solvent can result in solvent charge carriers "short circuiting" the system, i.e. the reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at at least two separate frequencies, with measurements at a plurality of frequencies being preferred. A plurality of frequencies includes a scan. For example, measuring the output signal, e.g., the AC current, at a low input frequency such as 1-20 Hz, and comparing the response to the output signal at high frequency such as 10-100 kHz will show a frequency response difference between the presence and absence of the ETM. In a preferred embodiment, the frequency response is determined at at least two, preferably at least about five, and more preferably at least about ten frequencies.

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the ETM; the solvent; and the type and concentration of salt. At a given input signal, the presence and magnitude of the output signal will depend in general on the presence or absence of the ETM, the placement and distance of the ETM from the surface of the monolayer and the character of the input signal. In some embodiments, it may be possible to distinguish between non-specific binding of label probes and the formation of target specific assay complexes containing label probes, on the basis of impedance.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In a preferred embodiment, the output signal is phase shifted in the AC component relative to the input signal. Without being bound by theory, it appears that the systems of the present invention may be sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between the presence and absence of the ETM, and/or differences between the presence of target-specific assay complexes comprising label probes and non-specific binding of the label probes to the system components.

The output signal is characteristic of the presence of the ETM; that is, the output signal is characteristic of the presence of the target-specific assay complex comprising label probes and ETMs. In a preferred embodiment, the basis of the detection is a difference in the faradaic impedance of the system as a result of the formation of the assay complex. Faradaic impedance is the impedance of the system between the electrode and the ETM. Faradaic impedance is quite different from the bulk or dielectric impedance, which is the impedance of the bulk solution between the electrodes. Many factors may change the faradaic impedance which may not effect the bulk impedance, and vice versa. Thus, the assay complexes comprising the nucleic acids in this system have a certain faradaic impedance, that will depend on the distance between the ETM and the electrode, their electronic properties, and the composition of the intervening medium, among other things. Of importance in the methods of the invention is that the faradaic impedance between the ETM and the electrode is significantly different depending on whether the label probes containing the ETMs are specifically or non-specifically bound to the electrode.

Accordingly, the present invention further provides electronic devices or apparatus for the detection of analytes using the compositions of the invention. The apparatus includes a test chamber for receiving a sample solution which has at least a first measuring or sample electrode, and a second measuring or counter electrode. Three electrode systems are also useful. The first and second measuring electrodes are in contact with a test sample receiving region, such that in the presence of a liquid test sample, the two electrophoresis electrodes may be in electrical contact.

In a preferred embodiment, the apparatus also includes detection electrodes comprising a single stranded nucleic acid capture probe covalently attached via an attachment linker, and a monolayer comprising conductive oligomers, such as are described herein.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target nucleic acid.

Thus, the compositions of the present invention may be used in a variety of research, clinical, quality control, or field testing settings.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of antiHIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella*, *Campylobacter*, *Vibrio cholerae*, *Leishmania*, enterotoxic strains of *E. coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

Thus, the present invention provides for extremely specific and sensitive probes, which may, in some embodiments, detect target sequences without removal of unhybridized probe. This will be useful in the generation of automated gene probe assays.

Alternatively, the compositions of the invention are useful to detect successful gene amplification in PCR, thus allowing successful PCR reactions to be an indication of the presence or absence of a target sequence. PCR may be used in this manner in several ways. For example, in one embodiment, the PCR reaction is done as is known in the art, and then added to a composition of the invention comprising the target nucleic acid with a ETM, covalently attached to an electrode via a conductive oligomer with subsequent detection of the target sequence. Alternatively, PCR is done using nucleotides labelled with a ETM, either in the presence of, or with subsequent addition to, an electrode with a conductive oligomer and a target nucleic acid. Binding of the PCR product containing ETMs to the electrode composition will allow detection via electron transfer. Finally, the nucleic acid attached to the electrode via a conductive polymer may be one PCR primer, with addition of a second primer labelled with an ETM. Elongation results in double stranded nucleic acid with a ETM and electrode covalently attached. In this way, the present invention is used for PCR detection of target sequences.

In a preferred embodiment, the arrays are used for mRNA detection. A preferred embodiment utilizes either capture probes or capture extender probes that hybridize close to the 3' polyadenylation tail of the mRNAs. This allows the use of one species of target binding probe for detection, i.e. the probe contains a poly-T portion that will bind to the poly-A tail of the mRNA target. Generally, the probe will contain a second portion, preferably non-poly-T, that will bind to the detection probe (or other probe). This allows one target-binding probe to be made, and thus decreases the amount of different probe synthesis that is done.

In a preferred embodiment, the use of restriction enzymes and ligation methods allows the creation of "universal" arrays. In this embodiment, monolayers comprising capture probes that comprise restriction endonuclease ends, as is generally depicted in FIG. 6. By utilizing complementary portions of nucleic acid, while leaving "sticky ends", an array comprising any number of restriction endonuclease sites is made. Treating a target sample with one or more of these restriction endonucleases allows the targets to bind to the array. This can be done without knowing the sequence of the target. The target sequences can be ligated, as desired, using standard methods such as ligases, and the target sequence detected, using either standard labels or the methods of the invention.

The present invention provides methods which can result in sensitive detection of nucleic acids. In a preferred embodiment, less than about $10 \times 10^6$ molecules are detected, with less than about $10 \times 10^5$ being preferred, less than $10 \times 10^4$ being particularly preferred, less than about $10 \times 10^3$ being especially preferred, and less than about $10 \times 10^2$ being most preferred. As will be appreciated by those in the art, this assumes a 1:1 correlation between target sequences and reporter molecules; if more than one reporter molecule (i.e. electron transfer moeity) is used for each target sequence, the sensitivity will go up.

While the limits of detection are currently being evaluated, based on the published electron transfer rate through DNA, which is roughly $1 \times 10^6$ electrons/sec/duplex for an 8 base pair separation (see Meade et al., Angw. Chem. Eng. Ed., 34:352 (1995)) and high driving forces, AC frequencies of about 100 kHz should be possible. As the preliminary results show, electron transfer through these systems is quite efficient, resulting in nearly $100 \times 10^3$ electrons/sec, resulting in potential femtoamp sensitivity for very few molecules.

As will be appreciated by those in the art, the modules of the invention can be configured in a variety of ways, depending on the number and size of samples, and the number and type of desired manipulations. Several preferred embodiments are shown in the Figures.

As outlined herein, the devices of the invention can be used in combination with apparatus for delivering and receiving fluids to and from the devices. The apparatus can include a "nesting site" for placement of the device(s) to hold them in place and for registering inlet and outlet ports, if present. The apparatus may also include pumps ("off chip pumps"), and means for viewing the contents of the devices, including microscopes, cameras, etc. The apparatus may include electrical contacts in the nesting region which mate with contacts integrated into the structure of the chip, to power heating or electrophoresis, for example. The apparatus may be provided with conventional circuitry sensors in communication with sensors in the device for thermal regulation, for example for PCR thermal regulation. The apparatus may also include a computer system comprising a microprocessor for control of the various modules of the system as well as for data analysis.

All references cited herein are incorporated by reference in their entirety.

I claim:

1. A microfluidic device for the detection of a target analyte in a fluid sample, said device comprising:
   a) a solid support comprising a first plurality of electrodes configured for electrokinetic movement of at least a portion of the sample upon application of a voltage; and
   b) a detection module comprising a second plurality of electrodes configured for electrochemical detection of the target analyte, each comprising a binding ligand and a self-assembled monolayer;
   wherein the electrokinetic movement is electroosmotic movement or electrohydrodynamic movement.

2. The microfluidic device according to claim 1, wherein the target analyte is a nucleic acid.

3. The microfluidic device according to claim 2, wherein the electrokinetic movement is electroosmotic movement.

4. The microfluidic device according to claim 2, wherein the electrokinetic movement is electrohydrodynamic movement.

5. The microfluidic device according to claim 1, wherein the target analyte is a protein.

6. A method for the detection of a target analyte in a fluid sample, said method comprising:
   a) introducing the sample into the microfluidic device of claim 1;
   b) applying a voltage to the first plurality of electrodes to move at least a portion of the sample to the detection module; and
   c) detecting the presence of the target analyte using the second plurality of electrodes.

7. The method of claim 6, further comprising forming an attachment complex between the target analyte and at least one binding ligand prior to step c), wherein the attachment complex comprises an electron transfer moiety label.

8. The method of claim 7, wherein the electron transfer moiety label is a metallocene.

9. The method of claim 8, wherein the metallocene is a ferrocene.

10. The method of claim 7, wherein the attachment complex comprises the target analyte, an immobilized capture binding ligand, and a solution binding ligand comprising the electron transfer moiety label.

11. A microfluidic device for the detection of a target analyte in a fluid sample, said device comprising:
   a) a solid support comprising a first plurality of electrodes configured for electrokinetic movement of at least a portion of the sample upon application of a voltage; and
   b) a detection module comprising a second plurality of electrodes configured for electrochemical detection of the target analyte, each comprising a binding ligand and a self-assembled monolayer;
   wherein the target analyte is a nucleic acid or a protein.

12. The microfluidic device of claim 11, wherein the electrokinetic movement is electroosmotic movement.

13. The microfluidic device of claim 11, wherein the electrokinetic movement is electrohydrodynamic movement.

14. The microfluidic device of claim 11, wherein the target analyte is a nucleic acid.

15. The microfluidic device of claim 11, wherein the target analyte is a protein.

16. A method for the detection of a target analyte in a fluid sample, said method comprising:
   a) introducing the sample into the microfluidic device of claim 11;
   b) applying a voltage to the first plurality of electrodes to move at least a portion of the sample to the detection module; and
   c) detecting the presence of the target analyte using the second plurality of electrodes.

17. The method of claim 16, further comprising forming an attachment complex between the target analyte and at least one binding ligand prior to step c), wherein the attachment complex comprises an electron transfer moiety label.

18. The method of claim 17, wherein the electron transfer moiety label is a metallocene.

19. The method of claim 18, wherein the metallocene is a ferrocene.

20. The method of claim 17, wherein the attachment complex comprises the target analyte, an immobilized capture binding ligand, and a solution binding ligand comprising the electron transfer moiety label.

* * * * *